US008470976B2

(12) United States Patent
Chook

(10) Patent No.: US 8,470,976 B2
(45) Date of Patent: Jun. 25, 2013

(54) METHODS AND COMPOSITIONS FOR TARGETING MACROMOLECULES INTO THE NUCLEUS

(75) Inventor: Yuh Min Chook, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1464 days.

(21) Appl. No.: 11/697,656

(22) Filed: Apr. 6, 2007

(65) Prior Publication Data

US 2008/0015137 A1 Jan. 17, 2008

Related U.S. Application Data

(60) Provisional application No. 60/814,127, filed on Jun. 17, 2006.

(51) Int. Cl.
*A61K 38/16* (2006.01)
*A61K 38/00* (2006.01)

(52) U.S. Cl.
USPC ........................... 530/358; 530/300; 514/21.3

(58) Field of Classification Search
None
See application file for complete search history.

(56) References Cited

PUBLICATIONS

Ngo et al., The Protein Folding Problem and Tertiary Structure Prediction (1994), pp. 492-495.*
Wells, Aditivity of Mutational Effects in Proteins, 1990, Biochemistry, vol. 26, No. 37, pp. 8509-8517.*
Allemand, E., et al., "Regulation of heterogenous nuclear ribonucleoprotein A1 transport by phosphorylation in cells stressed by osmotic shock." Proc Natl Acad Sci U S A (2005), 102:3605-3610.
Apweiler, R., et al., "Protein sequence databases." Current opinion in chemical biology (2004), 8:76-80.
Arnaoutov, A., et al., "Crm1 is a mitotic effector of Ran-GTP in somatic cells." Nat Cell Biol (2005), 7:626-632.
Bairoch, A., et al., "Swiss-Prot: Juggling between evolution and stability" Brief Bioinform (2004), 5:39-55.
Budhu, A. S., et al., "Loading and unloading: orchestrating centrosome duplication and spindle assembly by Ran/Crml." Cell Cycle (2005), 4:1510-1514.
Chook, Y. M., et al., "Karyopherins and nuclear import." Current Opinions in Structural Biology (2001), 11:703-715.
Chook, Y. M., et al., "Uncoupling Kapb2 substrate dissociation and Ran binding." Biochemistry (2002), 41:6955-6966.
Cingolani, G., et al., "Molecular basis for the recognition of a non-classical nuclear localization signal by importin beta." Mol Cell (2002), 10:1345-1353.
Conti, E., et al., "Nucleocytoplasmic transport enters the atomic age." Curr Opin Cell Biol (2001), 13:310-319.
Cook, A., et al., "The structure of the nuclear export receptor Cse1 in its cytosolic state reveals a closed conformation incompatible with cargo binding." Mol Cell (2005), 18:355-367.

Emsley, P., et al., "Coot: model-building tools for molecular graphics," Acta Crystallogr D Biol Crystallogr (2004), 60:2126-32.
Fukuhara, N., et al., "Conformational variability of nucleo-cytoplasmic transport factors." J Biol Chem (2004), 279:176-181.
Gattiker, A., et al., "ScanProsite: a reference implementation of a Prosite scanning tool." Applied Bioinformatics (2002), 1:107-108.
Guttinger, S., et al., "Transportin2 functions as importin and mediates nuclear import of HuR." Proc Natl Acad Sci U S A (2004), 101:2918-2923.
Harel, A., et al., "Importin beta: conducting a much larger cellular symphony," Mol Cell (2004), 16:319-330.
Hase, M.E., et al., "The *Drosophila* Heterogeneous Nuclear RibonucleoproteinM Protein, HRP59, Regulates Alternative Splicing and Controls the Production of Its Own mRNA," J Biol Chem (2006), 281:39135-39141.
Iljima, M., et al., "Two motifs essential for nuclear import of the hnRNP A1 nucleocytoplasmic shuttling sequence M9 core." FEBS Lett (2006), 580:1365-1370.
Kawamura, H., et al., "Identification of the nucleocytoplasmic shuttling sequence of heterogeneous nuclear ribonucleoprotein D-like protein JKTBP and its interaction with mRNA." J Biol Chem (2002), 277:2732-2739.
Lee, S. J., et al., "The structure of importin-beta bound to SREBP-2: nuclear import of a transcription factor." Science (2003), 302:1571-1575.
Lee, S. J., et al., "Structural basis for nuclear import complex dissociaton by RanGTP." Nature (2005), 435:693-696.
Lee, B.J. et al. "Rules for Nuclear Localization Sequence Recognition by Karyopherinb2." Cell (2006), 126:543-58.
Linding, R., et al., "Protein disorder prediction: implications for structural proteomics." Structure (Camb) (2003), 11:1453-1459.
Matsuura, Y., et al., "Structural basis for the assembly of a nuclear export complex." Nature (2004), 432:872-877.
McCoy, A. J., et al., "Likelihood-enhanced fast translation functions." Acta Cryst (2005), D61:458-464.
Mosammaparast, N., and Pemberton, L. F. (2004). Karyopherins: from nuclear-transport mediators to nuclear-function regulators. Trends Cell Biol (2004), 14:547-556.
Petosa, C., et al., "Architecture of CRM1/Exportin1 suggests how cooperativity is achieved during formation of a nuclear export complex." Mol Cell (2004), 16:761-775.
Rebane, A., et al., "Transportins 1 and 2 are redundant nuclear import factors for hnRNP A1 and HuR." RNA (2004), 10, 590-599.
Smillie, D.A., et al., "Nuclear import and activity of histone deacetylase in *Xenopus* oocytes is regulated by phosphorylation." J Cell Sci (2004), 117:1857-66.

(Continued)

*Primary Examiner* — Christine J Saoud
*Assistant Examiner* — Jegatheesan Seharaseyon
(74) *Attorney, Agent, or Firm* — Edwin S. Flores; Chainey P. Singleton; Chalker Flores, LLP

(57) ABSTRACT

The present invention includes compositions, methods and kits for directing an agent across the nuclear membrane of a cell. The present invention includes a Karyopherin beta2 translocation motif in a polypeptide having a slightly positively charged region or a slightly hydrophobic region and one or more R/K/H-$X_{(2-5)}$-P-Y motifs. The polypeptide targets the agent into the cell nucleus.

7 Claims, 22 Drawing Sheets

PUBLICATIONS

Suzuki, M., et al., "Two separate regions essential for nuclear import of the hnRNP D nucleocytoplasmic shuttling sequence." Febs J 272:3975-3987, (2005).

Weis, K. "Regulating access to the genome: nucleocytoplasmic transport throughout the cell cycle." Cell (2003), 112:441-451.

Yashiroda, Y., et al., "Nucleo-Cytoplasmic Transport of Proteins as a Target for Therapeutic Drugs," M. Curr Med Chem (2003), 10:741-8.

* cited by examiner

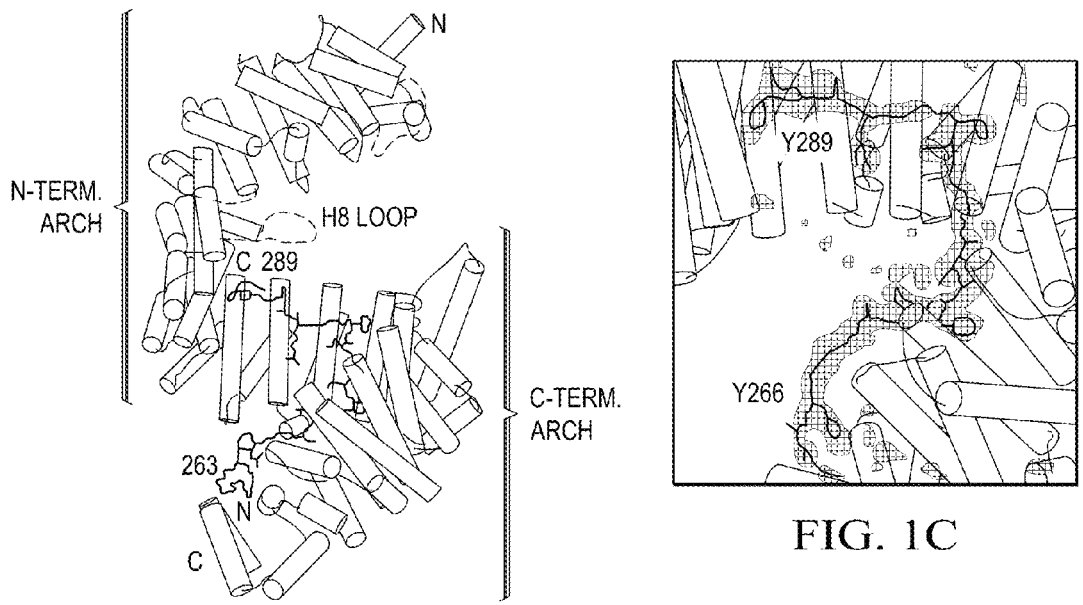
FIG. 1A
FIG. 1C
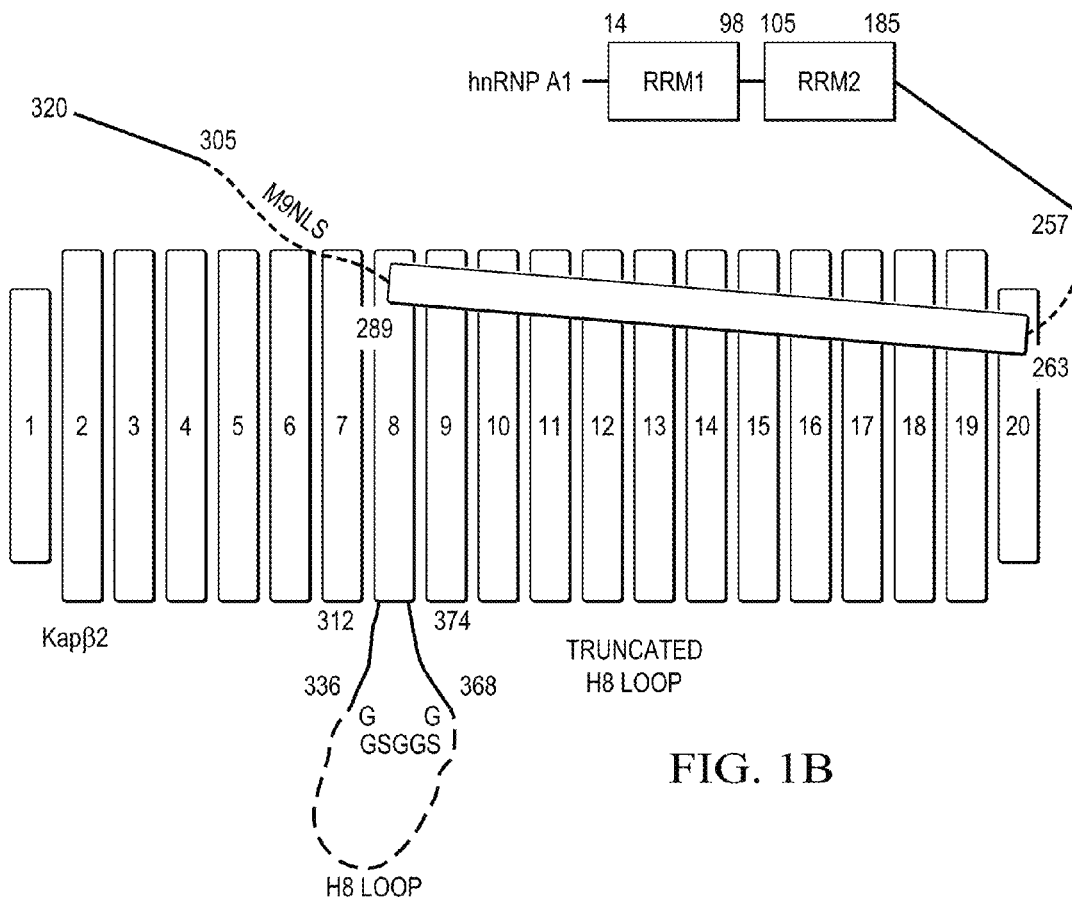
FIG. 1B

SEQUENCE LISTING

```
<160> NUMBER OF SEQ ID NOS: 137

<210> SEQ ID NO 1
<211> LENGTH: 5
<212> TYPE: PRT
<213> ORGANISM: Artificial sequence
<220> FEATURE:
<223> OTHER INFORMATION: Synthetic peptide.
<220> FEATURE:
<221> NAME/KEY: misc_feature
<222> LOCATION: (1)..(1)
<223> OTHER INFORMATION: a Arg, Lys or His residue
<220> FEATURE:
<221> NAME/KEY: misc_feature
<222> LOCATION: (2)..(3)
<223> OTHER INFORMATION: any amino acid residue

<400> SEQUENCE: 1

Xaa Xaa Xaa Pro Tyr
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic peptide.

<400> SEQUENCE: 2

Gly Gly Ser Gly Gly Ser Gly
1               5

<210> SEQ ID NO 3
<211> LENGTH: 4
<212> TYPE: PRT
<213> ORGANISM: Artificial sequence
<220> FEATURE:
<223> OTHER INFORMATION: Synthetic peptide.

<400> SEQUENCE: 3

Phe Gly Pro Met
1

<210> SEQ ID NO 4
<211> LENGTH: 5
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: is a hydrophobic residue
<220> FEATURE:
<221> NAME/KEY: MISC_FEATURE
<222> LOCATION: (3)..(3)
<223> OTHER INFORMATION: is a Pro or Lys residue
<220> FEATURE:
<221> NAME/KEY: MISC_FEATURE
```

```
<222> LOCATION: (4)..(4)
<223> OTHER INFORMATION: is a Met, Leu or Val residue
<220> FEATURE:
<221> NAME/KEY: MISC_FEATURE
<222> LOCATION: (5)..(5)
<223> OTHER INFORMATION: is a Arg or Lys residue

<400> SEQUENCE: 4

Xaa Gly Xaa Xaa Xaa
1               5

<210> SEQ ID NO 5
<211> LENGTH: 50
<212> TYPE: PRT
<213> ORGANISM: Artificial sequence
<220> FEATURE:
<223> OTHER INFORMATION: Synthetic peptide.

<400> SEQUENCE: 5

Lys His Gly Asn Asn Gln Pro Ala Arg Thr Gly Thr Leu Ser Arg Thr
1               5                   10                  15

Asn Pro Pro Thr Gln Lys Pro Pro Ser Pro Pro Met Ser Gly Arg Gly
            20                  25                  30

Thr Leu Gly Arg Asn Thr Pro Tyr Lys Thr Leu Glu Pro Val Lys Pro
        35                  40                  45

Pro Thr
    50

<210> SEQ ID NO 6
<211> LENGTH: 50
<212> TYPE: PRT
<213> ORGANISM: Artificial sequence
<220> FEATURE:
<223> OTHER INFORMATION: Synthetic peptide.

<400> SEQUENCE: 6

Gln Arg Lys Gly His Lys His Gly Lys Ser Cys Met Asn Pro Gln Lys
1               5                   10                  15

Phe Lys Phe Asp Arg Pro Ala Leu Pro Ala Asn Val Arg Lys Pro Thr
            20                  25                  30

Pro Arg Lys Pro Glu Ser Pro Tyr Gly Asn Leu Cys Asp Ala Pro Asp
        35                  40                  45

Ser Pro
    50

<210> SEQ ID NO 7
<211> LENGTH: 50
<212> TYPE: PRT
<213> ORGANISM: Artificial sequence
<220> FEATURE:
<223> OTHER INFORMATION: Synthetic peptide.

<400> SEQUENCE: 7

Pro Val Pro Pro Gly Gly Phe Gly Gln Pro Pro Ser Ala Gln Gln Pro
1               5                   10                  15

Val Pro Pro Tyr Gly Met Tyr Pro Pro Gly Gly Asn Pro Pro Ser
            20                  25                  30

Arg Met Pro Ser Tyr Pro Pro Tyr Gly Ala Pro Val Pro Gly Gln
        35                  40                  45

Pro Met
    50

<210> SEQ ID NO 8
```

-continued

```
<211> LENGTH: 50
<212> TYPE: PRT
<213> ORGANISM: Artificial sequence
<220> FEATURE:
<223> OTHER INFORMATION: Synthetic peptide.

<400> SEQUENCE: 8

Thr Leu Arg Lys Asn Gln Ser Ser Glu Asp Ile Leu Arg Asp Ala Gln
1               5                   10                  15

Val Ala Asn Lys Asn Val Ala Lys Val Pro Pro Val Pro Thr Lys
                20                  25                  30

Pro Lys Gln Ile Asn Leu Pro Tyr Phe Gly Gln Thr Asn Gln Pro Pro
        35                  40                  45

Ser Asp
    50

<210> SEQ ID NO 9
<211> LENGTH: 50
<212> TYPE: PRT
<213> ORGANISM: Artificial sequence
<220> FEATURE:
<223> OTHER INFORMATION: Synthetic peptide.

<400> SEQUENCE: 9

Gly Glu Tyr Arg Asp Tyr Asp Arg Asn Arg Arg Glu Arg Phe Ser Pro
1               5                   10                  15

Pro Arg His Glu Leu Ser Pro Pro Gln Lys Arg Met Arg Arg Asp Trp
                20                  25                  30

Asp Glu His Ser Ser Asp Pro Tyr His Ser Gly Tyr Glu Met Pro Tyr
        35                  40                  45

Ala Gly
    50

<210> SEQ ID NO 10
<211> LENGTH: 45
<212> TYPE: PRT
<213> ORGANISM: Artificial sequence
<220> FEATURE:
<223> OTHER INFORMATION: Synthetic peptide.

<400> SEQUENCE: 10

Glu Gly Met Leu Ala Asn Leu Val Glu Gln Asn Ile Ser Val Arg Arg
1               5                   10                  15

Arg Gln Gly Val Ser Ile Gly Arg Leu His Lys Gln Arg Lys Pro Asp
                20                  25                  30

Arg Arg Lys Arg Ser Arg Pro Tyr Lys Ala Lys Arg Gln
        35                  40                  45

<210> SEQ ID NO 11
<211> LENGTH: 50
<212> TYPE: PRT
<213> ORGANISM: Artificial sequence
<220> FEATURE:
<223> OTHER INFORMATION: Synthetic peptide.

<400> SEQUENCE: 11

Val Pro Ala Pro Gln Ala Pro Pro Pro Pro Lys Ala Leu Tyr Pro
1               5                   10                  15

Gly Ala Leu Gly Arg Pro Pro Met Pro Met Asn Phe Asp Pro
                20                  25                  30

Arg Trp Met Met Ile Pro Pro Tyr Val Asp Pro Arg Leu Leu Gln Gly
        35                  40                  45
```

Arg Pro
    50

<210> SEQ ID NO 12
<211> LENGTH: 50
<212> TYPE: PRT
<213> ORGANISM: Artificial sequence
<220> FEATURE:
<223> OTHER INFORMATION: Synthetic peptide.

<400> SEQUENCE: 12

Thr Ser Thr Leu Cys Pro Pro Ala Asn Pro His Pro Gln Phe Gly Gly
1               5                   10                  15

Ala Leu Ser Leu Pro Ser Thr His Ser Cys Asp Arg Tyr Pro Thr Leu
            20                  25                  30

Arg Ser His Arg Ser Ser Pro Tyr Pro Ser Pro Tyr Ala His Arg Asn
        35                  40                  45

Asn Ser
    50

<210> SEQ ID NO 13
<211> LENGTH: 51
<212> TYPE: PRT
<213> ORGANISM: Artificial sequence
<220> FEATURE:
<223> OTHER INFORMATION: Synthetic peptide.

<400> SEQUENCE: 13

Gln Gly Gln Gln Pro Pro His Pro Pro Gly Gln Gln Pro Pro Pro Pro
1               5                   10                  15

Pro Gln Pro Ala Lys Pro Gln Gln Val Ile Gln His His His Ser Pro
            20                  25                  30

Arg His His Lys Ser Asp Pro Tyr Ser Thr Gly His Leu Arg Glu Ala
        35                  40                  45

Pro Ser Pro
    50

<210> SEQ ID NO 14
<211> LENGTH: 50
<212> TYPE: PRT
<213> ORGANISM: Artificial sequence
<220> FEATURE:
<223> OTHER INFORMATION: Synthetic peptide.

<400> SEQUENCE: 14

Tyr Glu Arg Gly Gly Asp Val Ser Pro Ser Pro Tyr Ser Ser Ser Ser
1               5                   10                  15

Trp Arg Arg Ser Arg Ser Pro Tyr Ser Pro Val Leu Arg Arg Ser Gly
            20                  25                  30

Lys Ser Arg Ser Arg Ser Pro Tyr Ser Arg His Ser Arg Ser Arg
        35                  40                  45

Ser Arg
    50

<210> SEQ ID NO 15
<211> LENGTH: 50
<212> TYPE: PRT
<213> ORGANISM: Artificial sequence
<220> FEATURE:
<223> OTHER INFORMATION: Synthetic peptide.

<400> SEQUENCE: 15

Ser Ser Asn Tyr Asp Ser Tyr Lys Lys Ser Pro Gly Ser Thr Ser Arg

```
                1               5                   10                  15
Arg Gln Ser Val Ser Pro Pro Tyr Lys Glu Pro Ser Ala Tyr Gln Ser
                    20                  25                  30

Ser Thr Arg Ser Pro Ser Pro Tyr Ser Arg Arg Gln Arg Ser Val Ser
            35                  40                  45

Pro Tyr
    50

<210> SEQ ID NO 16
<211> LENGTH: 50
<212> TYPE: PRT
<213> ORGANISM: Artificial sequence
<220> FEATURE:
<223> OTHER INFORMATION: Synthetic peptide.

<400> SEQUENCE: 16

Ile Asp Ser Lys Asp Ala Ile Ile Leu His Gln Phe Ala Arg Pro Asn
1               5                   10                  15

Asn Gly Val Pro Ser Leu Ser Pro Phe Cys Leu Lys Met Glu Thr Tyr
                    20                  25                  30

Leu Arg Met Ala Asp Leu Pro Tyr Gln Asn Tyr Phe Gly Gly Lys Leu
            35                  40                  45

Ser Ala
    50

<210> SEQ ID NO 17
<211> LENGTH: 50
<212> TYPE: PRT
<213> ORGANISM: Artificial sequence
<220> FEATURE:
<223> OTHER INFORMATION: Synthetic peptide.

<400> SEQUENCE: 17

Tyr Arg Trp Lys Arg Arg Arg Ser Tyr Ser Arg Glu His Glu Gly Arg
1               5                   10                  15

Leu Arg Tyr Pro Ser Arg Arg Glu Pro Pro Pro Arg Arg Ser Arg Ser
                    20                  25                  30

Arg Ser His Asp Arg Leu Pro Tyr Gln Arg Arg Tyr Arg Glu Arg Arg
            35                  40                  45

Asp Ser
    50

<210> SEQ ID NO 18
<211> LENGTH: 50
<212> TYPE: PRT
<213> ORGANISM: Artificial sequence
<220> FEATURE:
<223> OTHER INFORMATION: Synthetic peptide.

<400> SEQUENCE: 18

Met Gly Leu Pro Gly Pro Lys Gly Ser Asn Gly Asp Pro Gly Lys Pro
1               5                   10                  15

Gly Glu Ala Gly Asn Pro Gly Val Pro Gly Gln Arg Gly Ala Pro Gly
                    20                  25                  30

Lys Asp Gly Lys Val Gly Pro Tyr Gly Pro Pro Gly Pro Pro Gly Leu
            35                  40                  45

Arg Gly
    50

<210> SEQ ID NO 19
<211> LENGTH: 50
```

```
<212> TYPE: PRT
<213> ORGANISM: Artificial sequence
<220> FEATURE:
<223> OTHER INFORMATION: Synthetic peptide.

<400> SEQUENCE: 19

Gly Tyr Gly Ser Pro Gly Leu Gln Gly Glu Pro Gly Leu Pro Gly Pro
1               5                   10                  15

Pro Gly Pro Ser Ala Val Gly Lys Pro Gly Val Pro Gly Leu Pro Gly
            20                  25                  30

Lys Pro Gly Glu Arg Gly Pro Tyr Gly Pro Lys Gly Asp Val Gly Pro
        35                  40                  45

Ala Gly
    50

<210> SEQ ID NO 20
<211> LENGTH: 40
<212> TYPE: PRT
<213> ORGANISM: Artificial sequence
<220> FEATURE:
<223> OTHER INFORMATION: Synthetic peptide.

<400> SEQUENCE: 20

Thr Trp Gln Thr Arg Asn His Thr Arg Thr Gly His Ala Tyr Pro Arg
1               5                   10                  15

Phe Thr Arg Pro Ser Phe Pro Ser Cys Asn Arg Asn Gly Lys Arg Arg
            20                  25                  30

Lys Leu Arg Leu Gly Leu Pro Tyr
        35                  40

<210> SEQ ID NO 21
<211> LENGTH: 50
<212> TYPE: PRT
<213> ORGANISM: Artificial sequence
<220> FEATURE:
<223> OTHER INFORMATION: Synthetic peptide.

<400> SEQUENCE: 21

Pro Pro Gly Thr Val Phe Gly Ala Ser Pro Asp Tyr Phe Ser Pro Arg
1               5                   10                  15

Asp Val Pro Gly Pro Pro Arg Ala Pro Phe Ala Met Arg Asn Val Tyr
            20                  25                  30

Leu Pro Arg Gly Phe Leu Pro Tyr Arg Pro Pro Arg Pro Ala Phe Phe
        35                  40                  45

Pro Gln
    50

<210> SEQ ID NO 22
<211> LENGTH: 41
<212> TYPE: PRT
<213> ORGANISM: Artificial sequence
<220> FEATURE:
<223> OTHER INFORMATION: Synthetic peptide.

<400> SEQUENCE: 22

Gly Ala Ala Phe Arg Asp Arg Arg Lys Arg Thr Pro Met Pro Lys Asp
1               5                   10                  15

Val Arg Gln Ser Leu Ser Pro Met Ser Gln Arg Pro Val Leu Lys Val
            20                  25                  30

Cys Asn His Gly Asn Lys Pro Tyr Leu
        35                  40
```

<210> SEQ ID NO 23
<211> LENGTH: 50
<212> TYPE: PRT
<213> ORGANISM: Artificial sequence
<220> FEATURE:
<223> OTHER INFORMATION: Synthetic peptide.

<400> SEQUENCE: 23

```
Cys Leu His Ser Ala Gly His Ser Gln Pro Asp Gly Ala Tyr Ser Ser
1               5                   10                  15

Ala Ser Ser Phe Ser Arg Pro Leu Gly Tyr Pro Tyr Val Asn Ser Val
            20                  25                  30

Ser Ser His Ala Ser Ser Pro Tyr Ile Ser Ser Val Gln Ser Tyr Pro
        35                  40                  45

Gly Ser
    50
```

<210> SEQ ID NO 24
<211> LENGTH: 43
<212> TYPE: PRT
<213> ORGANISM: Artificial sequence
<220> FEATURE:
<223> OTHER INFORMATION: Synthetic peptide.

<400> SEQUENCE: 24

```
Arg Gln Leu Ile Asp Tyr Glu Arg Gln Leu Phe Gly Lys Ser Thr Val
1               5                   10                  15

Lys Met Val Gln Thr Pro Tyr Gly Ile Val Pro Asp Val Tyr Glu Lys
            20                  25                  30

Glu Ser Arg His Leu Met Pro Tyr Trp Gly Ile
        35                  40
```

<210> SEQ ID NO 25
<211> LENGTH: 50
<212> TYPE: PRT
<213> ORGANISM: Artificial sequence
<220> FEATURE:
<223> OTHER INFORMATION: Synthetic peptide.

<400> SEQUENCE: 25

```
Pro Pro Ala Arg Ala Pro Thr Ala Ser Ala Asp Ala Glu Leu Ser Ala
1               5                   10                  15

Gln Leu Ser Arg Arg Leu Asp Ile Asn Glu Gly Ala Ala Arg Pro Arg
            20                  25                  30

Arg Cys Arg Val Phe Asn Pro Tyr Thr Glu Phe Pro Glu Phe Ser Arg
        35                  40                  45

Arg Leu
    50
```

<210> SEQ ID NO 26
<211> LENGTH: 50
<212> TYPE: PRT
<213> ORGANISM: Artificial sequence
<220> FEATURE:
<223> OTHER INFORMATION: Synthetic peptide.

<400> SEQUENCE: 26

```
Ser Ser Glu Leu Glu Ala Leu Glu Asn Gly Lys Arg Ser Thr Leu Ile
1               5                   10                  15

Ser Ser Asp Gly Val Ser Lys Lys Ser Glu Val Lys Asp Leu Gly Pro
            20                  25                  30

Leu Glu Ile His Leu Val Pro Tyr Thr Pro Lys Phe Pro Thr Pro Lys
        35                  40                  45
```

Pro Arg
    50

<210> SEQ ID NO 27
<211> LENGTH: 50
<212> TYPE: PRT
<213> ORGANISM: Artificial
<220> FEATURE:
<223> OTHER INFORMATION: Synthetic peptide.

<400> SEQUENCE: 27

Pro Ala Val Pro Leu Leu Leu Pro Pro Ala Leu Ala Glu Thr Val Gly
1               5                   10                  15

Pro Ala Pro Pro Gly Val Leu Arg Cys Ala Leu Gly Asp Arg Gly Arg
            20                  25                  30

Val Arg Gly Arg Ala Ala Pro Tyr Cys Val Ala Glu Leu Ala Thr Gly
        35                  40                  45

Pro Ser
    50

<210> SEQ ID NO 28
<211> LENGTH: 50
<212> TYPE: PRT
<213> ORGANISM: Artificial sequence
<220> FEATURE:
<223> OTHER INFORMATION: Synthetic peptide.

<400> SEQUENCE: 28

Pro Gly Pro His Gly Pro Pro Gly Pro Pro Gly Pro Gly Thr Pro Met
1               5                   10                  15

Gly Pro Tyr Asn Pro Ala Pro Tyr Asn Pro Gly Pro Pro Gly Pro Ala
            20                  25                  30

Pro His Gly Pro Pro Ala Pro Tyr Ala Pro Gln Gly Trp Gly Asn Ala
        35                  40                  45

Tyr Pro
    50

<210> SEQ ID NO 29
<211> LENGTH: 50
<212> TYPE: PRT
<213> ORGANISM: Artificial sequence
<220> FEATURE:
<223> OTHER INFORMATION: Synthetic peptide.

<400> SEQUENCE: 29

Leu Thr Ala Val Asp Ala Gly Ala Glu Arg Phe Ala Pro Ser Ala Pro
1               5                   10                  15

Ser Pro His His Ile Ser Pro Arg Arg Val Pro Ala Pro Ser Ser Ile
            20                  25                  30

Leu Gln Arg Thr Gln Pro Pro Tyr Thr Gln Gln Pro Ser Gly Ser His
        35                  40                  45

Leu Lys
    50

<210> SEQ ID NO 30
<211> LENGTH: 50
<212> TYPE: PRT
<213> ORGANISM: Artificial sequence
<220> FEATURE:
<223> OTHER INFORMATION: Synthetic peptide.

<400> SEQUENCE: 30

```
Ser Pro Ala Lys Ile Val Leu Arg Arg His Leu Ser Gln Asp His Thr
1               5                   10                  15

Val Pro Gly Arg Pro Ala Ala Ser Glu Leu His Ser Arg Ala Glu His
            20                  25                  30

Thr Lys Glu Asn Gly Leu Pro Tyr Gln Ser Pro Ser Val Pro Gly Ser
        35                  40                  45

Met Lys
    50

<210> SEQ ID NO 31
<211> LENGTH: 50
<212> TYPE: PRT
<213> ORGANISM: Artificial sequence
<220> FEATURE:
<223> OTHER INFORMATION: Synthetic peptide.

<400> SEQUENCE: 31

Ala Gly Val Ala Ser Cys Leu Arg Pro Ser Leu Pro Asp Gly Lys Arg
1               5                   10                  15

Cys Pro Cys Ser Pro Gly Arg Pro Ala Val Gly Gly Pro Gly Glu
            20                  25                  30

Ala Arg Lys Lys Arg Lys Pro Tyr Thr Lys Gln Gln Ile Ala Glu Leu
        35                  40                  45

Glu Asn
    50

<210> SEQ ID NO 32
<211> LENGTH: 50
<212> TYPE: PRT
<213> ORGANISM: Artificial sequence
<220> FEATURE:
<223> OTHER INFORMATION: Synthetic peptide.

<400> SEQUENCE: 32

Cys Lys Ile Gly Ser Glu Arg Ser Leu Val Leu Asp Arg Leu Ala Ser
1               5                   10                  15

Asn Val Ala Lys Arg Lys Ser Ser Met Pro Gln Lys Phe Leu Gly Asp
            20                  25                  30

Lys Gly Leu Ser Asp Thr Pro Tyr Asp Ser Ser Ala Ser Tyr Glu Lys
        35                  40                  45

Glu Asn
    50

<210> SEQ ID NO 33
<211> LENGTH: 50
<212> TYPE: PRT
<213> ORGANISM: Artificial sequence
<220> FEATURE:
<223> OTHER INFORMATION: Synthetic peptide.

<400> SEQUENCE: 33

Gly Lys Phe Val Leu Lys Ala Ser Leu Ser Ala Pro Gly Ser Glu Tyr
1               5                   10                  15

Gly Ser Pro Ser Val Ile Ser Val Ser Lys Gly Ser Pro Asp Gly Ser
            20                  25                  30

His Pro Val Val Val Ala Pro Tyr Asn Gly Gly Pro Pro Arg Thr Cys
        35                  40                  45

Pro Lys
    50

<210> SEQ ID NO 34
```

```
<211> LENGTH: 50
<212> TYPE: PRT
<213> ORGANISM: Artificial sequence
<220> FEATURE:
<223> OTHER INFORMATION: Synthetic peptide.

<400> SEQUENCE: 34

Asn Val Asn Gln Ala Phe Thr Arg Pro Pro Pro Tyr Pro Gly Asn
1               5                   10                  15

Ile Arg Ser Pro Val Ala Pro Pro Leu Gly Pro Arg Tyr Ala Val Phe
            20                  25                  30

Pro Lys Asp Gln Arg Gly Pro Tyr Pro Pro Asp Val Ala Ser Met Gly
        35                  40                  45

Met Arg
    50

<210> SEQ ID NO 35
<211> LENGTH: 42
<212> TYPE: PRT
<213> ORGANISM: Artificial sequence
<220> FEATURE:
<223> OTHER INFORMATION: Synthetic peptide.

<400> SEQUENCE: 35

Gly Ala Pro Ser Gln Gln Gln Pro Met Leu Ser Gly Val Gln Met Ala
1               5                   10                  15

Gln Ala Gly Gln Pro Gly Lys Met Pro Ser Gly Ile Lys Thr Asn Ile
            20                  25                  30

Lys Ser Ala Ser Met His Pro Tyr Gln Arg
        35                  40

<210> SEQ ID NO 36
<211> LENGTH: 50
<212> TYPE: PRT
<213> ORGANISM: Artificial sequence
<220> FEATURE:
<223> OTHER INFORMATION: Synthetic peptide.

<400> SEQUENCE: 36

Asp Leu Leu His His Pro Asn Pro Gly Ser Ile Thr His Leu Asn Tyr
1               5                   10                  15

Arg Gln Gly Ser Ile Gly Leu Tyr Thr Gln Asn Gln Pro Leu Pro Ala
            20                  25                  30

Gly Gly Pro Arg Val Asp Pro Tyr Arg Pro Val Arg Leu Pro Met Gln
        35                  40                  45

Lys Leu
    50

<210> SEQ ID NO 37
<211> LENGTH: 50
<212> TYPE: PRT
<213> ORGANISM: Artificial sequence
<220> FEATURE:
<223> OTHER INFORMATION: Synthetic peptide.

<400> SEQUENCE: 37

Leu Pro Arg Val Thr Ser Val His Leu Pro Asp Tyr Ala His Tyr Tyr
1               5                   10                  15

Thr Ile Gly Pro Gly Met Phe Pro Ser Ser Gln Ile Pro Ser Trp Lys
            20                  25                  30

Asp Trp Ala Lys Pro Gly Pro Tyr Asp Gln Pro Leu Val Asn Thr Leu
        35                  40                  45
```

Gln Arg
    50

<210> SEQ ID NO 38
<211> LENGTH: 50
<212> TYPE: PRT
<213> ORGANISM: Artificial sequence
<220> FEATURE:
<223> OTHER INFORMATION: Synthetic peptide.

<400> SEQUENCE: 38

Gly Ala Ala Gln Gln Gly Leu Thr Asp Ser Cys Gln Ser Gly Gly Val
1               5                   10                  15

Pro Thr Ala Val Gln Asn Leu Ala Pro Arg Ala Ala Val Ala Ala Ala
            20                  25                  30

Ala Pro Arg Ala Val Ala Pro Tyr Lys Tyr Ala Ser Val Arg Ser
        35                  40                  45

Pro His
    50

<210> SEQ ID NO 39
<211> LENGTH: 50
<212> TYPE: PRT
<213> ORGANISM: Artificial sequence
<220> FEATURE:
<223> OTHER INFORMATION: Synthetic peptide.

<400> SEQUENCE: 39

Val Val Tyr Lys Leu Pro Phe Gly Arg Ser Cys Thr Ala Gln Gln Pro
1               5                   10                  15

Ala Thr Thr Leu Pro Glu Asp Arg Phe Gly Tyr Arg Asp Asp His Tyr
            20                  25                  30

Gln Tyr Asp Arg Ser Gly Pro Tyr Gly Tyr Arg Gly Ile Gly Gly Met
        35                  40                  45

Lys Pro
    50

<210> SEQ ID NO 40
<211> LENGTH: 50
<212> TYPE: PRT
<213> ORGANISM: Artificial sequence
<220> FEATURE:
<223> OTHER INFORMATION: Synthetic peptide.

<400> SEQUENCE: 40

Pro Thr Met Ser Pro Leu Ala Ser Pro Ser Pro Pro His Tyr
1               5                   10                  15

Gln Arg Val Pro Leu Ser His Gly Tyr Ser Lys Leu Arg Ser Ser Ala
            20                  25                  30

Glu Gln Met His Pro Ala Pro Tyr Glu Ala Arg Gln Pro Leu Val Gln
        35                  40                  45

Pro Glu
    50

<210> SEQ ID NO 41
<211> LENGTH: 50
<212> TYPE: PRT
<213> ORGANISM: Artificial sequence
<220> FEATURE:
<223> OTHER INFORMATION: Synthetic peptide.

<400> SEQUENCE: 41

Ser His Tyr Ser Ser Ala Gln Gly Gly Ser Gln His Tyr Gln Gly Gln

```
                1               5                  10                 15
Ser Ser Ile Ala Met Met Gly Gln Gly Ser Gln Gly Ser Met Met
                        20                 25                 30

Gly Gln Arg Pro Met Ala Pro Tyr Arg Pro Ser Gln Gln Gly Ser Ser
            35                 40                 45

Gln Gln
    50

<210> SEQ ID NO 42
<211> LENGTH: 50
<212> TYPE: PRT
<213> ORGANISM: Artificial sequence
<220> FEATURE:
<223> OTHER INFORMATION: Synthetic peptide.

<400> SEQUENCE: 42

Gln Gln Gln His Gly Gln Asn Pro Gln Gln Ala His Gln Ser Gly
1               5                  10                 15

Gly Pro Gly Leu Ala Pro Leu Gly Ala Ala Gly His Pro Gly Met Met
            20                 25                 30

Pro His Gln Gln Pro Pro Tyr Pro Leu Met His His Gln Met Pro
            35                 40                 45

Pro Pro
    50

<210> SEQ ID NO 43
<211> LENGTH: 50
<212> TYPE: PRT
<213> ORGANISM: Artificial sequence
<220> FEATURE:
<223> OTHER INFORMATION: Synthetic peptide.

<400> SEQUENCE: 43

Ala Val Gln Gly Gly Gly Ala Thr Pro Val Val Gly Ala Val Gln Gly
1               5                  10                 15

Pro Val Pro Gly Met Pro Pro Met Thr Gln Ala Pro Arg Ile Met His
            20                 25                 30

His Met Pro Gly Gln Pro Pro Tyr Met Pro Pro Pro Gly Met Ile Pro
            35                 40                 45

Pro Pro
    50

<210> SEQ ID NO 44
<211> LENGTH: 50
<212> TYPE: PRT
<213> ORGANISM: Artificial sequence
<220> FEATURE:
<223> OTHER INFORMATION: Synthetic peptide.

<400> SEQUENCE: 44

Gly Gln Asp Pro Tyr Arg Leu Gly His Asp Pro Tyr Arg Leu Thr Pro
1               5                  10                 15

Asp Pro Tyr Arg Met Ser Pro Arg Pro Tyr Arg Ile Ala Pro Arg Ser
            20                 25                 30

Tyr Arg Ile Ala Pro Arg Pro Tyr Arg Leu Ala Pro Arg Pro Leu Met
            35                 40                 45

Leu Ala
    50

<210> SEQ ID NO 45
<211> LENGTH: 50
```

```
<212> TYPE: PRT
<213> ORGANISM: Artificial
<220> FEATURE:
<223> OTHER INFORMATION: Synthesized.

<400> SEQUENCE: 45

Gly Gly Ser Ser Ala His Ser Gln Asp Gly Ser His Gln Pro Val Phe
1               5                   10                  15

Ile Ser Lys Val His Thr Ser Val Asp Gly Leu Gln Gly Ile Tyr Pro
            20                  25                  30

Arg Val Gly Met Ala His Pro Tyr Glu Ser Trp Phe Lys Pro Ser His
        35                  40                  45

Pro Gly
    50

<210> SEQ ID NO 46
<211> LENGTH: 50
<212> TYPE: PRT
<213> ORGANISM: Artificial sequence
<220> FEATURE:
<223> OTHER INFORMATION: Synthetic peptide.

<400> SEQUENCE: 46

Gln Tyr Asn Met Pro Gln Gly Gly Gln His Tyr Gln Gly Gln Gln
1               5                   10                  15

Pro Pro Met Gly Met Met Gly Gln Val Asn Gln Gly Asn His Met Met
            20                  25                  30

Gly Gln Arg Gln Ile Pro Pro Tyr Arg Pro Gln Gln Gly Pro Pro
        35                  40                  45

Gln Gln
    50

<210> SEQ ID NO 47
<211> LENGTH: 50
<212> TYPE: PRT
<213> ORGANISM: Artificial sequence
<220> FEATURE:
<223> OTHER INFORMATION: Synthetic peptide.

<400> SEQUENCE: 47

Pro Ser Tyr Pro Leu Ala Ala Leu Lys Ser Gln Pro Ser Ala Gln
1               5                   10                  15

Pro Ser Lys Met Gly Lys Lys Lys Gly Lys Lys Pro Leu Asn Ala Leu
            20                  25                  30

Asp Val Met Lys His Gln Pro Tyr Gln Leu Asn Ala Ser Leu Phe Thr
        35                  40                  45

Phe Gln
    50

<210> SEQ ID NO 48
<211> LENGTH: 50
<212> TYPE: PRT
<213> ORGANISM: Artificial sequence
<220> FEATURE:
<223> OTHER INFORMATION: Synthetic peptide.

<400> SEQUENCE: 48

Gly Val Val Arg Asp Val Ala Lys Met Leu Pro Thr Leu Gly Gly Glu
1               5                   10                  15

Glu Gly Val Ser Arg Ile Tyr Ala Asp Pro Thr Lys Arg Leu Glu Leu
            20                  25                  30

Tyr Phe Arg Pro Lys Asp Pro Tyr Cys His Pro Val Cys Ala Asn Arg
```

Phe Ser
    50

<210> SEQ ID NO 49
<211> LENGTH: 50
<212> TYPE: PRT
<213> ORGANISM: Artificial sequence
<220> FEATURE:
<223> OTHER INFORMATION: Synthetic peptide.

<400> SEQUENCE: 49

Lys Ser Ile Met Lys Lys Ser Pro Phe Ser Gly Pro Thr Asp Pro Arg
1               5                   10                  15

Pro Pro Arg Arg Ile Ala Val Pro Ser Arg Ser Ser Ala Ser Val
        20                  25                  30

Pro Lys Pro Ala Pro Gln Pro Tyr Pro Phe Thr Ser Ser Leu Ser Thr
        35                  40                  45

Ile Asn
    50

<210> SEQ ID NO 50
<211> LENGTH: 50
<212> TYPE: PRT
<213> ORGANISM: Artificial
<220> FEATURE:
<223> OTHER INFORMATION: Synthesized.

<400> SEQUENCE: 50

Leu Pro Met Gly Ser Arg Val Leu Gln Ile Arg Pro Asn Leu Thr Asn
1               5                   10                  15

Lys Leu Arg Pro Ile Ala Pro Lys Trp Lys Val Met Pro Leu Val Ser
        20                  25                  30

Met Pro Thr His Leu Ala Pro Tyr Thr Gln Val Lys Lys Glu Ser Glu
        35                  40                  45

Asp Lys
    50

<210> SEQ ID NO 51
<211> LENGTH: 50
<212> TYPE: PRT
<213> ORGANISM: Artificial sequence
<220> FEATURE:
<223> OTHER INFORMATION: Synthetic peptide.

<400> SEQUENCE: 51

Pro Ala Ala Thr Ser Gln Gly Cys Pro Gly Pro Pro Gly Ser Pro Asp
1               5                   10                  15

Lys Pro Ser Arg Pro His Gly Leu Val Pro Ala Gly Trp Gly Met Gly
        20                  25                  30

Pro Arg Ala Gly Glu Gly Pro Tyr Val Ser Glu Gln Glu Leu Gln Lys
        35                  40                  45

Leu Phe
    50

<210> SEQ ID NO 52
<211> LENGTH: 50
<212> TYPE: PRT
<213> ORGANISM: Artificial sequence
<220> FEATURE:
<223> OTHER INFORMATION: Synthetic peptide.

<400> SEQUENCE: 52

```
Gly Pro Gly Gly Gly Trp Gly Ser Gly Ser Ser Phe Arg Gly Thr
1               5                   10                  15

Pro Gly Gly Gly Pro Arg Pro Ser Pro Arg Asp Gly Tyr Gly
            20                  25                  30

Ser Pro His His Thr Pro Pro Tyr Gly Pro Arg Ser Arg Pro Tyr Gly
            35                  40                  45

Ser Ser
    50

<210> SEQ ID NO 53
<211> LENGTH: 50
<212> TYPE: PRT
<213> ORGANISM: Artificial sequence
<220> FEATURE:
<223> OTHER INFORMATION: Synthetic peptide.

<400> SEQUENCE: 53

Phe Val Trp Gly Phe Ser Phe Ser Gly Ala Leu Gly Val Pro Ser Phe
1               5                   10                  15

Val Val Pro Ser Ser Gly Pro Gly Pro Arg Ala Gly Ala Arg Pro Arg
            20                  25                  30

Arg Arg Ile Gln Pro Val Pro Tyr Arg Leu Glu Leu Asp Gln Lys Ile
            35                  40                  45

Ser Ser
    50

<210> SEQ ID NO 54
<211> LENGTH: 50
<212> TYPE: PRT
<213> ORGANISM: Artificial sequence
<220> FEATURE:
<223> OTHER INFORMATION: Synthetic peptide.

<400> SEQUENCE: 54

Val His Phe Ser Gly Gln Phe Thr Gly Thr Ala Gly Ala Cys Arg Tyr
1               5                   10                  15

Gly Pro Phe Gly Pro Pro Pro Ser Gln Ala Ser Ser Gly Gln Ala
            20                  25                  30

Arg Met Phe Pro Asn Ala Pro Tyr Leu Pro Ser Cys Leu Glu Ser Gln
            35                  40                  45

Pro Ala
    50

<210> SEQ ID NO 55
<211> LENGTH: 50
<212> TYPE: PRT
<213> ORGANISM: Artificial sequence
<220> FEATURE:
<223> OTHER INFORMATION: Synthetic peptide.

<400> SEQUENCE: 55

Ile Ser Cys Trp Ala Phe Trp Thr Thr Trp Thr Gln Ser Cys Ser Ser
1               5                   10                  15

Asn Ala Leu Pro Gln Ser Leu Pro Ala Trp Arg Ser Ser Gln Arg Ser
            20                  25                  30

Thr Gln Lys Asp Pro Val Pro Tyr Gln Pro Pro Phe Leu Cys Gln Trp
            35                  40                  45

Gly Arg
    50
```

```
<210> SEQ ID NO 56
<211> LENGTH: 50
<212> TYPE: PRT
<213> ORGANISM: Artificial sequence
<220> FEATURE:
<223> OTHER INFORMATION: Synthetic peptide.

<400> SEQUENCE: 56

His Ala Ile Asp His Arg Leu Ser Ile Ser Lys Lys Thr Ala Asn Gly
1               5                   10                  15

Gly Leu Lys Pro Ser Val Tyr Pro Tyr Lys Leu Tyr Arg Leu Leu Pro
                20                  25                  30

Met Lys Cys Lys Arg Ala Pro Tyr Lys Ser Tyr Arg Asn Ser Ser Tyr
            35                  40                  45

Glu Asn
    50

<210> SEQ ID NO 57
<211> LENGTH: 50
<212> TYPE: PRT
<213> ORGANISM: Artificial sequence
<220> FEATURE:
<223> OTHER INFORMATION: Synthetic peptide.

<400> SEQUENCE: 57

Val Lys Pro Pro Ala Thr Ala Thr Pro Ala Ser Leu Pro Lys Phe Asn
1               5                   10                  15

Leu Leu Leu Gly Lys Val Asp Asp Gly Thr Gly Arg Glu Ala Pro Lys
                20                  25                  30

Arg Glu Ala Pro Ala Phe Pro Tyr Pro Thr Ala Thr Leu Ala Ser Gly
            35                  40                  45

Pro Gln
    50

<210> SEQ ID NO 58
<211> LENGTH: 50
<212> TYPE: PRT
<213> ORGANISM: Artificial sequence
<220> FEATURE:
<223> OTHER INFORMATION: Synthetic peptide.

<400> SEQUENCE: 58

Gly Ser Val Lys Arg Val Ser Glu Asn Asn Gly Asn Gly Lys Asn Ser
1               5                   10                  15

Ser His Thr His Glu Leu Gly Thr Lys Arg Glu Asn Lys Lys Thr Ile
                20                  25                  30

Phe Lys Val Asn Lys Asp Pro Tyr Val Ala Asp Met Glu Asn Gly Asn
            35                  40                  45

Ile Glu
    50

<210> SEQ ID NO 59
<211> LENGTH: 50
<212> TYPE: PRT
<213> ORGANISM: Artificial sequence
<220> FEATURE:
<223> OTHER INFORMATION: Synthetic peptide.

<400> SEQUENCE: 59

Asn Arg Arg Glu Arg Phe Ser Pro Pro Arg His Glu Leu Ser Pro Pro
1               5                   10                  15

Gln Lys Arg Met Arg Arg Asp Trp Asp Glu His Ser Ser Asp Pro Tyr
                20                  25                  30
```

```
His Ser Gly Tyr Glu Met Pro Tyr Ala Gly Gly Gly Gly Pro Thr
        35                  40                  45
Tyr Gly
    50

<210> SEQ ID NO 60
<211> LENGTH: 45
<212> TYPE: PRT
<213> ORGANISM: Artificial sequence
<220> FEATURE:
<223> OTHER INFORMATION: Synthetic peptide.

<400> SEQUENCE: 60

Glu Gly Met Leu Ala Asn Leu Val Glu Gln Asn Ile Ser Val Arg Arg
1               5                   10                  15

Arg Gln Gly Val Ser Ile Gly Arg Leu His Lys Gln Arg Lys Pro Asp
            20                  25                  30

Arg Arg Lys Arg Ser Arg Pro Tyr Lys Ala Lys Arg Gln
        35                  40                  45

<210> SEQ ID NO 61
<211> LENGTH: 50
<212> TYPE: PRT
<213> ORGANISM: Artificial sequence
<220> FEATURE:
<223> OTHER INFORMATION: Synthetic peptide.

<400> SEQUENCE: 61

Lys Arg Tyr Ser Ser Arg Ser Arg Ser Arg Thr Tyr Ser Arg Ser Arg
1               5                   10                  15

Ser Arg Asp Arg Met Tyr Ser Arg Asp Tyr Arg Arg Asp Tyr Arg Asn
            20                  25                  30

Asn Arg Gly Met Arg Arg Pro Tyr Gly Tyr Arg Gly Arg Gly Arg Gly
        35                  40                  45

Tyr Tyr
    50

<210> SEQ ID NO 62
<211> LENGTH: 31
<212> TYPE: PRT
<213> ORGANISM: Artificial sequence
<220> FEATURE:
<223> OTHER INFORMATION: Synthetic peptide.

<400> SEQUENCE: 62

Met Arg Lys Pro Arg Arg Lys Ser Arg Gln Asn Ala Glu Gly Arg Arg
1               5                   10                  15

Ser Pro Ser Pro Tyr Ser Leu Lys Cys Ser Pro Thr Arg Glu Thr
            20                  25                  30

<210> SEQ ID NO 63
<211> LENGTH: 50
<212> TYPE: PRT
<213> ORGANISM: Artificial sequence
<220> FEATURE:
<223> OTHER INFORMATION: Synthetic peptide.

<400> SEQUENCE: 63

Ala Ser Lys Pro Ser Ser Pro Arg Glu Val Lys Ala Glu Glu Lys Ser
1               5                   10                  15

Pro Ile Ser Ile Asn Val Lys Thr Val Lys Lys Glu Pro Glu Asp Arg
            20                  25                  30
```

Gln Gln Ala Ser Lys Ser Pro Tyr Asn Gly Val Arg Lys Asp Ser Lys
        35                  40                  45

Arg Ser
    50

<210> SEQ ID NO 64
<211> LENGTH: 50
<212> TYPE: PRT
<213> ORGANISM: Artificial sequence
<220> FEATURE:
<223> OTHER INFORMATION: Synthetic peptide.

<400> SEQUENCE: 64

Gln Arg Phe Leu His Asp Pro Glu Lys Leu Asp Ser Ser Lys Ala
1               5                   10                  15

Leu Ser Phe Thr Arg Ile Arg Arg Ser Ser Phe Ser Ser Lys Asp Glu
            20                  25                  30

Lys Arg Glu Asp Arg Thr Pro Tyr Gln Leu Val Lys Lys Leu Gln Lys
        35                  40                  45

Lys Ile
    50

<210> SEQ ID NO 65
<211> LENGTH: 50
<212> TYPE: PRT
<213> ORGANISM: Artificial sequence
<220> FEATURE:
<223> OTHER INFORMATION: Synthetic peptide.

<400> SEQUENCE: 65

Arg Glu Arg Arg Asp Ser Asp Thr Tyr Arg Cys Glu Glu Arg Ser Pro
1               5                   10                  15

Ser Phe Gly Glu Asp Tyr Tyr Gly Pro Ser Arg Ser Arg His Arg Arg
            20                  25                  30

Arg Ser Arg Glu Arg Gly Pro Tyr Arg Thr Arg Lys His Ala His His
        35                  40                  45

Cys His
    50

<210> SEQ ID NO 66
<211> LENGTH: 40
<212> TYPE: PRT
<213> ORGANISM: Artificial sequence
<220> FEATURE:
<223> OTHER INFORMATION: Synthetic peptide.

<400> SEQUENCE: 66

Thr Trp Gln Thr Arg Asn His Thr Arg Thr Gly His Ala Tyr Pro Arg
1               5                   10                  15

Phe Thr Arg Pro Ser Phe Pro Ser Cys Asn Arg Asn Gly Lys Arg Arg
            20                  25                  30

Lys Leu Arg Leu Gly Leu Pro Tyr
        35                  40

<210> SEQ ID NO 67
<211> LENGTH: 50
<212> TYPE: PRT
<213> ORGANISM: Artificial sequence
<220> FEATURE:
<223> OTHER INFORMATION: Synthetic peptide.

<400> SEQUENCE: 67

Glu Asp Leu Glu Asp Asp Ile Pro Arg Arg Lys Asn Arg Ala Lys Gly

```
                1               5                  10                 15
Lys Ala Tyr Gly Ile Gly Gly Leu Arg Lys Arg Gln Asp Thr Ala Ser
                20                 25                 30

Leu Glu Asp Arg Asp Lys Pro Tyr Val Cys Asp Lys Phe Tyr Lys Glu
        35                 40                 45

Leu Ala
    50

<210> SEQ ID NO 68
<211> LENGTH: 50
<212> TYPE: PRT
<213> ORGANISM: Artificial sequence
<220> FEATURE:
<223> OTHER INFORMATION: Synthetic peptide.

<400> SEQUENCE: 68

Thr Val Lys Glu Glu Arg Gly Glu Thr Ala Ala Gly Ala Gly Val Pro
1               5                  10                 15

Gly Glu Ala Thr Gly Arg Gly Ala Gly Arg Arg Lys Arg Pro
                20                 25                 30

Leu Gln Arg Gly Lys Pro Pro Tyr Ser Tyr Ile Ala Leu Ile Ala Met
        35                 40                 45

Ala Ile
    50

<210> SEQ ID NO 69
<211> LENGTH: 50
<212> TYPE: PRT
<213> ORGANISM: Artificial sequence
<220> FEATURE:
<223> OTHER INFORMATION: Synthetic peptide.

<400> SEQUENCE: 69

Ala Glu Pro Gly Arg Glu Pro Glu Ala Ala Ala Gly Arg Gly Glu
1               5                  10                 15

Ala Ala Pro Thr Pro Ala Pro Gly Pro Gly Arg Arg Arg Arg Pro
                20                 25                 30

Leu Gln Arg Gly Lys Pro Pro Tyr Ser Tyr Ile Ala Leu Ile Ala Met
        35                 40                 45

Ala Leu
    50

<210> SEQ ID NO 70
<211> LENGTH: 36
<212> TYPE: PRT
<213> ORGANISM: Artificial sequence
<220> FEATURE:
<223> OTHER INFORMATION: Synthetic peptide.

<400> SEQUENCE: 70

Met Asp Pro Ala Ser Ser Gly Pro Ser Lys Ala Lys Lys Thr Asn Ala
1               5                  10                 15

Gly Ile Arg Arg Pro Glu Lys Pro Pro Tyr Ser Tyr Ile Ala Leu Ile
                20                 25                 30

Val Met Ala Ile
        35

<210> SEQ ID NO 71
<211> LENGTH: 46
<212> TYPE: PRT
<213> ORGANISM: Artificial sequence
<220> FEATURE:
```

<223> OTHER INFORMATION: Synthetic peptide.

<400> SEQUENCE: 71

Met Gly Pro Cys Ser Gly Ser Arg Leu Gly Pro Glu Ala Glu Ser
1               5                   10                  15

Pro Ser Gln Pro Pro Lys Arg Arg Lys Lys Arg Tyr Leu Arg His Asp
            20                  25                  30

Lys Pro Pro Tyr Thr Tyr Leu Ala Met Ile Ala Leu Val Ile
        35                  40                  45

<210> SEQ ID NO 72
<211> LENGTH: 50
<212> TYPE: PRT
<213> ORGANISM: Artificial sequence
<220> FEATURE:
<223> OTHER INFORMATION: Synthetic peptide.

<400> SEQUENCE: 72

Ser Lys Asp Asp Pro Gly Lys Gly Ser Tyr Trp Ala Ile Asp Thr Asn
1               5                   10                  15

Pro Lys Glu Asp Ala Leu Pro Thr Arg Pro Lys Lys Arg Ala Arg Ser
            20                  25                  30

Val Glu Arg Ala Ser Thr Pro Tyr Ser Ile Asp Ser Asp Ser Leu Gly
        35                  40                  45

Met Glu
    50

<210> SEQ ID NO 73
<211> LENGTH: 50
<212> TYPE: PRT
<213> ORGANISM: Artificial sequence
<220> FEATURE:
<223> OTHER INFORMATION: Synthetic peptide.

<400> SEQUENCE: 73

Met Asn Pro Cys Met Ser Pro Met Ala Tyr Ala Pro Ser Asn Leu Gly
1               5                   10                  15

Arg Ser Arg Ala Gly Gly Gly Gly Asp Ala Lys Thr Phe Lys Arg Ser
            20                  25                  30

Tyr Pro His Ala Lys Pro Pro Tyr Ser Tyr Ile Ser Leu Ile Thr Met
        35                  40                  45

Ala Ile
    50

<210> SEQ ID NO 74
<211> LENGTH: 50
<212> TYPE: PRT
<213> ORGANISM: Artificial sequence
<220> FEATURE:
<223> OTHER INFORMATION: Synthetic peptide.

<400> SEQUENCE: 74

Leu Gly Val Ser Gly Gly Ser Ser Ser Gly Tyr Gly Ala Pro Gly
1               5                   10                  15

Pro Gly Leu Val His Gly Lys Glu Met Pro Lys Gly Tyr Arg Arg Pro
            20                  25                  30

Leu Ala His Ala Lys Pro Pro Tyr Ser Tyr Ile Ser Leu Ile Thr Met
        35                  40                  45

Ala Ile
    50

```
<210> SEQ ID NO 75
<211> LENGTH: 50
<212> TYPE: PRT
<213> ORGANISM: Artificial sequence
<220> FEATURE:
<223> OTHER INFORMATION: Synthetic peptide.

<400> SEQUENCE: 75

His Glu Phe Lys Ile Lys Gly Arg Lys Ala Ser Lys Pro Ile Ser Asp
1               5                   10                  15

Ser Arg Glu Val Ser Asn Gly Ile Glu Lys Lys Gly Lys Lys Lys Ser
            20                  25                  30

Val Gly Arg Pro Pro Gly Pro Tyr Thr Arg Lys Met Ile Gln Lys Thr
        35                  40                  45

Ala Glu
    50

<210> SEQ ID NO 76
<211> LENGTH: 50
<212> TYPE: PRT
<213> ORGANISM: Artificial sequence
<220> FEATURE:
<223> OTHER INFORMATION: Synthetic peptide.

<400> SEQUENCE: 76

Pro Ser Thr Ser Pro Arg Ala Ser Val Thr Glu Glu Ser Trp Leu Gly
1               5                   10                  15

Ala Arg Ser Ser Arg Pro Ala Ser Pro Cys Asn Lys Arg Lys Tyr Ser
            20                  25                  30

Leu Asn Gly Arg Gln Pro Pro Tyr Ser Pro His His Ser Pro Thr Pro
        35                  40                  45

Ser Pro
    50

<210> SEQ ID NO 77
<211> LENGTH: 50
<212> TYPE: PRT
<213> ORGANISM: Artificial sequence
<220> FEATURE:
<223> OTHER INFORMATION: Synthetic peptide.

<400> SEQUENCE: 77

Ser Lys Phe Val Asp Ala Asp Phe Ser Asp Asn Val Cys Ser Gly Asn
1               5                   10                  15

Thr Leu His Ser Leu Asn Ser Pro Arg Thr Pro Lys Lys Pro Val Asn
            20                  25                  30

Ser Lys Leu Gly Leu Ser Pro Tyr Leu Thr Pro Tyr Asn Asp Ser Asp
        35                  40                  45

Lys Leu
    50

<210> SEQ ID NO 78
<211> LENGTH: 50
<212> TYPE: PRT
<213> ORGANISM: Artificial sequence
<220> FEATURE:
<223> OTHER INFORMATION: Synthetic peptide.

<400> SEQUENCE: 78

Gln Thr Glu Leu Pro Asp Glu Lys Ile Gly Lys Lys Arg Lys Arg Lys
1               5                   10                  15

Asp Asp Gly Glu Asn Ala Lys Pro Ile Lys Lys Ile Ile Gly Asp Gly
            20                  25                  30
```

Thr Arg Asp Pro Cys Leu Pro Tyr Ser Trp Ile Ser Pro Thr Thr Gly
            35                  40                  45

Ile Ile
    50

<210> SEQ ID NO 79
<211> LENGTH: 50
<212> TYPE: PRT
<213> ORGANISM: Artificial sequence
<220> FEATURE:
<223> OTHER INFORMATION: Synthetic peptide.

<400> SEQUENCE: 79

Tyr Arg Trp Thr Arg Asp Asp His Ser Ala Ser Arg Gln Pro Glu Tyr
1               5                   10                  15

Arg Asp Met Arg Asp Gly Phe Arg Arg Lys Ser Phe Tyr Ser Ser His
            20                  25                  30

Tyr Ala Arg Glu Arg Ser Pro Tyr Lys Arg Asp Asn Thr Phe Phe Arg
            35                  40                  45

Glu Ser
    50

<210> SEQ ID NO 80
<211> LENGTH: 50
<212> TYPE: PRT
<213> ORGANISM: Artificial sequence
<220> FEATURE:
<223> OTHER INFORMATION: Synthetic peptide.

<400> SEQUENCE: 80

Ser Arg Ser Gly Glu Arg Trp Gly Ala Asp Gly Asp Arg Gly Leu Pro
1               5                   10                  15

Lys Pro Trp Glu Glu Arg Arg Lys Arg Arg Ser Leu Ser Ser Asp Arg
            20                  25                  30

Gly Arg Thr Thr His Ser Pro Tyr Glu Glu Arg Ser Arg Thr Lys Gly
            35                  40                  45

Ser Gly
    50

<210> SEQ ID NO 81
<211> LENGTH: 50
<212> TYPE: PRT
<213> ORGANISM: Artificial sequence
<220> FEATURE:
<223> OTHER INFORMATION: Synthetic peptide.

<400> SEQUENCE: 81

Asp Arg Glu Arg Lys Lys Ser Lys Ser Arg Glu Arg Lys Arg Ser Arg
1               5                   10                  15

Ser Lys Glu Arg Arg Arg Ser Arg Ser Arg Ser Arg Asp Arg Arg Phe
            20                  25                  30

Arg Gly Arg Tyr Arg Ser Pro Tyr Ser Gly Pro Lys Phe Asn Ser Ala
            35                  40                  45

Ile Arg
    50

<210> SEQ ID NO 82
<211> LENGTH: 30
<212> TYPE: PRT
<213> ORGANISM: Artificial sequence
<220> FEATURE:
<223> OTHER INFORMATION: Synthetic peptide.

```
<400> SEQUENCE: 82

Gly Ile Ser Arg Asp Asn Trp His Lys Arg Arg Lys Thr Gly Gly Lys
1               5                   10                  15

Arg Lys Pro Tyr His Lys Lys Arg Lys Tyr Glu Leu Gly Arg
            20                  25                  30

<210> SEQ ID NO 83
<211> LENGTH: 50
<212> TYPE: PRT
<213> ORGANISM: Artificial sequence
<220> FEATURE:
<223> OTHER INFORMATION: Synthetic peptide.

<400> SEQUENCE: 83

Asp Glu Ala Lys Arg Leu Arg Ala Gln His Met Lys Glu His Pro Asp
1               5                   10                  15

Tyr Lys Tyr Arg Pro Arg Arg Lys Pro Lys Asn Leu Leu Lys Lys Asp
            20                  25                  30

Arg Tyr Val Phe Pro Leu Pro Tyr Leu Gly Asp Thr Asp Pro Leu Lys
        35                  40                  45

Ala Ala
    50

<210> SEQ ID NO 84
<211> LENGTH: 50
<212> TYPE: PRT
<213> ORGANISM: Artificial
<220> FEATURE:
<223> OTHER INFORMATION: Synthesized.

<400> SEQUENCE: 84

Asp Glu Ala Lys Arg Leu Arg Ala Met His Met Lys Glu His Pro Asp
1               5                   10                  15

Tyr Lys Tyr Arg Pro Arg Arg Lys Pro Lys Thr Leu Leu Lys Lys Asp
            20                  25                  30

Lys Phe Ala Phe Pro Val Pro Tyr Gly Leu Gly Gly Val Ala Asp Ala
        35                  40                  45

Glu His
    50

<210> SEQ ID NO 85
<211> LENGTH: 50
<212> TYPE: PRT
<213> ORGANISM: Artificial
<220> FEATURE:
<223> OTHER INFORMATION: Synthesized.

<400> SEQUENCE: 85

Gly Gly Gln Arg Gly Gly Phe Gly Ser Pro Gly Gly Ser Gly Gly
1               5                   10                  15

Met Ser Arg Gly Arg Gly Arg Arg Asp Asn Glu Leu Ile Gly Gln Thr
            20                  25                  30

Val Arg Ile Ser Gln Gly Pro Tyr Lys Gly Tyr Ile Gly Val Val Lys
        35                  40                  45

Asp Ala
    50

<210> SEQ ID NO 86
<211> LENGTH: 50
<212> TYPE: PRT
<213> ORGANISM: Artificial sequence
```

```
<220> FEATURE:
<223> OTHER INFORMATION: Synthetic peptide.

<400> SEQUENCE: 86

Pro Ser Tyr Pro Leu Ala Ala Leu Lys Ser Gln Pro Ser Ala Ala Gln
1               5                   10                  15

Pro Ser Lys Met Gly Lys Lys Gly Lys Lys Pro Leu Asn Ala Leu
                20                  25                  30

Asp Val Met Lys His Gln Pro Tyr Gln Leu Asn Ala Ser Leu Phe Thr
            35                  40                  45

Phe Gln
    50

<210> SEQ ID NO 87
<211> LENGTH: 50
<212> TYPE: PRT
<213> ORGANISM: Artificial sequence
<220> FEATURE:
<223> OTHER INFORMATION: Synthetic peptide.

<400> SEQUENCE: 87

Ala Asn Ile Asp His Lys Cys Lys Lys Asp Ile Leu Ile Gly Arg Ile
1               5                   10                  15

Lys Asn Val Glu Asp Lys Ser Trp Lys Ile Arg Pro Arg Pro Thr
                20                  25                  30

Lys Thr Asn Tyr Glu Gly Pro Tyr Tyr Ile Cys Lys Asp Val Ala Ala
            35                  40                  45

Glu Glu
    50

<210> SEQ ID NO 88
<211> LENGTH: 50
<212> TYPE: PRT
<213> ORGANISM: Artificial sequence
<220> FEATURE:
<223> OTHER INFORMATION: Synthetic peptide.

<400> SEQUENCE: 88

Arg Asp Ser Leu Glu Val Ser Val Arg Pro Gly Ser Gly Ile Ser Ala
1               5                   10                  15

Arg Pro Ser Ser Gly Thr Lys Glu Lys Gly Gly Arg Arg Asp Leu Gln
                20                  25                  30

Ile Lys Val Ser Ala Arg Pro Tyr His Leu Phe Gln Gly Pro Lys Pro
            35                  40                  45

Asp Leu
    50

<210> SEQ ID NO 89
<211> LENGTH: 50
<212> TYPE: PRT
<213> ORGANISM: Artificial sequence
<220> FEATURE:
<223> OTHER INFORMATION: Synthetic peptide.

<400> SEQUENCE: 89

Leu Thr Asp Ser Leu Asp Tyr Pro Gly Glu Arg Ala Ser Asn Gly Met
1               5                   10                  15

Ser Ser Asp Leu Pro Pro Lys Ser Lys Asp Lys Leu Asp Lys Lys
                20                  25                  30

Lys Glu Val Val Lys Pro Pro Tyr Pro Lys Ile Arg Arg Ala Ser Gly
            35                  40                  45
```

Arg Leu
    50

<210> SEQ ID NO 90
<211> LENGTH: 50
<212> TYPE: PRT
<213> ORGANISM: Artificial sequence
<220> FEATURE:
<223> OTHER INFORMATION: Synthetic peptide.

<400> SEQUENCE: 90

Arg Gly Pro Phe Ser Gln Phe Arg Tyr Glu Pro Pro Gly Asp Leu
1               5                   10                  15

Asp Gly Phe Pro Gly Val Phe Glu Gly Ala Gly Ser Arg Lys Arg Lys
            20                  25                  30

Ser Met Pro Thr Lys Met Pro Tyr Asn His Pro Ala Glu Glu Val Thr
        35                  40                  45

Leu Ala
    50

<210> SEQ ID NO 91
<211> LENGTH: 18
<212> TYPE: PRT
<213> ORGANISM: Artificial sequence
<220> FEATURE:
<223> OTHER INFORMATION: Synthetic peptide.

<400> SEQUENCE: 91

Glu Asp Gly Ile Glu Glu Glu Asp Asp Asp Asp Glu Ile Asp Asp
1               5                   10                  15

Asp Asp

<210> SEQ ID NO 92
<211> LENGTH: 12
<212> TYPE: PRT
<213> ORGANISM: Artificial sequence
<220> FEATURE:
<223> OTHER INFORMATION: Synthetic peptide.

<400> SEQUENCE: 92

Thr Gly Gly Phe Thr Phe Gly Thr Ala Lys Thr Ala
1               5                   10

<210> SEQ ID NO 93
<211> LENGTH: 16
<212> TYPE: PRT
<213> ORGANISM: Artificial
<220> FEATURE:
<223> OTHER INFORMATION: Synthesized.
<220> FEATURE:
<221> NAME/KEY: MISC_FEATURE
<222> LOCATION: (1)..(1)
<223> OTHER INFORMATION: any hydrophobic amino acid residue.
<220> FEATURE:
<221> NAME/KEY: MISC_FEATURE
<222> LOCATION: (2)..(2)
<223> OTHER INFORMATION: is a Gly, Ala or Ser reisdue.
<220> FEATURE:
<221> NAME/KEY: MISC_FEATURE
<222> LOCATION: (2)..(2)
<223> OTHER INFORMATION: is a Gly, Ala or Ser residue.
<220> FEATURE:
<221> NAME/KEY: MISC_FEATURE
<222> LOCATION: (3)..(3)
<223> OTHER INFORMATION: a hydrophobic residue, Arg or Lys residue.
<220> FEATURE:
<221> NAME/KEY: MISC_FEATURE
<222> LOCATION: (4)..(4)
<223> OTHER INFORMATION: a hydrophobic residue, Arg or Lys residue.

```
<220> FEATURE:
<221> NAME/KEY: MISC_FEATURE
<222> LOCATION: (5)..(11)
<223> OTHER INFORMATION: any amino acid residues
<220> FEATURE:
<221> NAME/KEY: MISC_FEATURE
<222> LOCATION: (12)..(12)
<223> OTHER INFORMATION: a Arg, Lys or His residue.
<220> FEATURE:
<221> NAME/KEY: MISC_FEATURE
<222> LOCATION: (13)..(14)
<223> OTHER INFORMATION: any amino acid residue.

<400> SEQUENCE: 93

Xaa Xaa Xaa Xaa Xaa Xaa Xaa Xaa Xaa Xaa Xaa Xaa Xaa Xaa Pro Tyr
1               5                   10                  15

<210> SEQ ID NO 94
<211> LENGTH: 10
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(3)
<223> OTHER INFORMATION: a Lys or Arg residue
<220> FEATURE:
<221> NAME/KEY: MISC_FEATURE
<222> LOCATION: (4)..(6)
<223> OTHER INFORMATION: any amino acid residue.
<220> FEATURE:
<221> NAME/KEY: MISC_FEATURE
<222> LOCATION: (7)..(7)
<223> OTHER INFORMATION: a Lys, His or Arg residue.
<220> FEATURE:
<221> NAME/KEY: MISC_FEATURE
<222> LOCATION: (8)..(8)
<223> OTHER INFORMATION: any amino acid residue.

<400> SEQUENCE: 94

Xaa Xaa Xaa Xaa Xaa Xaa Xaa Xaa Pro Tyr
1               5                   10

<210> SEQ ID NO 95
<211> LENGTH: 7
<212> TYPE: PRT
<213> ORGANISM: Artificial sequence
<220> FEATURE:
<223> OTHER INFORMATION: Synthetic peptide.

<400> SEQUENCE: 95

Lys Glu Lys Asn Ile Lys Arg
1               5

<210> SEQ ID NO 96
<211> LENGTH: 8
<212> TYPE: PRT
<213> ORGANISM: Artificial sequence
<220> FEATURE:
<223> OTHER INFORMATION: Synthetic peptide.

<400> SEQUENCE: 96

Lys Glu Lys Asn Ala Ala Ala Ala
1               5

<210> SEQ ID NO 97
<211> LENGTH: 17
<212> TYPE: PRT
<213> ORGANISM: Artificial sequence
<220> FEATURE:
<223> OTHER INFORMATION: Synthetic peptide.
```

```
<220> FEATURE:
<221> NAME/KEY: MISC_FEATURE
<222> LOCATION: (5)..(15)
<223> OTHER INFORMATION: X is any amino acid residue.

<400> SEQUENCE: 97

Phe Gly Pro Met Xaa Xaa Xaa Xaa Xaa Xaa Xaa Xaa Xaa Xaa Xaa Pro
1               5                   10                  15

Tyr

<210> SEQ ID NO 98
<211> LENGTH: 17
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (5)..(15)
<223> OTHER INFORMATION: X is any amino acid residue.

<400> SEQUENCE: 98

Tyr Gly Lys Val Xaa Xaa Xaa Xaa Xaa Xaa Xaa Xaa Xaa Xaa Xaa Pro
1               5                   10                  15

Tyr

<210> SEQ ID NO 99
<211> LENGTH: 17
<212> TYPE: PRT
<213> ORGANISM: Artificial sequence
<220> FEATURE:
<223> OTHER INFORMATION: Synthesized.
<220> FEATURE:
<221> NAME/KEY: MISC_FEATURE
<222> LOCATION: (5)..(15)
<223> OTHER INFORMATION: X is any amino acid residue.

<400> SEQUENCE: 99

Val Ala Met Ser Xaa Xaa Xaa Xaa Xaa Xaa Xaa Xaa Xaa Xaa Xaa Pro
1               5                   10                  15

Tyr

<210> SEQ ID NO 100
<211> LENGTH: 19
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (5)..(17)
<223> OTHER INFORMATION: X is any amino acid residue.

<400> SEQUENCE: 100

Phe Ser Pro Met Xaa Xaa Xaa Xaa Xaa Xaa Xaa Xaa Xaa Xaa Xaa Xaa
1               5                   10                  15

Xaa Pro Gly

<210> SEQ ID NO 101
<211> LENGTH: 17
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (5)..(15)
<223> OTHER INFORMATION: X is any amino acid residue.
```

```
<400> SEQUENCE: 101

Tyr Ser Asp Pro Xaa Xaa Xaa Xaa Xaa Xaa Xaa Xaa Xaa Xaa Pro
1               5                   10                  15

Tyr

<210> SEQ ID NO 102
<211> LENGTH: 18
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (5)..(16)
<223> OTHER INFORMATION: X is any amino acid residue.

<400> SEQUENCE: 102

Pro Gly Lys Met Xaa Xaa Xaa Xaa Xaa Xaa Xaa Xaa Xaa Xaa Xaa
1               5                   10                  15

Pro Tyr

<210> SEQ ID NO 103
<211> LENGTH: 20
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (5)..(18)
<223> OTHER INFORMATION: X is any amino acid residue.

<400> SEQUENCE: 103

Pro Ser Leu Lys Xaa Xaa Xaa Xaa Xaa Xaa Xaa Xaa Xaa Xaa Xaa
1               5                   10                  15

Xaa Xaa Pro Tyr
            20

<210> SEQ ID NO 104
<211> LENGTH: 19
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (5)..(17)
<223> OTHER INFORMATION: X is any amino acid residue.

<400> SEQUENCE: 104

Pro Gly Lys Met Xaa Xaa Xaa Xaa Xaa Xaa Xaa Xaa Xaa Xaa Xaa
1               5                   10                  15

Xaa Pro Tyr

<210> SEQ ID NO 105
<211> LENGTH: 15
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (5)..(13)
<223> OTHER INFORMATION: X is any amino acid residue.

<400> SEQUENCE: 105
```

```
Arg Gly Pro Pro Xaa Xaa Xaa Xaa Xaa Xaa Xaa Xaa Pro Tyr
1               5                   10                  15
```

<210> SEQ ID NO 106
<211> LENGTH: 17
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (5)..(15)
<223> OTHER INFORMATION: X is any amino acid residue.

<400> SEQUENCE: 106

```
Gln Gly Val Gln Xaa Xaa Xaa Xaa Xaa Xaa Xaa Xaa Xaa Xaa Pro
1               5                   10                  15

Tyr
```

<210> SEQ ID NO 107
<211> LENGTH: 17
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (6)..(15)
<223> OTHER INFORMATION: X is any amino acid residue.

<400> SEQUENCE: 107

```
Lys Arg Lys Glu Lys Xaa Xaa Xaa Xaa Xaa Xaa Xaa Xaa Xaa Pro
1               5                   10                  15

Tyr
```

<210> SEQ ID NO 108
<211> LENGTH: 18
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (9)..(16)
<223> OTHER INFORMATION: X is any amino acid residue.

<400> SEQUENCE: 108

```
Arg Glu Glu Gly Lys Glu Arg Xaa Xaa Xaa Xaa Xaa Xaa Xaa Xaa
1               5                   10                  15

Pro Tyr
```

<210> SEQ ID NO 109
<211> LENGTH: 18
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (8)..(16)
<223> OTHER INFORMATION: X is any amino acid residue.

<400> SEQUENCE: 109

```
Lys Lys Lys His Arg Arg Xaa Xaa Xaa Xaa Xaa Xaa Xaa Xaa Xaa
1               5                   10                  15

Pro Tyr
```

```
<210> SEQ ID NO 110
<211> LENGTH: 18
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (9)..(16)
<223> OTHER INFORMATION: X is any amino acid residue.

<400> SEQUENCE: 110

Arg Arg Pro Tyr Arg Arg Arg Xaa Xaa Xaa Xaa Xaa Xaa Xaa
1               5                   10                  15

Pro Tyr

<210> SEQ ID NO 111
<211> LENGTH: 27
<212> TYPE: PRT
<213> ORGANISM: Artificial
<220> FEATURE:
<223> OTHER INFORMATION: Synthesized.

<400> SEQUENCE: 111

Phe Gly Asn Tyr Asn Asn Gln Ser Ser Asn Phe Gly Pro Met Lys Gly
1               5                   10                  15

Gly Asn Phe Gly Gly Arg Ser Ser Gly Pro Tyr
            20                  25

<210> SEQ ID NO 112
<211> LENGTH: 27
<212> TYPE: PRT
<213> ORGANISM: Artificial
<220> FEATURE:
<223> OTHER INFORMATION: Synthesized.

<400> SEQUENCE: 112

Tyr Gly Asp Tyr Ser Asn Gln Gln Ser Gly Tyr Gly Lys Val Ser Arg
1               5                   10                  15

Arg Gly Gly His Gln Asn Ser Tyr Lys Pro Tyr
            20                  25

<210> SEQ ID NO 113
<211> LENGTH: 27
<212> TYPE: PRT
<213> ORGANISM: Artificial
<220> FEATURE:
<223> OTHER INFORMATION: Synthesized.

<400> SEQUENCE: 113

Ser Ser Arg Leu Glu Glu Asp Gly Asp Val Ala Met Ser Asp Ala
1               5                   10                  15

Gln Asp Gly Pro Arg Val Arg Tyr Asn Pro Tyr
            20                  25

<210> SEQ ID NO 114
<211> LENGTH: 27
<212> TYPE: PRT
<213> ORGANISM: Artificial
<220> FEATURE:
<223> OTHER INFORMATION: Synthesized.

<400> SEQUENCE: 114

His His Gln Ala Gln Arg Phe Arg Phe Ser Pro Met Gly Val Asp His
1               5                   10                  15

Met Ser Gly Leu Ser Gly Val Asn Val Pro Gly
```

<210> SEQ ID NO 115
<211> LENGTH: 27
<212> TYPE: PRT
<213> ORGANISM: Artificial
<220> FEATURE:
<223> OTHER INFORMATION: Synthesized.

<400> SEQUENCE: 115

Phe Lys Ser Ser Gln Glu Glu Val Arg Ser Tyr Ser Asp Pro Pro Leu
1               5                   10                  15

Lys Phe Met Ser Val Gln Arg Pro Gly Pro Tyr
            20                  25

<210> SEQ ID NO 116
<211> LENGTH: 27
<212> TYPE: PRT
<213> ORGANISM: Artificial
<220> FEATURE:
<223> OTHER INFORMATION: Synthesized.

<400> SEQUENCE: 116

Gly Glu Gly Glu Arg Pro Ala Gln Asn Glu Lys Arg Lys Glu Lys Asn
1               5                   10                  15

Ile Lys Arg Gly Gly Asn Arg Phe Glu Pro Tyr
            20                  25

<210> SEQ ID NO 117
<211> LENGTH: 27
<212> TYPE: PRT
<213> ORGANISM: Artificial sequence
<220> FEATURE:
<223> OTHER INFORMATION: Synthetic peptide.

<400> SEQUENCE: 117

Arg Asp Arg Gly Tyr Asp Lys Ala Asp Arg Glu Glu Gly Lys Glu Arg
1               5                   10                  15

Arg His His Arg Arg Glu Glu Leu Ala Pro Tyr
            20                  25

<210> SEQ ID NO 118
<211> LENGTH: 29
<212> TYPE: PRT
<213> ORGANISM: Artificial sequence
<220> FEATURE:
<223> OTHER INFORMATION: Synthetic peptide.

<400> SEQUENCE: 118

Gln Met Gly Gly Arg Arg Gly Gly Arg Gly Gly Pro Gly Lys Asn Asp
1               5                   10                  15

Lys Gly Glu His Arg Gln Glu Arg Arg Asp Arg Pro Tyr
            20                  25

<210> SEQ ID NO 119
<211> LENGTH: 29
<212> TYPE: PRT
<213> ORGANISM: Artificial
<220> FEATURE:
<223> OTHER INFORMATION: Synthesized.

<400> SEQUENCE: 119

Gly Gln Asp Asp Trp Asn Gly Thr Arg Pro Ser Leu Lys Ala Pro Pro
1               5                   10                  15

Ala Arg Pro Val Lys Gly Ala Tyr Arg Glu His Pro Tyr

```
                            20                  25

<210> SEQ ID NO 120
<211> LENGTH: 29
<212> TYPE: PRT
<213> ORGANISM: Artificial sequence
<220> FEATURE:
<223> OTHER INFORMATION: Synthetic peptide.

<400> SEQUENCE: 120

Arg Gly Gly Gly Asp Arg Gly Phe Gly Pro Gly Lys Met Asp Ser
1               5                   10                  15

Arg Gly Glu His Arg Gln Asp Arg Arg Glu Arg Pro Tyr
            20                  25

<210> SEQ ID NO 121
<211> LENGTH: 29
<212> TYPE: PRT
<213> ORGANISM: Artificial sequence
<220> FEATURE:
<223> OTHER INFORMATION: Synthetic peptide.

<400> SEQUENCE: 121

Phe Pro Pro Pro Thr Asn Ser Gly Met Pro Thr Ser Asp Ser Arg Gly
1               5                   10                  15

Pro Pro Pro Thr Asp Pro Tyr Gly Arg Pro Pro Pro Tyr
            20                  25

<210> SEQ ID NO 122
<211> LENGTH: 28
<212> TYPE: PRT
<213> ORGANISM: Artificial sequence
<220> FEATURE:
<223> OTHER INFORMATION: Synthetic peptide.

<400> SEQUENCE: 122

Asp Thr Val Asn Met Leu His Ser Leu Leu Ser Ala Gln Val Gln Pro
1               5                   10                  15

Thr Gln Pro Thr Ala Phe Glu Phe Val Arg Pro Tyr
            20                  25

<210> SEQ ID NO 123
<211> LENGTH: 28
<212> TYPE: PRT
<213> ORGANISM: Artificial sequence
<220> FEATURE:
<223> OTHER INFORMATION: Synthetic peptide.

<400> SEQUENCE: 123

Glu Glu Trp Gly Gln Gln Gln Arg Gln Leu Gly Lys Lys Lys His Arg
1               5                   10                  15

Arg Arg Pro Ser Lys Lys Lys Arg His Lys Pro Tyr
            20                  25

<210> SEQ ID NO 124
<211> LENGTH: 29
<212> TYPE: PRT
<213> ORGANISM: Artificial sequence
<220> FEATURE:
<223> OTHER INFORMATION: Synthetic peptide.

<400> SEQUENCE: 124

Ser Glu Ser Ala Pro Glu Gly Gln Ala Gln Gln Arg Arg Pro Tyr Arg
1               5                   10                  15

Arg Arg Arg Phe Pro Pro Tyr Tyr Met Arg Arg Pro Tyr
```

-continued

```
                20                  25

<210> SEQ ID NO 125
<211> LENGTH: 63
<212> TYPE: PRT
<213> ORGANISM: Artificial sequence
<220> FEATURE:
<223> OTHER INFORMATION: Synthetic peptide.

<400> SEQUENCE: 125

Ser Asp Ile Asp Ile Ile Leu Leu Lys Gly Asp Val Glu Glu Asp Glu
1               5                   10                  15

Thr Ile Pro Asp Ser Glu Gln Asp Ile Arg Pro Arg Arg Phe His Arg
            20                  25                  30

Ser Arg Thr Val Ala Gln Gln His Asp Glu Asp Gly Ile Glu Glu Glu
        35                  40                  45

Asp Asp Asp Asp Asp Glu Ile Asp Asp Asp Asp Thr Ile Ser Asp
    50                  55                  60

<210> SEQ ID NO 126
<211> LENGTH: 27
<212> TYPE: PRT
<213> ORGANISM: Artificial sequence
<220> FEATURE:
<223> OTHER INFORMATION: Synthetic peptide.

<400> SEQUENCE: 126

Glu Arg Pro Ala Gln Asn Glu Lys Arg Lys Glu Lys Asn Gly Gly Asn
1               5                   10                  15

Arg Phe Glu Pro Tyr Ala Asn Pro Thr Lys Arg
            20                  25

<210> SEQ ID NO 127
<211> LENGTH: 33
<212> TYPE: PRT
<213> ORGANISM: Artificial sequence
<220> FEATURE:
<223> OTHER INFORMATION: Synthetic peptide.

<400> SEQUENCE: 127

Phe Gly Asn Tyr Asn Asn Gln Ser Ser Asn Phe Gly Pro Met Lys Gly
1               5                   10                  15

Gly Asn Phe Gly Gly Arg Ser Ser Gly Pro Tyr Gly Gly Gly Gly Gln
            20                  25                  30

Tyr

<210> SEQ ID NO 128
<211> LENGTH: 38
<212> TYPE: PRT
<213> ORGANISM: Artificial sequence
<220> FEATURE:
<223> OTHER INFORMATION: Synthetic peptide.

<400> SEQUENCE: 128

Gly Gly Ser Tyr Asn Asp Phe Gly Asn Tyr Asn Asn Gln Ser Ser Asn
1               5                   10                  15

Phe Gly Pro Met Lys Gly Gly Asn Phe Gly Gly Arg Phe Glu Pro Tyr
            20                  25                  30

Ala Asn Pro Thr Lys Arg
        35

<210> SEQ ID NO 129
<211> LENGTH: 6
```

```
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: a Arg, Lys or His residue.
<220> FEATURE:
<221> NAME/KEY: MISC_FEATURE
<222> LOCATION: (2)..(4)
<223> OTHER INFORMATION: any amino acid residue.

<400> SEQUENCE: 129

Xaa Xaa Xaa Xaa Pro Tyr
1               5

<210> SEQ ID NO 130
<211> LENGTH: 7
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: a Arg, Lys, or His residue.
<220> FEATURE:
<221> NAME/KEY: MISC_FEATURE
<222> LOCATION: (2)..(5)
<223> OTHER INFORMATION: any amino acid residue.

<400> SEQUENCE: 130

Xaa Xaa Xaa Xaa Xaa Pro Tyr
1               5

<210> SEQ ID NO 131
<211> LENGTH: 8
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: a Arg, Lys or His residue.
<220> FEATURE:
<221> NAME/KEY: MISC_FEATURE
<222> LOCATION: (2)..(6)
<223> OTHER INFORMATION: any amino acid residue.

<400> SEQUENCE: 131

Xaa Xaa Xaa Xaa Xaa Xaa Pro Tyr
1               5

<210> SEQ ID NO 132
<211> LENGTH: 24
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: any hydrophobic amino acid residue.
<220> FEATURE:
<221> NAME/KEY: MISC_FEATURE
<222> LOCATION: (2)..(2)
<223> OTHER INFORMATION: a Gly, Ser or Ala residue.
<220> FEATURE:
<221> NAME/KEY: MISC_FEATURE
<222> LOCATION: (3)..(4)
<223> OTHER INFORMATION: a hydrophobic residue, Arg or Lys residue.
<220> FEATURE:
```

```
<221> NAME/KEY: MISC_FEATURE
<222> LOCATION: (5)..(16)
<223> OTHER INFORMATION: any amino acid residue.
<220> FEATURE:
<221> NAME/KEY: MISC_FEATURE
<222> LOCATION: (17)..(17)
<223> OTHER INFORMATION: a Arg, Lys or His residue.
<220> FEATURE:
<221> NAME/KEY: MISC_FEATURE
<222> LOCATION: (18)..(22)
<223> OTHER INFORMATION: any amino acid residue.

<400> SEQUENCE: 132

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Tyr
            20

<210> SEQ ID NO 133
<211> LENGTH: 21
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(3)
<223> OTHER INFORMATION: A Lys or Arg residue.
<220> FEATURE:
<221> NAME/KEY: MISC_FEATURE
<222> LOCATION: (4)..(13)
<223> OTHER INFORMATION: any amino acid residue.
<220> FEATURE:
<221> NAME/KEY: MISC_FEATURE
<222> LOCATION: (14)..(14)
<223> OTHER INFORMATION: a Lys, His or Arg residue.
<220> FEATURE:
<221> NAME/KEY: MISC_FEATURE
<222> LOCATION: (15)..(19)
<223> OTHER INFORMATION: any amino acid residue.

<400> SEQUENCE: 133

Xaa Xaa Xaa Xaa Xaa Xaa Xaa Xaa Xaa Xaa Xaa Xaa Xaa Xaa Xaa Xaa
1               5                   10                  15

Xaa Xaa Xaa Pro Tyr
            20

<210> SEQ ID NO 134
<211> LENGTH: 11
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: a Lys or Arg residue.
<220> FEATURE:
<221> NAME/KEY: MISC_FEATURE
<222> LOCATION: (2)..(2)
<223> OTHER INFORMATION: any amino acid residue.
<220> FEATURE:
<221> NAME/KEY: MISC_FEATURE
<222> LOCATION: (3)..(4)
<223> OTHER INFORMATION: a Lys or Arg residue.
<220> FEATURE:
<221> NAME/KEY: MISC_FEATURE
<222> LOCATION: (5)..(7)
<223> OTHER INFORMATION: any amino acid residue.
<220> FEATURE:
<221> NAME/KEY: MISC_FEATURE
<222> LOCATION: (8)..(8)
<223> OTHER INFORMATION: a Lys, His or Arg residue.
<220> FEATURE:
```

```
<221> NAME/KEY: MISC_FEATURE
<222> LOCATION: (9)..(9)
<223> OTHER INFORMATION: any amin acid residue.
<220> FEATURE:
<221> NAME/KEY: MISC_FEATURE
<222> LOCATION: (9)..(9)
<223> OTHER INFORMATION: any amino acid residue.

<400> SEQUENCE: 134

Xaa Xaa Xaa Xaa Xaa Xaa Xaa Xaa Xaa Pro Tyr
1               5                   10

<210> SEQ ID NO 135
<211> LENGTH: 12
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: a Lys or Arg residue.
<220> FEATURE:
<221> NAME/KEY: MISC_FEATURE
<222> LOCATION: (2)..(3)
<223> OTHER INFORMATION: any amino acid residue.
<220> FEATURE:
<221> NAME/KEY: MISC_FEATURE
<222> LOCATION: (4)..(5)
<223> OTHER INFORMATION: a Lys or Arg residue.
<220> FEATURE:
<221> NAME/KEY: MISC_FEATURE
<222> LOCATION: (6)..(8)
<223> OTHER INFORMATION: any amino acid residue.
<220> FEATURE:
<221> NAME/KEY: MISC_FEATURE
<222> LOCATION: (9)..(9)
<223> OTHER INFORMATION: a Lys, His or Arg residue.
<220> FEATURE:
<221> NAME/KEY: MISC_FEATURE
<222> LOCATION: (10)..(10)
<223> OTHER INFORMATION: any amino acid residue.

<400> SEQUENCE: 135

Xaa Xaa Xaa Xaa Xaa Xaa Xaa Xaa Xaa Xaa Pro Tyr
1               5                   10

<210> SEQ ID NO 136
<211> LENGTH: 22
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: a Lys or Arg residue.
<220> FEATURE:
<221> NAME/KEY: MISC_FEATURE
<222> LOCATION: (2)..(2)
<223> OTHER INFORMATION: any amino acid residue.
<220> FEATURE:
<221> NAME/KEY: MISC_FEATURE
<222> LOCATION: (3)..(4)
<223> OTHER INFORMATION: a Lys or Arg residue.
<220> FEATURE:
<221> NAME/KEY: MISC_FEATURE
<222> LOCATION: (5)..(14)
<223> OTHER INFORMATION: any amino acid residue.
<220> FEATURE:
<221> NAME/KEY: MISC_FEATURE
<222> LOCATION: (15)..(15)
<223> OTHER INFORMATION: a Lys, His or Arg residue.
<220> FEATURE:
<221> NAME/KEY: MISC_FEATURE
<222> LOCATION: (16)..(20)
```

<223> OTHER INFORMATION: any amino acid residue.

<400> SEQUENCE: 136

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Pro Tyr
            20

<210> SEQ ID NO 137
<211> LENGTH: 23
<212> TYPE: PRT
<213> ORGANISM: Artificial sequence
<220> FEATURE:
<223> OTHER INFORMATION: Synthetic peptide.
<220> FEATURE:
<221> NAME/KEY: MISC_FEATURE
<222> LOCATION: (1)..(1)
<223> OTHER INFORMATION: a Lys or Arg residue.
<220> FEATURE:
<221> NAME/KEY: MISC_FEATURE
<222> LOCATION: (2)..(3)
<223> OTHER INFORMATION: any amino acid residue.
<220> FEATURE:
<221> NAME/KEY: MISC_FEATURE
<222> LOCATION: (4)..(5)
<223> OTHER INFORMATION: a Lys or Arg residue.
<220> FEATURE:
<221> NAME/KEY: MISC_FEATURE
<222> LOCATION: (6)..(15)
<223> OTHER INFORMATION: any amino acid residue.
<220> FEATURE:
<221> NAME/KEY: MISC_FEATURE
<222> LOCATION: (16)..(16)
<223> OTHER INFORMATION: a Lys, His or Arg residue.
<220> FEATURE:
<221> NAME/KEY: MISC_FEATURE
<222> LOCATION: (17)..(21)
<223> OTHER INFORMATION: any amino acid residue.

<400> SEQUENCE: 137

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Pro Tyr
            20
```

US 8,470,976 B2

METHODS AND COMPOSITIONS FOR TARGETING MACROMOLECULES INTO THE NUCLEUS

CROSS-REFERENCE TO RELATED APPLICATIONS

This application is a continuation-in-part of and claims priority to U.S. Provisional Application Ser. No. 60/814,127, filed Jun. 17, 2006, the contents of which is incorporated by reference herein in its entirety.

STATEMENT OF FEDERALLY FUNDED RESEARCH

This invention was made with U.S. Government support under Contract No. R01 GM069909 awarded by the NIH and contract W-31-109-ENG-38 awarded by the United States Department of Energy. The government has certain rights in this invention.

TECHNICAL FIELD OF THE INVENTION

The present invention relates to a method for transferring, and more specifically directing an agent across a biological membrane of a cell using a polypeptide that includes a novel nuclear localization sequence.

BACKGROUND OF THE INVENTION

Without limiting the scope of the invention, its background is described in connection with the transport of an agent across a membrane.

The transport of exogenous material across a biological membrane into host cells and into the cell nucleus is usually limited by the rate of the uptake of the genetic material introduced into the cells. Generally, the exogenous material diffuses through the cell; however, exogenous material may be degraded by the cell or not allowed to pass the nuclear membrane into the nucleus of the cell.

SUMMARY OF THE INVENTION

The present inventors recognized a need for a composition and a method of using and identifying compositions that provide transport through the nuclear membrane. Therefore, the present invention provides a method of non-viral gene delivery across a cell membrane, e.g., the nuclear membrane. In addition, the present inventors recognized a need for an improvement in DNA transfer technology, gene delivery and therapeutic compositions. The present inventors also recognized that current methods for nuclear delivery use targeting sequences that include a number of basic residues that, most often, are electrostatically-masked by negatively charged DNA, thus reducing the efficiency of nuclear targeting in the cell. The present inventors also recognized that cytoplasmic sequestration is a major obstacle to nuclear uptake. The present invention provides PY-NLSs compositions that are longer and significantly more complex signals that interact specifically with Kap β2/Transportin, and less likely to bind non-specifically and contribute to cytoplasmic sequestration. The present invention provides for an improvement in transfer by using a composition that is tethered to provide an increase in uptake of molecules (DNA, RNA proteins or any therapeutics) into the nucleus.

The present invention provides a chimeric membrane localization polypeptide that localizes an agent to a membrane, e.g., a nuclear membrane. The chimeric membrane localization polypeptide includes at least a portion of the N-terminus of hnRNP A1-NLS fused to at least a portion of the C-terminal of hnRNP M-NLS. The chimeric polypeptide is capable of localization to the nuclear membrane of a cell. In addition, the chimeric polypeptide is capable of transporting an agent into the nucleus through the nuclear membrane.

The present invention also provides a chimeric polypeptide that localizes an agent about a cellular membrane. The chimeric polypeptide includes at least a portion of the C-terminal of hnRNP M-NLS fused to at lease a portion of the N-terminus of hnRNP A1-NLS and one or more agents associated with the portion of the C-terminal of hnRNP M-NLS, the portion of the N-terminus of hnRNP A1-NLS or both. The chimeric polypeptide is capable of transporting the one or more agents about a cellular membrane.

The present invention also includes a translocation agent that modifies the localization of one or more agents about a membrane and includes at least a portion of the N-terminus of hnRNP A1-NLS fused to at least a portion of the C-terminal half of hnRNP M-NLS. A chimeric polypeptide is formed with the ability to affect transport of one or more agents about a nuclear membrane.

The present invention includes a method of localizing an agent about a cellular membrane by contacting one or more cells with at least a portion of a membrane localization fusion protein. The membrane localization fusion protein comprises one or more agents associated with, at least a portion of the N-terminus of hnRNP A1-NLS fused to at least a portion of the C-terminal of hnRNP M-NLS; wherein the membrane localization fusion protein is capable of localization to the nuclear membrane of a cell.

A method of improving gene delivery across a cellular membrane is also provided by the present invention that includes associating a nucleic acid with at least a portion of a membrane localization fusion protein and contacting one or more cells with the membrane localization fusion protein, wherein the nucleic acid is positioned about the nuclear membrane of the cell. The membrane localization fusion protein includes at least a portion of the N-terminus of hnRNP A1-NLS fused to at least a portion of the C-terminal of hnRNP M-NLS and is capable of localization about a nuclear membrane of a cell.

The present invention also includes a kit having a fusion protein to localize an agent about a nuclear membrane. The fusion protein includes at least a portion of a N-terminal of hnRNP A1-NLS fused to at least a portion of the C-terminal of hnRNP M-NLS and an agent binding motif.

The invention provides numerous examples of peptides of varying lengths, e.g., about 30 to 40 amino acids, that target macromolecules into the nucleus. This group of peptides are described herein as PY-Nuclear Localization Signals "PY-NLSs", which bind to and are transported into the nucleus by nuclear transport factors, e.g., Karyopherin beta2 (Kap β2, also known as Transportin). The present invention also provides a method for identifying the PY-NLS nuclear targeting sequences and/or domains. In addition, the present invention includes numerous NLS that have similarities to many new PY-NLSs in nuclear proteins. The nuclear membrane remains the major barrier in delivery of DNA, genes and other therapeutics in nonviral DNA transfer technology and gene therapy. Nuclear uptake of DNA can be enhanced when tethered to a PY-NLS. However, only one class of general well-defined NLS (the classic basic-NLS) is known and thus used in DNA transfer technology. The present invention provides numerous PY-NLSs that are entirely distinct in sequence and chemical properties.

The present invention provides an isolated and purified polypeptide that translocates an agent across a nuclear membrane. The polypeptide includes a Karyopherin beta2 translocation motif having a peptide with a slightly positively charged region or a slightly hydrophobic region and one or more R/K/H-X$_{(2-5)}$-P-Y motifs (SEQ ID NO: 1) (hence, the PY-NLS), whereby the peptide targets an agent into the cell nucleus.

The present invention also provides a structurally disordered polypeptide having a Karyopherin beta2 translocation motif with a peptide comprising a slightly positively charged region or a slightly hydrophobic region and one or more R/K/H-X$_{(2-5)}$-P-Y motifs (SEQ ID NO: 1). The peptide is translocated by Karyopherin beta2 into the cell nucleus.

Furthermore, the present invention includes a method of transporting an agent across a cellular membrane by attaching an agent to a Karyopherin beta2 translocation motif comprising a peptide having a slightly positively charged region or a slightly hydrophobic region and one or more R/K/H-X$_{(2-5)}$-P-Y motifs (SEQ ID NO: 1) and contacting one or more cells with the agent attached to the Karyopherin beta2 translocation motif The peptide is translocated by Karyopherin beta2 into the cell nucleus.

In addition, the present invention includes a nuclear targeting polypeptide. The nuclear targeting polypeptide includes an amino-terminal positively charged region or a hydrophobic region and one or more carboxy-terminal R/K/H-X$_{(2-5)}$-P-Y motifs (SEQ ID NO: 1). An agent binding motif may also be included.

A method of improving gene delivery across a cellular membrane is also provided by the present invention. The method includes attaching a molecule for nuclear targeting, e.g., a nucleic acid molecule, to a polypeptide that includes a Karyopherin beta2 translocation motif, e.g., a peptide with a slightly positively charged or a slightly hydrophobic amino region and one or more R/K/H-X$_{(2-5)}$-P-Y motifs carboxy from the slightly positively charged or a slightly hydrophobic amino region. The polypeptide is translocated by Karyopherin beta2 into the cell nucleus.

In addition, the present invention includes a kit of agent transfer across a cellular membrane having a Karyopherin beta2 translocation motif that includes a polypeptide having a slightly positively charged region or a slightly hydrophobic region and one or more R/K/H-X$_{(2-5)}$-P-Y motifs (SEQ ID NO: 1). The peptide is translocated by Karyopherin beta2 into the cell nucleus. In some instances, the Karyopherin beta2 translocation motif includes at least a portion of a fusion protein. The kit may also include an agent binding motif for binding one or more nucleic acids, PNAs, drugs, pharmaceutical agents, isotopes, heavy metals, nano-particles, lipids, carbohydrates, proteins, amino acids, vitamins, polymers, detectable labels, polypeptides that translocates an agent nuclear membranes and combinations thereof.

The present invention provides numerous compositions that have a high affinity (e.g., KD about 40 nM) and are specific for nuclear transport pathways (e.g., the Kap β2 nuclear transport pathway). The present invention also provides a method of using and identifying PY-NLSs.

The present inventors recognized the need for a specific nuclear import inhibitor for use as a proteomic analyses to map the extensive nuclear traffic.

Kapβ2/Transportin recognizes PY-Nuclear localization signal (here after referred to as "NLS"), a new class of NLS with a R/H/KX$_{(2-5)}$PY motif (SEQ ID NO: 1). PY-NLSs can be subdivided into hydrophobic(h)PY- and basic(b)PY-NLSs based on the composition of an additional N-terminal motif. Kapβ2 complexes with bPY- and hPY-NLSs show structural convergence only at consensus motifs, explaining ligand diversity. The present invention provides a nuclear localization agent designed a Kapβ2-specific nuclear import inhibitor, M9M.

BRIEF DESCRIPTION OF THE DRAWINGS

For a more complete understanding of the features and advantages of the present invention, reference is now made to the detailed description of the invention along with the accompanying figures and in which:

FIGS. 1A-1C are images of the crystal structure of the Kapβ2-M9NLS complex;

DETAILED DESCRIPTION OF THE INVENTION

Figure 2A:
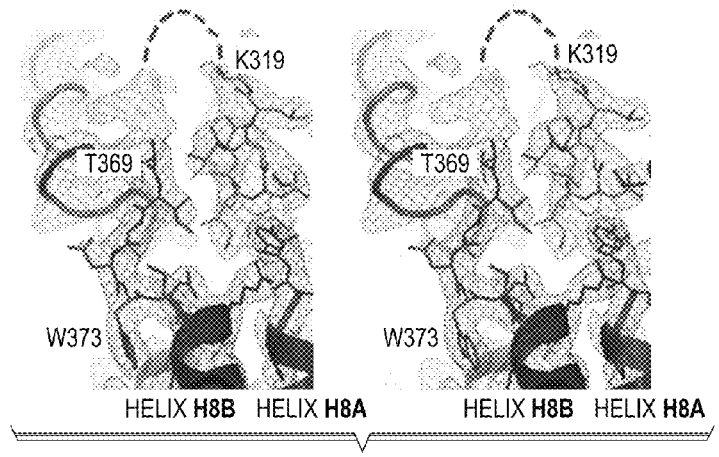
FIGS. 2A-2C are stereo diagrams and gel images of Kapβ complex.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims. As used herein the terms "protein", "polypeptide" or "peptide" refer to compounds comprising amino acids joined via peptide bonds and are used interchangeably.

The present invention provides a chimeric membrane localization polypeptide that localizes an agent to a nuclear membrane. The chimeric membrane localization polypeptide includes at least a portion of the N-terminus of hnRNP A1-NLS fused to at least a portion of the C-terminal of hnRNP M-NLS. The chimeric polypeptide is capable of localization to the nuclear membrane of a cell. The chimeric membrane localization polypeptide generally has a KD affinity for Karyopherin beta2 of between about 0.1 and 10 nanomolar, e.g., about 100 picomolar.

The chimeric membrane localization polypeptide can localize one or more agents associated with the peptide about the nucleus. The agents may be any compound, active agent, nucleic acids, DNA, RNA PNAs, drugs, pharmaceutical agents, isotopes, heavy metals, nano-particles, lipids, carbohydrates, proteins, amino acids, vitamins, polymers, detectable labels, a PY-NLS, pharmaceutical agents, isotopes, heavy metals, nano-particles, lipids, carbohydrates, proteins, amino acids, vitamins, polymers, detectable labels, polypeptides and combinations thereof.

The present invention provides an isolated and purified polypeptide that translocates an agent across a nuclear membrane. The polypeptide includes a Karyopherin beta2 translocation motif having a peptide with a slightly positively charged region or a slightly hydrophobic region and one or more R/K/H-$X_{(2-5)}$-P-Y motifs (SEQ ID NO: 1), whereby the peptide targets an agent into the cell nucleus. In some embodiments, the chimeric membrane localization polypeptide includes one or more binding domains or motifs to associate with the one or more agents. The C-terminal of hnRNP M-NLS may include one or more R/K/H-$X_{(2-5)}$-P-Y motifs.

The polypeptide also includes one or more agents associated with the peptide, wherein the one or more agents are selected from nucleic acids, PNAs, drugs, pharmaceutical agents, isotopes, heavy metals, nano-particles, lipids, carbohydrates, proteins, amino acids, vitamins, polymers, detectable labels, polypeptides that translocates an agent nuclear membranes and combinations thereof. In some instances, the polypeptide further includes an agent binding motif. The agent binding motif binds one or more nucleic acids, PNAs, drugs, pharmaceutical agents, isotopes, heavy metals, nanoparticles, lipids, carbohydrates, proteins, amino acids, vitamins, polymers, detectable labels, polypeptides that translocates an agent nuclear membranes and combinations thereof.

Karyopherinβ (Kapβ) proteins bind nuclear localization and export signals (NLSs and NESs) to mediate nucleocytoplasmic trafficking, a process regulated by Ran GTPase through its nucleotide cycle. Diversity and complexity of signals recognized by Kapβs have prevented prediction of new Kapβ substrates. The structure of Kapβ2 bound to one of its substrates, the NLS of hnRNP A1, explains the mechanism of substrate displacement by Ran GTPase. Further analyses reveal three rules for NLS recognition by Kapβ2: NLSs are structurally disordered in free substrates, have overall basic character, and possess a central hydrophobic or basic motif followed by a C-terminal R/H/K$X_{(2-5)}$PY (SEQ ID NO: 1) consensus sequence. The present invention provides a method of identifying NLSs in seven previously known Kapβ2 substrates. For example the present invention provides 81 new substrates. These present invention provides new NLS that could not be predicted by primary sequence analysis alone.

The crystal structure of Kapβ2 bound to its substrate M9NLS has revealed a set of rules that describe the recognition of a large class of nuclear import substrates. M9NLS adopts an extended conformation for about 26 residues when bound to Kapβ2, leading to the first rule, that NLSs recognized by Kapβ2 are structurally disordered in the free substrates. The structure also shows that the substrate binding site on Kapβ2 is highly acidic, leading to the second rule, that NLSs will have an overall positive charge. Finally, biochemical analyses of Kapβ2-M9NLS interactions have mapped M9NLS residues that are important for Kapβ2 binding and examination of other Kapβ2 substrates has revealed consensus motifs at these regions. The consensus motifs include a central hydrophobic or basic motif followed by a C-terminal R/K/H$X_{(2-5)}$PY motif (SEQ ID NO: 1), leading to the name PY-NLSs for this class of signals. Although these rules are not strong filters individually or in pairs (not shown), together they provide substantial restrictions in sequence space. The three rules have been used to identify NLSs in seven previously identified Kapβ2 substrates and more importantly 81 new candidate Kapβ2 substrates in our initial bioinformatics endeavor. Of the members of this group with annotated subcellular localization, >90% are reported to be nuclear localized. The present invention provides seven new NLSs of known Kapβ2 substrates and five of the 81 new bioinformatics-predicted substrates for experimentally validated Kapβ2 recognition as well as Ran-mediated dissociation, demonstrating the predictive nature of the rules. The large number of Kapβ2 substrates further suggests the prevalence of PY-NLSs in the genome. Finally, the fact that all 81 proteins likely use Kapβ2 suggests potential functional linkages in the group that may be revealed by comparison with other genome-wide analyses.

Kapβ2-M9NLS complex: Structure overview. FIGS. 1A and 1B are an images of a crystal structure of the Kapβ2-M9NLS complex. FIG. 1A is a ribbon diagram of the Kapβ2-M9NLS complex with Kapβ2 in red (α-helices represented as cylinders and structurally disordered loops as red dashes) and M9NLS shown as a stick figure (carbon—green, oxygen—red, nitrogen—blue and sulfur—orange). FIG. 1B is an image of the 20 HEAT repeats and H8 loop of Kapβ2 used in structural analyses (red), and M9NLS (light green) within hnRNP A1 (green). The deleted portion of the H8 loop is in yellow. FIG. 1C is an image of the M9NLS binding site with Fo-Fc map (about 2.5σ) calculated using Kapβ2 alone (blue mesh), drawn with PYMOL (DeLano, 2002). Kapβ2 is a superhelical protein with 20 HEAT repeats. It is almost exclusively α-helical except for about a 62-residue loop in repeat 8 (H8 loop; FIG. 1A). Each repeat consists of two antiparallel helices A and B, each lining the convex and concave side of the superhelix respectively (Chook and Blobel, 1999; Chook et al., 2002).

HEAT repeat Nomenclature. Individual helices are named according to their position in the HEAT repeat such that the A helix of HEAT repeat 1 is abbreviated to H1A. HEAT repeat 1 spans residues about 1-40 and includes the first two helices (Chook et al., 2002). The first and last pairs of helices in the originally reported Kapβ2-Ran structure were not labeled as HEAT repeats due to structural deviations compared to other repeats (Chook and Blobel, 1999). However, they were later renamed to repeats H1 and H20 to conform to a standard Kapβ HEAT numbering system (Bayliss et al., 2000; Chook et al., 2002; Cingolani et al., 1999; Vetter et al., 1999).

TABLE 1

Kap β2-M9NLS Complex Data Collection:

| Native: | | Selenomethionine: | |
|---|---|---|---|
| Resolution 100.00-3.05 Å | | Resolution 100.00-3.30 Å | |
| Space group C2 | | Space group C2 | |
| a = 152.01 Å, b = 154.09 Å, | | a = 155.65 Å, b = 154.59 Å, | |
| c = 141.67 Å, β = 91.75° | | c = 141.56 Å, β = 91.56° | |
| *$R_{sym}$ | 0.055 (0.429)[#] | *$R_{sym}$ | 0.103 (0.500)[#] |
| I/σ | 24.7 (2.0)[#] | I/σ | 21.5 (2.1)[#] |
| Redundancy | 4.6 (4.1)[#] | Redundancy | 4.9 (4.7)[#] |
| Completeness | 99.0% (92.8%)[#] | Completeness | 98.5% (91.5%)[#] |

| Refinement: |
|---|
| Resolution 100.00-3.05 Å |
| [†]$R_{factor}$ = 0.2401 $R_{free}$ = 0.2501 |
| rmsd from ideal bond lengths 0.0074 Å |
| rmsd from ideal bond angles 1.136° |
| Ramachandran Plot: 90.4% in most favored regions, 9.6% in allowed regions |

| Model: | Residues | Average B factor |
|---|---|---|
| Complex 1: | | |
| Kap β2 Chain A | 6-36, 44-77, 80-319, 368-890 | 72.7 Å$^2$ |
| M9NLS Chain C | 263-289 | 81.9 Å$^2$ |
| Complex 2: | | |
| Kap β2 Chain B | 6-36, 44-55, 59-75, 80-319, 368-890 | 74.4 Å$^2$ |
| M9NLS Chain D | 266-289 | 77.6 Å$^2$ |

*Rsym = $\Sigma_h \Sigma_i | (I_i(h) - <I(h)>| / \Sigma_h \Sigma_i I_i(h)$; $I_i(h)$ is the i-th measurement of reflection h and <I(h)> is the weighted mean of all measurements of h.
[#]values in parentheses are calculated for data in the highest resolution shell
[†]R-factor = $\Sigma_h ||F_{obs}(h)| - |F_{calc}(h)||/\Sigma_h F_{obs}(h)|$; $R_{free}$ is calculated with 10% of the data.

The Kapβ2-M9NLS crystals contain a Kapβ2 mutant with a truncated H8 loop bound to residues about 257 to about 305 of hnRNP A1 (FIG. 1B). Biochemical studies showed that the loop neither hinders nor is necessary for substrate binding. However, it is sensitive to proteolytic degradation in substrate-bound Kapβ2, suggesting structurally flexibility (Chook et al., 2002). In the final Kapβ2 construct, the H8 loop was truncated (a GGSGGSG linker (SEQ ID NO: 2) replaces residues about 337-367) to minimize disorder in the crystal. The Kapβ2-M9NLS crystal structure was solved to 3.05 Å resolution (Table 2, PDB ID code 2H4M).

Figure 2B:
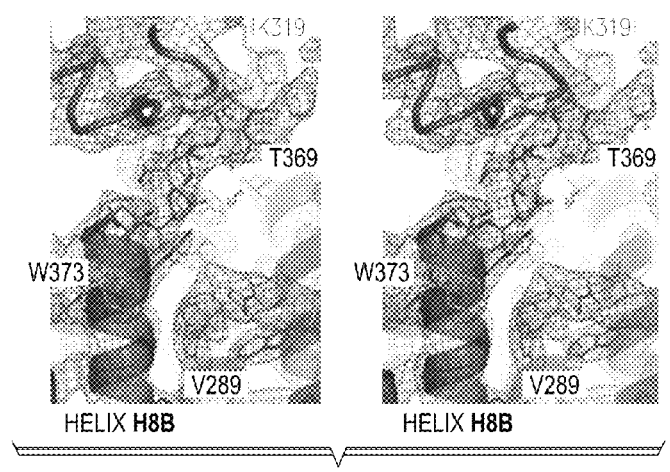
Figure 2C:
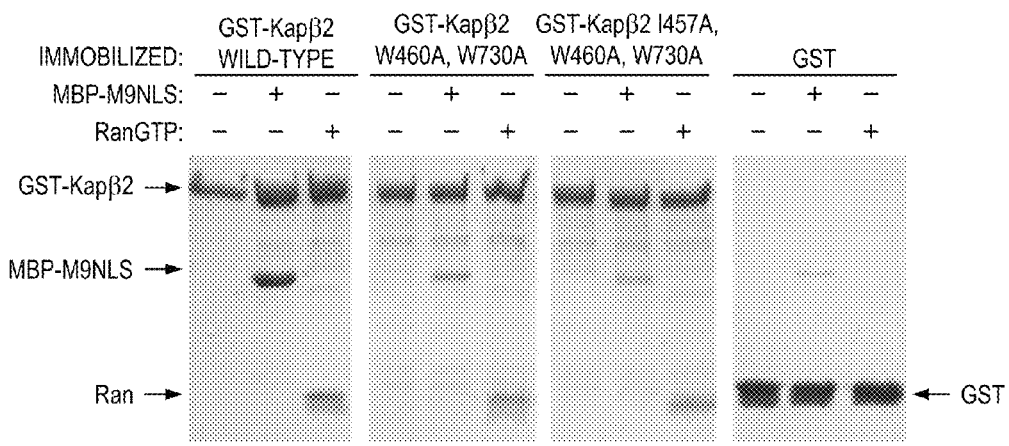

FIG. 2A is a stereo diagram of the 2Fo-Fc map (about 1.0σ, blue mesh) drawn at Kapβ2 (red) HEAT repeat 8, showing H8 loop residues about 312-319 connecting to H8A and residues about 369-374 to H8B. A neighboring Kapβ2 in the crystal is shown as a yellow ribbon. Red dashes represent the disordered connection between loop residues 319 and 369. FIG. 2B is similar to FIG. 2A that has been rotated about 90° about the vertical axis. M9NLS is in green. FIGS. 2C is an image of a gel demonstrating the binding studies of MBP-M9NLS and immobilized Kapβ2 mutants. Control studies were also performed using immobilized Kapβ2 proteins and RanGTP.

The asymmetric unit of the crystal contains two Kapβ2-M9NLS complexes (I and II). All residues in both Kapβ2s are modeled except for three short loops at the N-termini, H8 loop residues 320-337 and the engineered GGSGGSG H8 loop linker (SEQ ID NO: 2) (disordered regions are indicated by dashes in FIGS. 1A, 2A and 2B). FIG. 2C is an image of a gel illustrating the products. Substrate residues about 267-289 are observed in complex I, while additional substrate residues 263-266 are modeled in complex II (FIG. 1C). Thus, the latter is used in structural analysis and discussion below. HEAT repeats 5-20 share similar conformations in both complexes (rmsd about 1.7 Å). In contrast, HEAT repeats 1-4 diverge to a distance of 7 Å at their N-termini with high average B-factors (93 Å$^2$ for complex I and about 118 Å$^2$ for complex II), suggesting inherent conformational flexibility in this region of Kapβ2.

The 20 HEAT repeats of the Kapβ2-M9NLS complex form an almost perfect superhelix (e.g., pitch about 72 Å, diameter about 60 Å and length about 111 Å; FIG. 1A). The superhelix can also be described as two overlapping arches, with the N-terminal arch spanning HEAT repeats 1-13 and the C-terminal arch spanning repeats 8-20. In the Kapβ2-Ran complex, RanGTP binds in the N-terminal arch (Chook and Blobel, 1999). M9NLS binds in the C-terminal arch as seen in FIGS. 1A and 1C.

The Kapβ2-M9NLS binding interface. M9NLS binds in extended conformation to line the concave surface of C-terminal arch of Kapβ2 as seen in FIG. 1A. Its peptide direction is antiparallel to that of the karyopherin superhelix, and substrate buries about 3432 Å$^2$ of surface area in both binding partners. Tracing M9NLS from N— to C-terminus, residues 263-266 interact with helices H18A, H19A and H20B of Kapβ2 while residues 267-269 drape over the intra-HEAT 18 loop into the C-terminal arch of the karyopherin. The rest of M9NLS follows the curvature of the C-terminal arch to contact B helices of repeats 8-17 as seen in FIGS. 1A and 2A.

FIG. 3 contains graphs (13 sets in total) of the ITC profiles of MBP, MBP fusions of wild type M9NLS and various alanine mutants interacting with full length Kapβ2. Nonlinear least squares fits to the single binding site model were use to fit the ITC profiles (closed squares).

Figure 4:
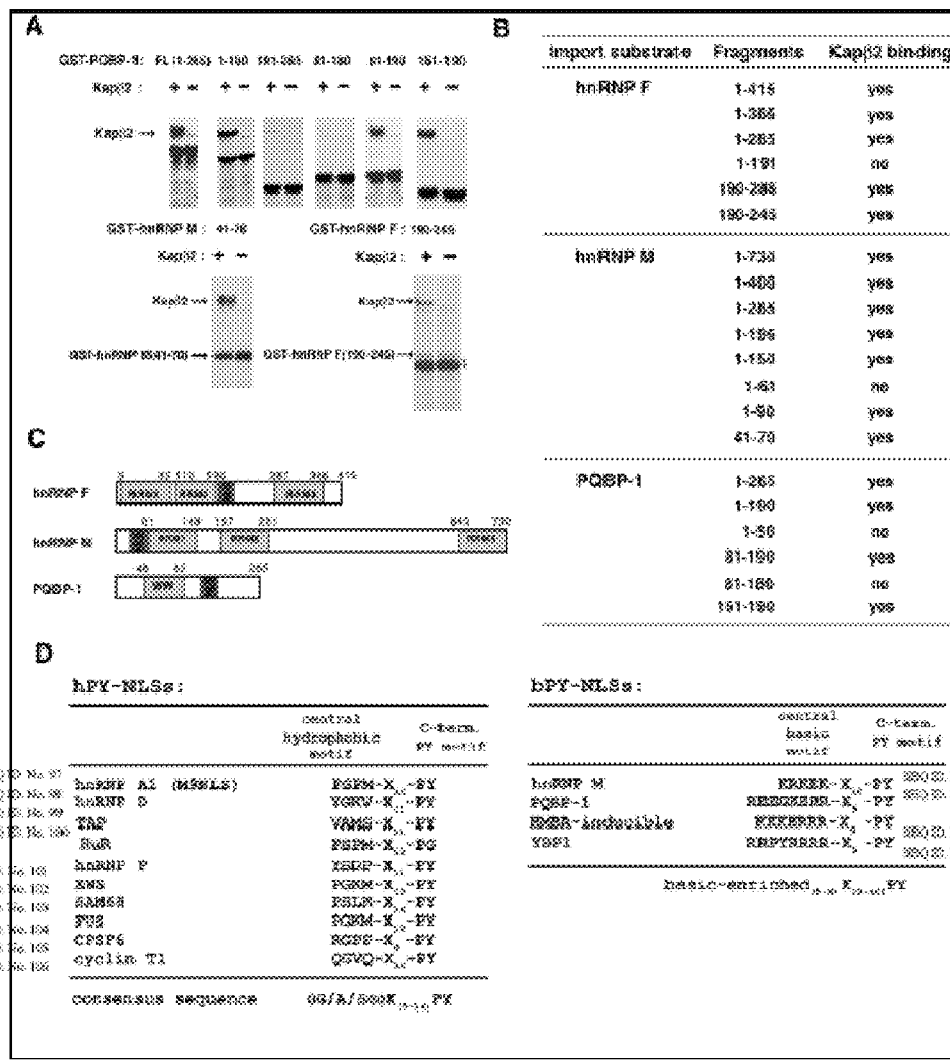
FIG. 4A-4D are images and summaries of the binding assay of Kapβ2 and immobilized deletion mutants of PQBP-1, hnRNP M, and F, in FIG. 4D, left column, SEQ ID NOS: 97 to 106, and right column, SEQ ID NOS.: 107 to 110.

FIG. 4A is an image of a binding assay of Kapβ2 and immobilized deletion mutants of PQBP-1, hnRNP M, and F. Degraded fragments of the substrates are labeled with asterisks. FIG. 4B is a table summary of all binding assays to map NLSs of PQBP-1, hnRNP M, and F. FIG. 4C is an image of the location of newly characterized NLSs of PQBP-1, hnRNP M, and F. RNA binding domains (RRMs) and WW-domain are shaded light gray and the NLSs are shaded dark gray. FIG. 4D is a table summary of the central hydrophobic and basic motifs of the PY-NLSs.

Figure 5A:
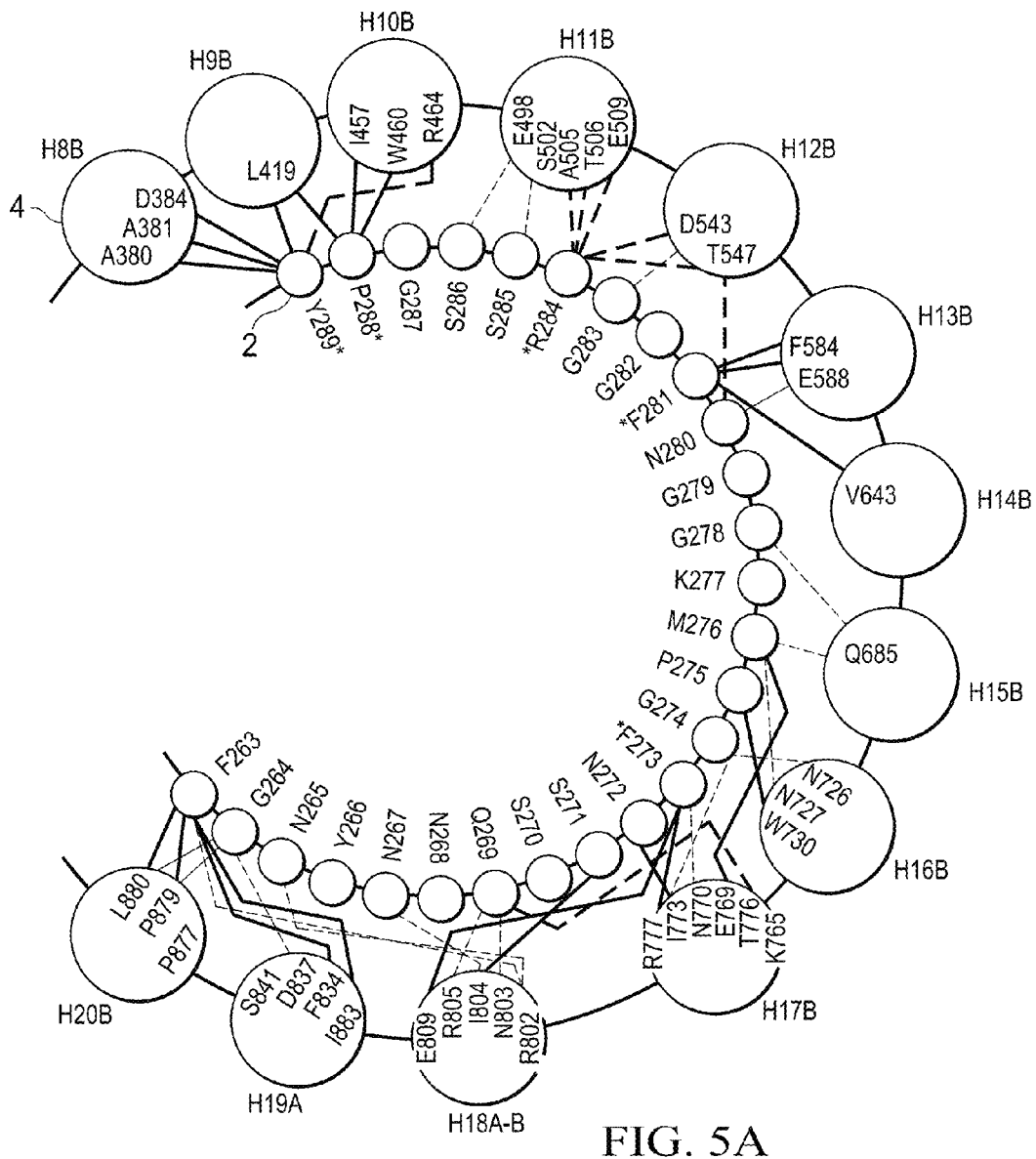
FIGS. 5A-D are images of Kapβ2-M9NLS interactions.

FIGS. 5A-D are images of Kapβ2-M9NLS interactions. FIG. 5A is an image of Kapβ2-M9NLS contacts (<4.0 Å) with M9NLS residues in green circles (the lighter circles 2) and Kapβ2 helices as pink circles (the darker circles 4). Contacts involving main chain atoms of M9NLS are shown with green lines (lighter colored dashed lines). Contacts involving M9NLS sidechains are shown with black lines. Solid lines are hydrophobic contacts and dashed lines are polar contacts. Red asterisks label M9NLS residues that make two or more sidechain contacts in both complexes in the asymmetric unit.

Figure 5B:
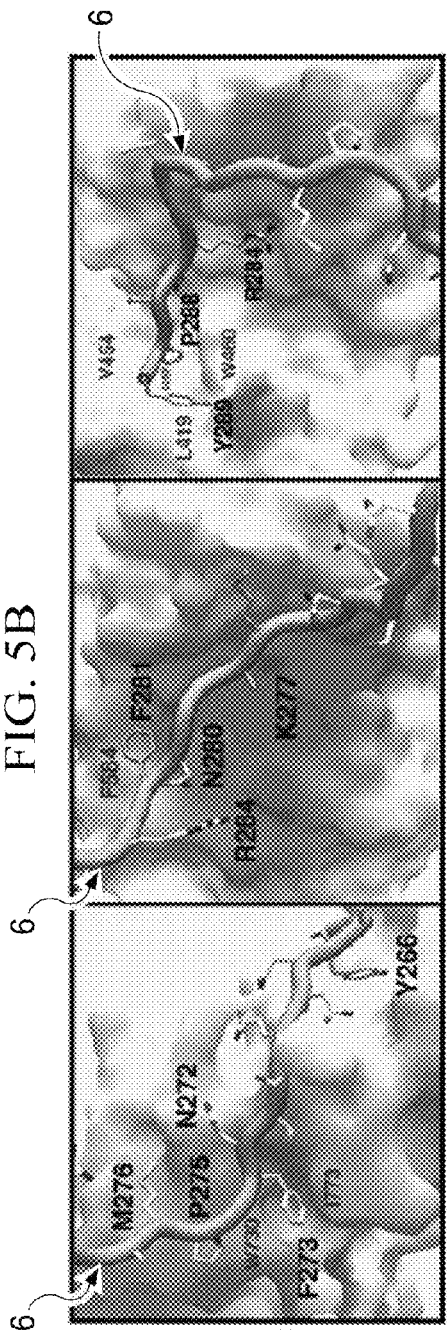

FIG. 5B is an image of the Kapβ2-M9NLS interface. The N-terminal third (left), the central region (middle) and the C-terminal third (right) of M9NLS. Substrate is shown as a green ribbon 6 and the Kapβ2 electrostatic potential is mapped onto its surface, all drawn using GRASP (Nicholls et al., 1991). Gray indicates negative electrostatic potential, white neutral and blue positive. Residues in the hydrophobic patches of Kapβ2 are labeled in red and M9NLS residues labeled in black.

Figure 5D:
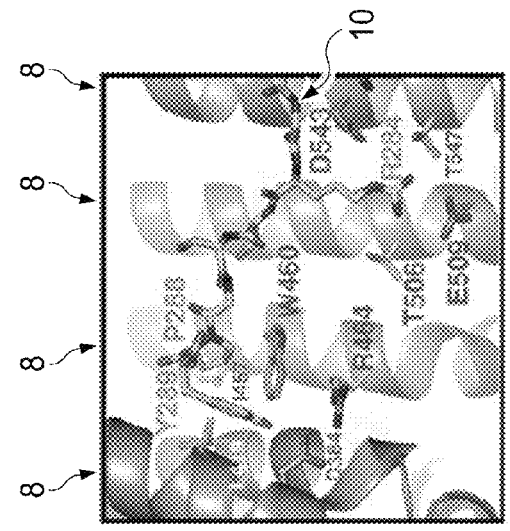
Figure 5C:
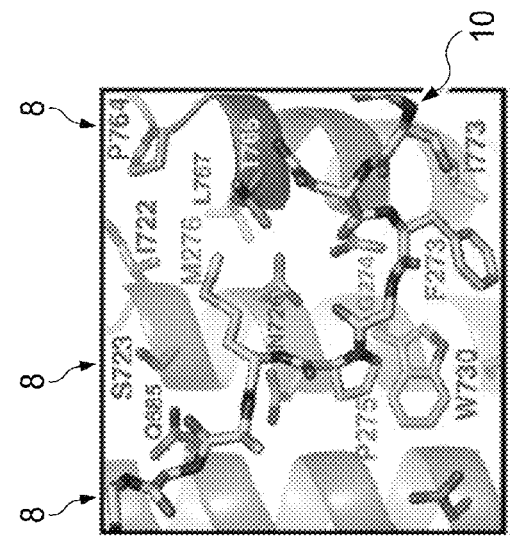

FIG. 5C is an image of interactions between Kapβ2 (red) and substrate at M9NLS (green) residues [273]FGPM[276] (SEQ ID NO: 3), drawn using PYMOL (DeLano, 2002). FIG. 5D is an image of interactions between Kapβ2 8 and M9NLS 10 at the C-terminus of the substrate, drawn using PYMOL (DeLano, 2002). The substrate interface on Kapβ2 comprises about 30% of the concave surface of the C-terminal arch, which is relatively flat and devoid of deep pockets or grooves.

Most of this surface, which includes the M9NLS interface, is also highly acidic as seen in FIG. 5B.

M9NLS forms an extensive network of polar and hydrophobic interactions with Kapβ2, involving both the main chain and sidechains of the substrate (FIG. 2A). Most of the substrate interface on Kapβ2 is acidic with the exception of several scattered hydrophobic patches. At the N-terminus of M9NLS, residues 263-266 contact a hydrophobic patch on Kapβ2 helices H19A and H20B as seen in FIG. 5B, left. In the central region, a hydrophobic stretch $^{273}$FGPM$^{276}$ (SEQ ID NO: 3) contacts hydrophobic Kapβ2 residues I773 and W730 (FIGS. 5B and 5C). Farther C-terminus, F281 binds near a hydrophobic patch formed by Kapβ2 residues F584 and V643 (FIG. 5B, center) and finally, the C-terminal 288PY289 residues bind a large hydrophobic swath that includes Kapβ2 residues A380, A381, L419, I457 and W460 (FIGS. 5B, right and 5D). Despite the extensive acidic interface on Kapβ2, there are only two basic residues in M9NLS. R284 forms salt links with Kapβ2 residues E509 and D543, and the sidechain of K277 is not observed. Distribution of binding energy along M9NLS.

In order to understand the distribution of binding energy along M9NLS, dissociation constants ($K_D$s) of a series of M9NLS mutants binding to Kapβ2 were measured using isothermal titration calorimetry (ITC). The results of the binding studies using MBP-fusion proteins of M9NLS residues 257-305 and wild type Kapβ2 are summarized in Table 2 and FIG. 3. Wildtype M9NLS binds Kapβ2 with a $K_D$ of 42 nM. This ITC-measured affinity is somewhat lower than the previous $K_D$ of 2 nM measured by fluorescence titration, but may be explained by the presence of both a covalently attached aromatic fluorophore and a significantly longer M9NLS spanning residues 238-320 in the earlier studies (Chook et al., 2002). Substrate residues that make two or more sidechain contacts with Kapβ2 (F273, F281, R284, P288 and Y289) were systematically mutated to alanines. Additional residues G274, P275 and M276 were also mutated given their implied importance in yeast-two-hybrid studies (Bogerd et al., 1999). Table 2 is a table lists the dissociation constants by isothermal calorimetry for Kap β2 binding to M9NLS mutants. G274A is the only single mutant that shows significant (about 18-fold) decrease in Kapβ2 binding, see Table 2 below:

TABLE 2

| MBP-M9NLS(257-305) proteins | $K_D$ |
|---|---|
| Wild type | 42 ± 2 nM |
| F273A | 61 ± 10 nM |
| G274A | 746 ± 63 nM |
| P275A | 74 ± 5 nM |
| M276A | 83 ± 17 nM |
| F281A | 56 ± 11 nM |
| R284A | 92 ± 9 nM |
| P288A | 158 ± 20 nM |
| Y289A | 133 ± 21 nM |
| P288A/Y289A | 136 ± 8 nM |
| R284A/P288A/Y289A | 461 ± 27 nM |
| G274A/P288A/Y289A | 5.9 ± 0.7 μM |

Single mutants of C-terminal residues P288 and Y289 follow with modest decreases of about 3-4 fold. Thus, it appears that M9NLS binds Kapβ2 in a mostly distributive fashion, with a strict requirement for glycine at position 274 and modest though possibly important energetic contributions from C-terminal residues P288 and Y289. The importance of the PY motif is suggested in the R284/P288N/Y289 and G274/P288N/Y289 triple mutants where about 10-fold and about 140-fold decreases were observed, respectively. Both triple mutants show non-additivity in their binding energies when compared with single G274A, R284A and the double PY mutants, suggesting cooperativity between the C-terminal PY motif and both upstream binding sites at R284 and G274. The significance the G274A mutation had previously been reported in both Kapβ2-binding and nuclear import assays (Fridell et al., 1997; Nakielny et al., 1996). The alpha carbon of G274 is in close proximity to neighboring substrate sidechains F273 and P275 as well as Kapβ2 residue W730, such that a sidechain in position 274 may result in a steric clash as seen in FIG. 5C.

The important energetic contributions of the substrate's C-terminal PY motif and its central G274 residue are also supported by mutations of interacting residues in Kapβ2. Double and triple Kapβ2 mutants, W460A/W730A and I457A/W460A/W730A, both show significant decreases in Kapβ2 binding in FIG. 2C. I457 and W460 interact with the substrate PY motif while W730 makes a hydrophobic contact with substrate P275 and is also close to G274 as seen in FIGS. 5C and 5D.

Rules for substrate recognition by Kapβ2. Prior to this study, among more than 20 known Kapβ2 substrates, only NLSs from hnRNP A1, D, HuR, TAP and their homologs had been identified (Fan and Steitz, 1998; Kawamura et al., 2002; Siomi and Dreyfuss, 1995; Suzuki et al., 2005; Truant et al., 1999). All four NLSs span 30-40 residues, are rich in glycine and serine residues, have overall basic character, but share little sequence homology. To aid in assessment of the rules for NLS recognition by Kapβ2 suggested below, a series of deletion mutants were constructed to map three additional NLSs from hnRNP F, M and PQBP-1. The results of in vitro binding assays map the NLSs to residues 151-190 in PQBP-1, residues 41-70 in hnRNP M and residues 190-245 in hnRNP F about FIGS. 4A-C. Structural and mutagenesis analysis of the Kapβ2-M9NLS complex combined with sequence comparison and analysis of all seven NLSs reveals three rules for NLS recognition by Kapβ2.

Rule 1: NLS is structurally disordered in substrate. The extended conformation of the 26-residue M9NLS results in a linear epitope that traces a path of about 110 Å. The structure of the bound substrate suggests that an NLS recognized by Kapβ2 should exist within a stretch of at least 30 residues that lacks secondary structure in its native, unbound state. Thus, the NLS is most likely structurally disordered in the free substrate. The prediction of this NLS requirement is further supported by the fact that all seven known NLSs in Kapβ2 substrates occur within sequences with high probability of structural disorder (>0.7) calculated by the program DISEMBL (Linding et al., 2003). All seven NLSs are found either in loop regions between the RNA binding or other folded domains or at the termini of the substrates.

Figure 6:
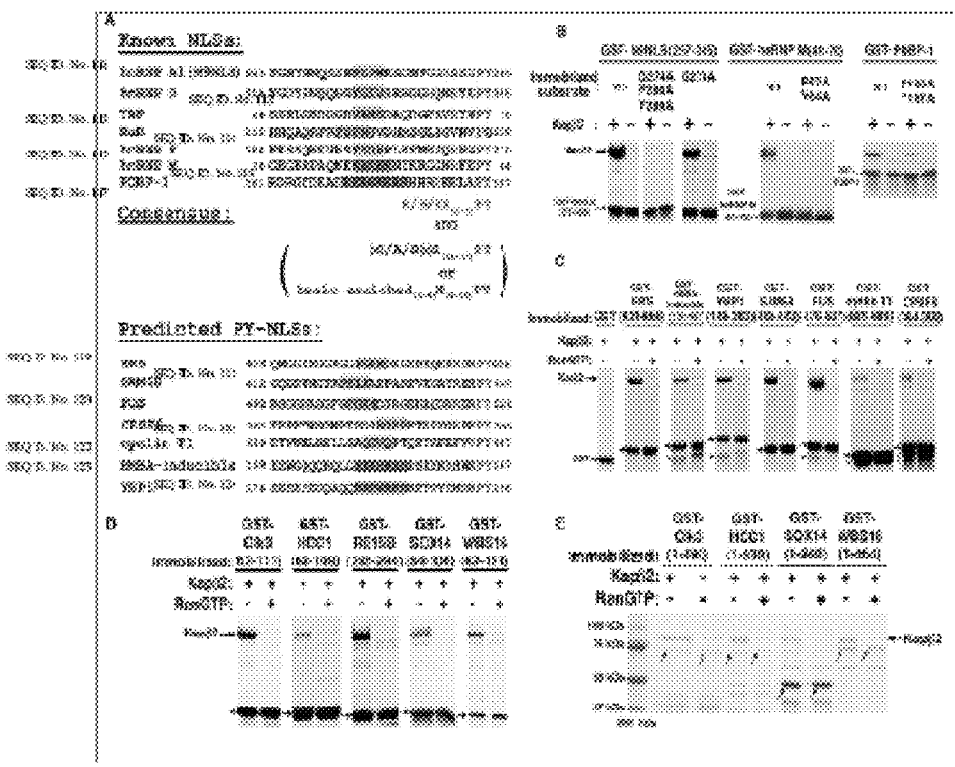
FIGS. 6A-6E are images and table summaries of the known Kapβ2 NLSs indicates overall basic characteristics, in FIG. 6A known SLNs include SEQ ID NOS: 111 to 117, and Predicted PY-NLS are SEQ ID NOS: 118 to 124.

Rule 2: Overall positive charge for NLS is preferred. A second requirement for an NLS recognized by Kapβ2 emerges from the observation that Kapβ2's substrate interface is highly negatively charged. An acidic peptide would likely not bind due to electrostatic repulsion, while an NLS with overall positive charge would most likely be favored. Examination of all known Kapβ2 NLSs indicates overall basic character spanning at least 30 residues in six of seven cases as illustrated in FIG. 6. In addition, regions that flank the NLSs most likely also contribute favorably to electrostatics. For example, although the TAP-NLS sequence delineated in FIG. 6A has slightly more acidic than basic residues, flanking regions are highly basic and may ultimately contribute to overall basic character to promote Kapβ2 binding. The importance of basic flanking regions is also observed in hnRNP A1. Here, the entire 135-residue C-terminal tail of the substrate has overall positive charge. A recent study showed that following osmotic shock stress in cells, four serine residues C-terminally adjacent to the M9NLS are phosphorylated, resulting in decreased binding to Kapβ2 and accumulation of hnRNP A1 in the cytoplasm (Allemand et al., 2005). Phosphorylation of the M9NLS-flanking serines may decrease the basic character of M9NLS and thus modulate interactions with Kapβ2.

Rule 3: Consensus sequences for the NLS. All seven characterized NLSs recognized by Kapβ2 exist in structurally disordered regions suggesting that this class of NLS is represented by linear epitopes and not folded domains. However, apparent sequence diversity among previously characterized NLSs from hnRNP A1, HuR, TAP and JKTBP homologs had prevented delineation of a consensus sequence that could be used to identify new NLSs or substrates. However, despite apparent NLS diversity, mutagenesis, structural and sequence analysis have resulted in identification of two regions of conservation within the sequences.

FIGS. 6A-6E illustrate the consensus sequences of NLSs recognized by Kapβ2. FIG. 6A a sequence alignment of all known (top) and predicted NLSs (bottom) recognized by Kapβ2, at conserved PY residues. NLSs in known Kapβ2 substrates are predicted by the presence of the R/K/H-$X_{(2-5)}$-P-Y C-terminal motifs (SEQ ID NO: 1) (red) within structurally disordered and positively charged regions of 30 amino acids. Central hydrophobic motifs φG/A/Sφφ (φ is a hydrophobic sidechain) are shaded yellow. Central basic motifs are shaded blue. FIG. 6B is an image of gels demonstrating binding assays of Kapβ2 and immobilized alanine mutants of M9NLS, PQBP-1 and NLS-containing fragments of hnRNP M. Bound proteins are visualized with Coomassie Blue.

FIG. 6C is an image of gels demonstrating binding assays of predicted NLSs from known Kapβ2 substrates EWS, HMBA-inducible protein, YBP1, SAM68, FUS, cyclin T1 and CPSF6. Kapβ2 is added to immobilized GST-NLSs (arrows) in the presence and absence of excess RanGTP, and bound proteins visualized with Coomassie Blue. Asterisks label degraded fragments of substrates.

FIG. 6D is an image of gels demonstrating the five predicted Kapβ2 substrates (Clk3, HCC1, RB15B, Sox14 and WBS16) are validated experimentally. GST-NLSs (arrows) are immobilized on glutathione sepharose. FIG. 6E is an image of gels demonstrating binding assays of full-length substrates Clk3, HCC1, Sox14 and WBS16 to Kapβ2. Expression of recombinant full-length RB15B was not successful. Coomasie-stained bands at the size of the GST-substrates are labeled with arrows. Lower molecular weight proteins are likely degraded substrates.

The first region of conservation is found at the C-terminus of the NLSs. Mutagenesis of M9NLS suggested the importance of its C-terminal PY motif as seen in Table 2. Sequence examination of previously characterized NLSs from hnRNP D, HuR and TAP as well as the newly characterized NLSs of hnRNP F, M and PQBP-1, identified consecutive PY residues in six of the seven sequences as seen in FIG. 6A. Mutations of the PY residues in PQBP-1 and hnRNP M also decreased Kapβ2 binding suggesting that they make energetically important contacts in the image in FIG. 6B. Mutations of the PY motif in JKTBP proteins and M9NLS were also previously shown to inhibit nuclear import (Iijima et al., 2006; Suzuki et al., 2005). In addition, a basic residue is always found several residues N-terminal of the PY sequence, consistent with an adjacent acidic surface on Kapβ2 in FIGS. 3B, 3D and 6A. The present invention provides a C-terminal consensus sequence R/K/H-$X_{(2-5)}$-P-Y (SEQ ID NO: 1) (where X is any residue) for NLSs recognized by Kapβ2. The class of NLSs is herein referred to as PY-NLSs.

A second region of conservation within the PY-NLSs is found in the central region of the peptides. Examination of the central region divides the seven PY-NLSs into two sub-classes. The first sub-class includes M9NLS and NLSs of hnRNP D, F, TAP and HuR, where four consecutive predominantly hydrophobic residues are located 11-13 residues N-terminal to the PY residues as seen in FIG. 6A. We refer to this sub-class of sequences as hydrophobic PY-NLSs or hPY-NLSs. In contrast, the central regions of NLSs from hnRNP M and PQBP-1 are virtually devoid of hydrophobic residues but are instead enriched in basic residues. They appear to represent a distinct sub-class of PY-NLSs that we call the basic PY-NLSs or bPY-NLSs.

Figure 3A:
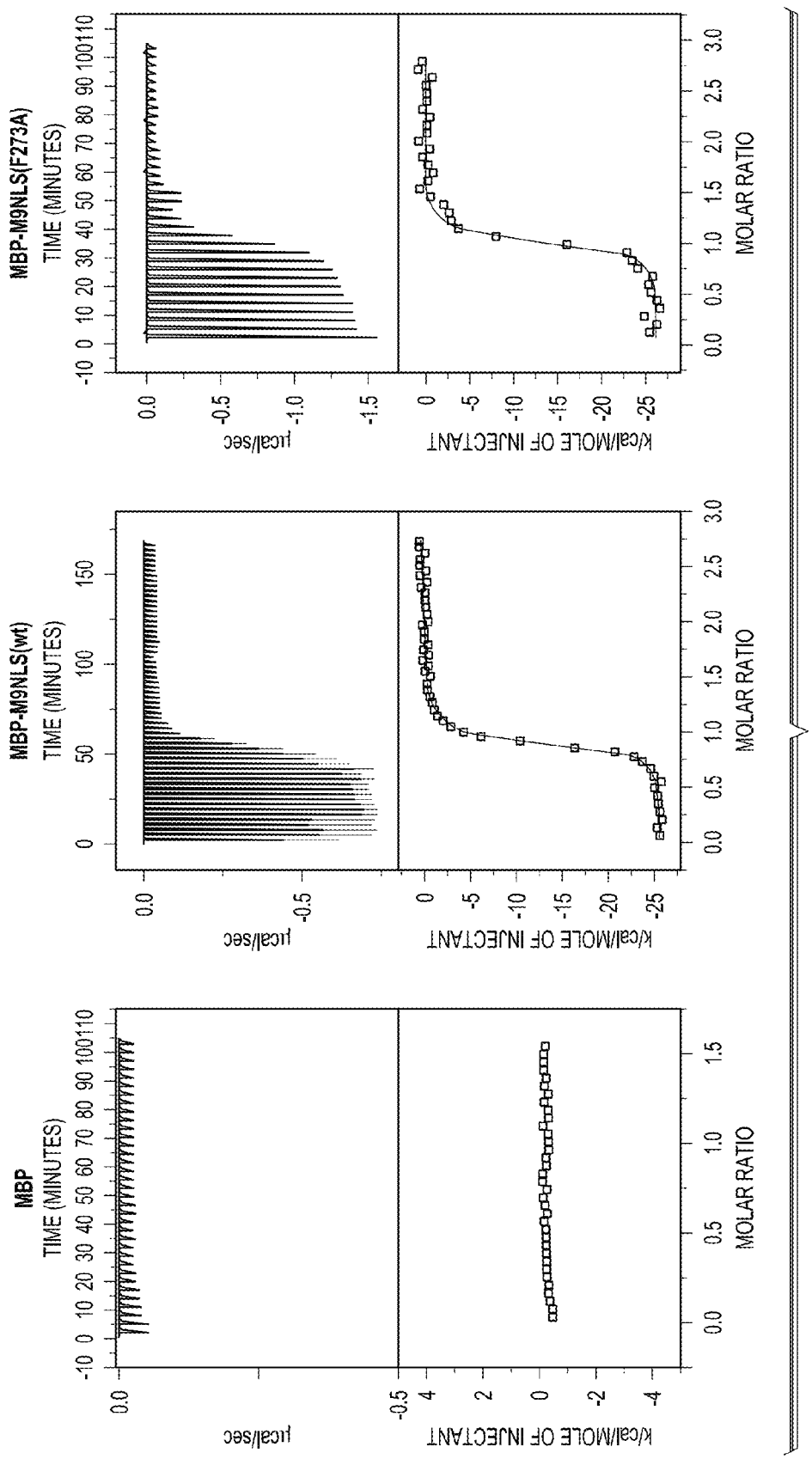
FIG. 3 contains graphs of the ITC profiles of MBP, MBP fusions of wild type M9NLS and various alanine mutants interacting with full length Kapβ2.
Figure 3B:
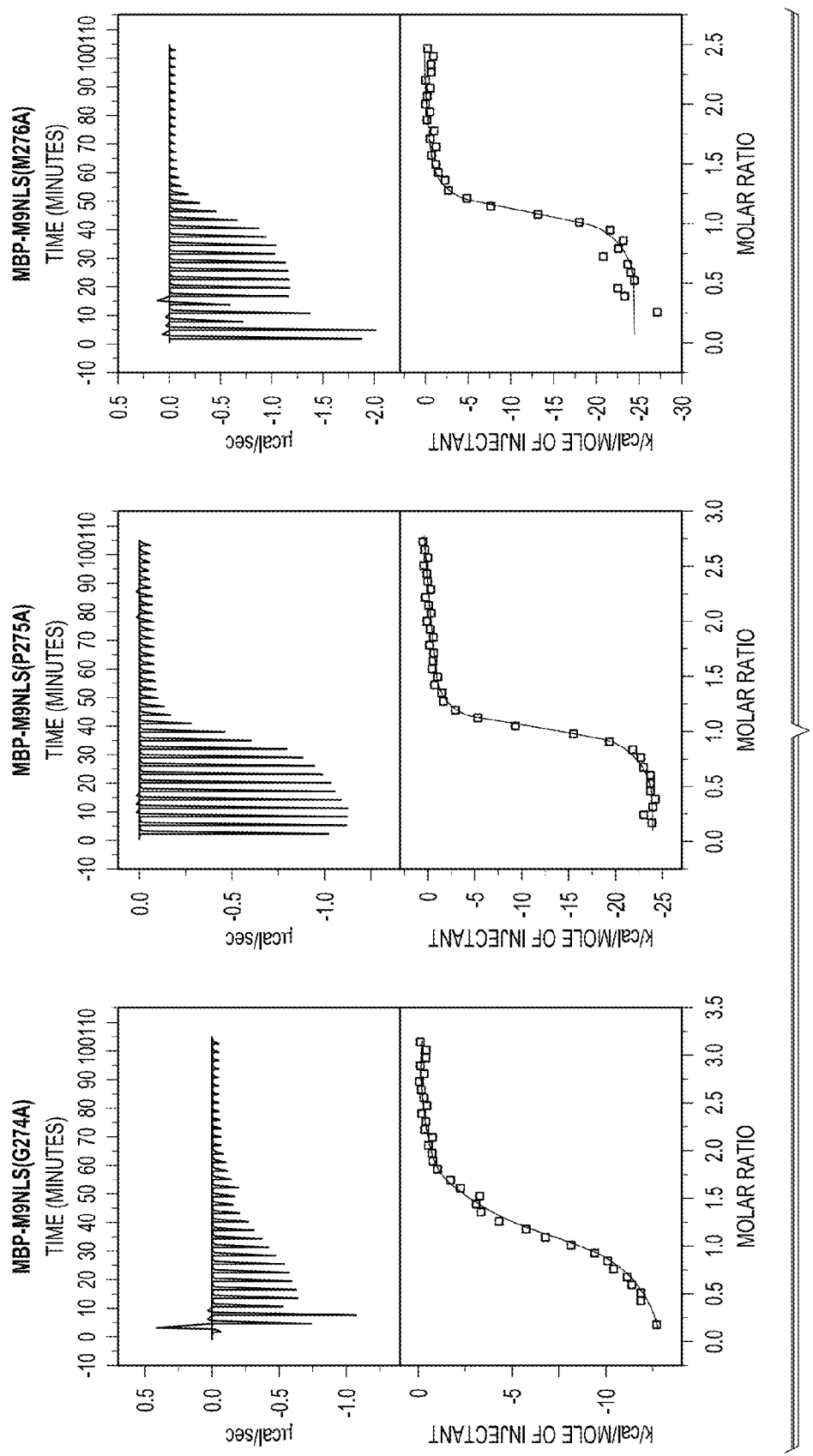
Figure 3C:
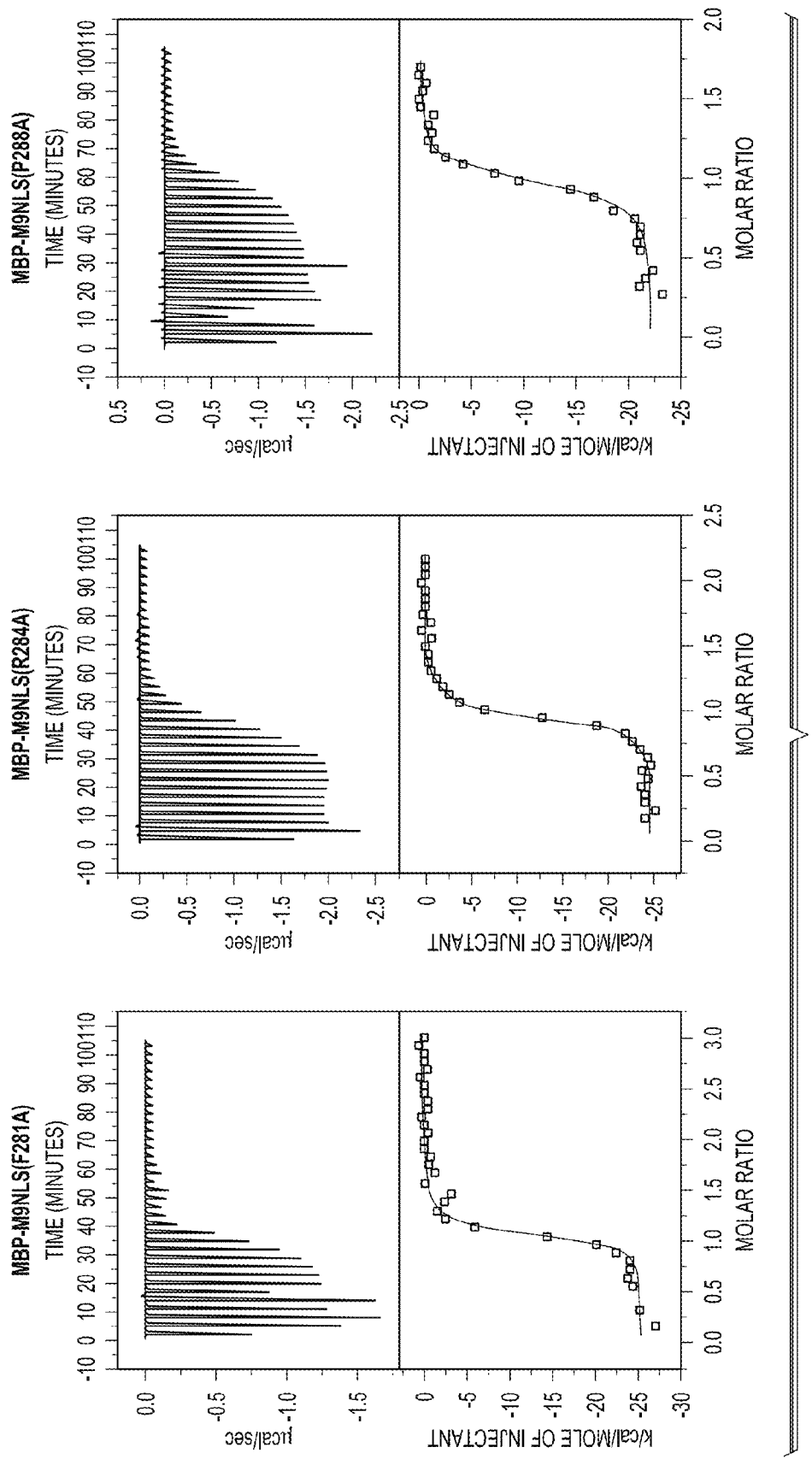
Figure 3D:
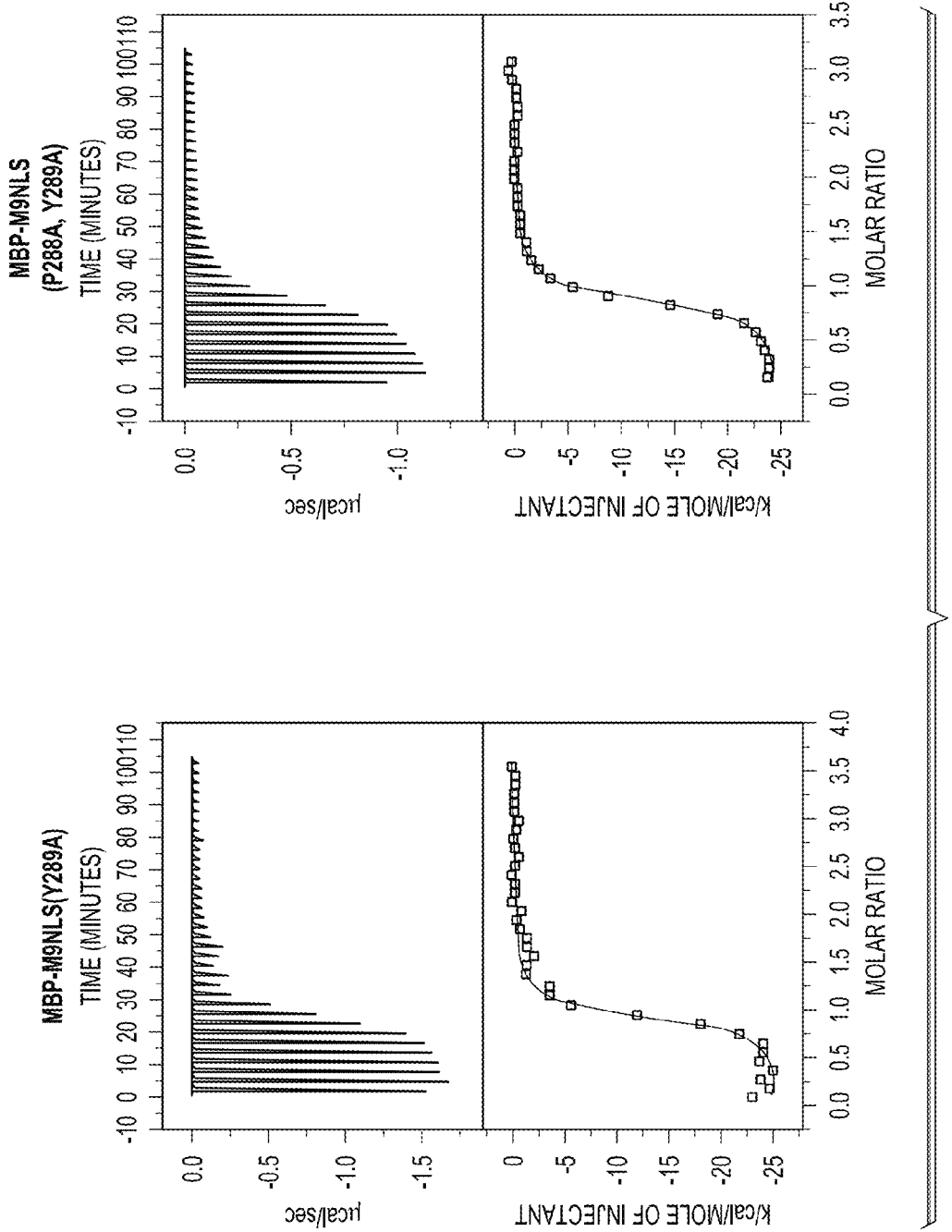
Figure 3E:
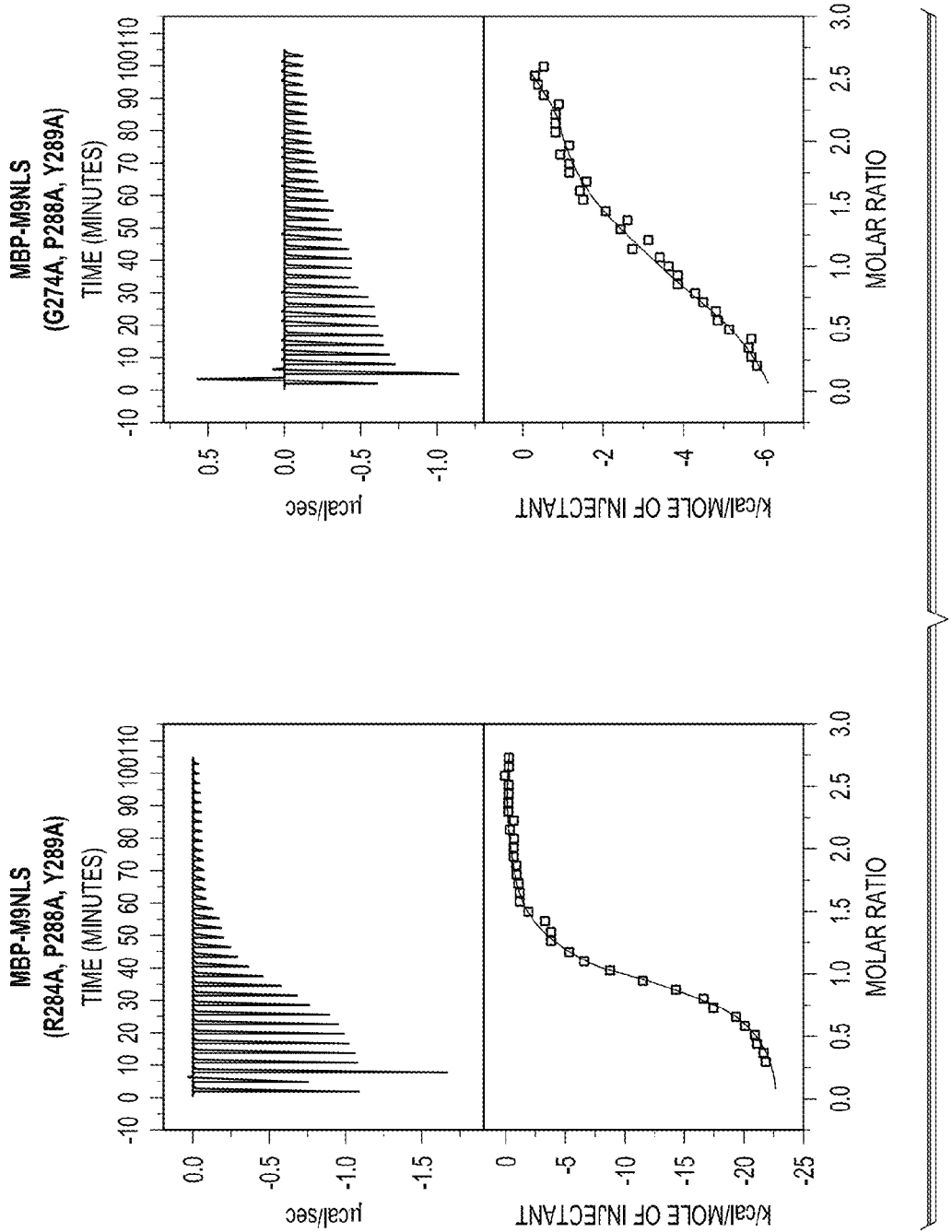

The central hydrophobic motif in M9NLS spans residues $^{273}$FGPM$^{276}$ previously found in yeast two-hybrid and mutagenesis analysis to be important for import by Kapβ2, and a consensus sequence of Z-G-P/K-M/L/V-K/R (SEQ ID NO: 4) (where Z is a hydrophobic residue) was previously suggested (Bogerd et al., 1999). The mutagenesis-derived consensus holds in the context of the M9NLS sequence, but does not describe NLSs in other Kapβ2 substrates. A loose consensus of φ-G/A/S-φ-φ (where φ is a hydrophobic sidechain) seems more appropriate upon comparison of the five central hydrophobic motifs in hnRNPs A1, D, F, TAP and HuR (FIG. 3A). The Kapβ2-M9NLS structure explains preferences for hydrophobic sidechains in positions 1, 3 and 4 as well as small or no sidechain in position 2. Position 1 in M9NLS is F273, which occupies a hydrophobic pocket formed by Kapβ2 residues W730 and I773 (FIG. 5C). Position 3 is occupied by P275, which stacks on top of the indole ring of Kapβ2 W730, and M276 in position 4 binds a small hydrophobic patch on Kapβ2 formed by I722, P764, L766 and the Cβ of S767. Thus, hydrophobic or long aliphatic sidechains at positions 1, 3 and 4 in other hydrophobic hPY-NLSs would provide energetically favorable hydrophobic contacts with Kapβ2. Mutagenesis of M9NLS suggests a strict requirement for glycine at position 2 (residue G274 in M9NLS) of the central hydrophobic motif. G274 is surrounded by adjacent substrate residues F273, P275 and Kapβ2 residue W730, suggesting that the strict requirement for glycine is likely heavily dependent on the identity of adjacent substrate residues. Nevertheless, hydrophobic neighbors, even those not as bulky as F273 and P275 in M9NLS, will likely still not accommodate large sidechains in position 2.

The Kapβ2-M9NLS structure provides some suggestion for the how the central basic motif in the bPY-NLSs could be accommodated. In the structure, the M9NLS hydrophobic motif interacts with Kapβ2 hydrophobic residues that are surrounded by numerous acidic residues as seen in FIGS. 5B and 5C. Thus, the highly acidic substrate interface on Kapβ2 that contacts the central region of an NLS should also be able to interact favorably with numerous basic sidechains. It is possible that the central basic and hydrophobic motifs in the two sub-classes of PY-NLSs may take slightly different paths on Kapβ2. Structures of Kapβ2 bound to bPY-NLSs will be necessary to understand the difference between the two sub-classes of PY-NLSs.

The present invention provides a method of identifying sequences; for example, the sequences of eight recently identified Kapβ2 substrates: Ewing Sarcoma protein (EWS), HMBA-inducible protein, Y-box binding protein 1 (YBP1), SAM68, FUS, DDX3, CPSF6 and cyclin T1 (Guttinger et al., 2004), and found the C-terminal R/K/H-$X_{(2-5)}$-P-Y (SEQ ID NO: 1) consensus within structurally disordered and positively charged regions of seven of them. The predicted NLSs for EWS, HMBA-inducible protein, YBP1, SAM68, FUS, CPSF6 and cyclin T1 are listed in the bottom half of FIG. 6A. The predicted signals in EWS, SAM68, FUS, CPSF6 and Cyclin T1 are hPY-NLSs and those from HMBA-inducible protein and YBP1 are bPY-NLSs (FIG. 4D). The easily-detected PY motif is absent from DDX3, and direct binding of DDX3 to Kapβ2 has not been shown. Thus, DDX3 may not be a substrate of Kapβ2, but may enter the nucleus by binding to a bona-fide Kapβ2 substrate. All seven predicted NLSs bind Kapβ2 and are dissociated from the karyopherin by RanGTP, consistent with NLSs imported by Kapβ2 in FIG. 6C. The NLSs of cyclin T1 and CPSF6 bind Kapβ2, but more weakly than other substrates. Confirmation of these seven NLSs indicates that the three rules for NLS recognition by Kapβ2 described above are predictive.

The NLS rules have been applied to human proteins in the SwissProt protein database (Bairoch et al., 2004) to identify potential Kapβ2 substrates. A search for proteins containing NLS sequence motifs as seen in FIGS. 6A and 4D using the program ScanProsite (Gattiker et al., 2002), followed by filtering for structural disorder (DisEMBL) (Linding et al., 2003) and for overall positive charge in the NLS resulted in 81 new candidate Kapβ2 substrates as seen in Tables 3 and 4.

TABLE 3

Predicted Kapβ2 substrates with hydrophobic PY-NLSs.

| Acc. No. | Name | Local.§ | N-term. Res. | Sequences for candidate Hydrophobic PY-NLS¶ | C-term. Res. | SEQ ID NO: |
|---|---|---|---|---|---|---|
| Q8IZP0 | Abl interactor 1 | C, N | 158 | KHGNNQPARTGTLSRTNPPTQKPPSPP MSGRGTLGRNTPYKTLEPVKPPT | 207 | 5 |
| Q9UKA4 | A-kinase anchor protein 11/AKAP 220 | C, Centrosome | 385 | QRKGHKHGKSCMNPQKFKFDRPALP ANVRKPTPRKPESPYGNLCDAPDSP | 434 | 6 |
| P50995 | Annexin A11 (Annexin XI) (Calcyclin-associated annexin 50) | C, N | 84 | PVPPGGFGQPPSAQQPVPPYGMY PPPGGNPPSRMPSYPPYPGAPVPGQPM | 133 | 7 |
| Q13625 | Apoptosis-stimulating of p53 protein 2 | C, N | 474 | TLRKNQSSEDILRDAQVANKNVAKV PPVPTKPKQINLPYFGQTNQPPSD | 523 | 8 |
| Q9BXP5 | Arsenite-resistance protein 2¥ | not known | 53 | GEYRDYDRNRRERFSPPRHELSPP QKRMRRDWDEHSSDPYHSGYEMPYAG | 102 | 9 |
| Q92560 | Ubiquitin carboxyl-terminal hydrolase BAP1 (BRCA1-associated protein 1)¥ | N | 685 | EGMLANLVEQNISVRRRQGVSIGRL HKQRKPDRRKRSRPYKAKRQ | 729 | 10 |
| P48634 | Large proline-rich protein BAT2 (HLA-B-associated transcript 2) | C, N | 690 | VPAPQAPPPPPKALYPGALGRP PPMPPMNFDPRWMMIPPYVDPRLLQGRP | 739 | 11 |
| O15178 | Brachyury protein | N | 251 | TSTLCPPANPHPQFGGALSLP STHSCDRYPTLRSHRSSPYPSPYAHRNNS | 300 | 12 |
| O60885 | Bromodomain-containing protein 4 (HUNK1 protein) | N | 1015 | QGQQPPHPPPGQQPPPPQPAKP QQVIQHHHSPRHHKSDPYSTGHLREAPSP | 1064 | 13 |
| Q14004 | Cell division cycle 2-like protein kinase 5 | not known | 376 | YERGGDVSPSPYSSSSWRRSRSPYSPV LRRSGKSRSRSPYSSRHSRSRSR | 425 | 14 |
| Q9NYV4 | Cell division cycle 2-related protein kinase 7 | N | 256 | SSNYDSYKKSPGSTSRRQSVSPP YKEPSAYQSSTRSPSPYSRRQRSVSPY | 305 | 15 |
| Q5TG10 | Protein C6orf168 | not known | 94 | IDSKDAIILHQFARPNNGVPSLSPF CLKMETYLRMADLPYQNYFGGKLSA | 143 | 16 |
| P49761 | Dual specificity protein kinase CLK3 (CDC-like kinase 3/Clk3)¥ | N | 18 | YRWKRRRSYSREHEGRLRYPSRR EPPPRRSRSRSHDRLPYQRRYRERRDS | 67 | 17 |
| P05997 | Collagen alpha-2(V) chain precursor | not known | 611 | MGLPGPKGSNGDPGKPGEAGNPGVP GQRGAPGKDGKVGPYGPPGPPGLRG | 660 | 18 |
| Q03692 | Collagen alpha-1(X) chain precursor | not known | 84 | GYGSPGLQGEPGLPGPPGPSAVGKP GVPGLPGKPGERGPYGPKGDVGPAG | 133 | 19 |
| Q8TBR5 | Protein C19orf23¥ | not known | 70 | TWQTRNHTRTGHAYPRFTRPSFP SCNRNGKRRKLRLGLPY | 119 | 20 |
| Q96RT6 | Protein cTAGF-2 | not known | 692 | PPGTVFGASPDYFSPRDVPGPP RAPFAMRNVYLPRGFLPYRPPRPAFFPQ | 741 | 21 |

TABLE 3-continued

Predicted Kapβ2 substrates with hydrophobic PY-NLSs.

| Acc. No. | Name | Local.§ | N-term. Res. | Sequences for candidate Hydrophobic PY-NLS¶ | C-term. Res. | SEQ ID NO: |
|---|---|---|---|---|---|---|
| Q9NSV4 | Protein diaphanous homolog 3 (Diaphanous-related formin-3) | not known | 1070 | GAAFRDRRKRTPMPKDVRQSLSPM SQRPVLKVCNHGNKPYL | 1110 | 22 |
| P56177 | Homeobox protein DLX-1 | N | 44 | CLHSAGHSQPDGAYSSASSFSRP LGYPYVNSVSSHASSPYISSVQSYPGS | 93 | 23 |
| O95147 | Dual specificity protein phosphatase 14/MAP kinase phosphatase 6 | not known | 156 | RQLIDYERQLFGKSTVKMVQTPYGIV PDVYEKESRHLMPYWGI | 200 | 24 |
| Q9BUP0 | EF-hand domain-containing protein 1 (Swiprosin-2) | not known | 42 | PPARAPTASADAELSAQLSRR LDINEGAARPRRCRVFNPYTEFPEFSRRL | 91 | 25 |
| Q6ZV73 | FYVE, RhoGEF and PH domain-containing protein 6 (Zinc finger FYVF domain-containing protein 24) | C | 269 | SSELEALENGKRSTLISSDGVSKK SEVKDLGPLEIHLVPYTPKFPTPKPR | 318 | 26 |
| Q92837 | Proto-oncogene FRAT1 | N | 89 | PAVPLLLPPALAETVGPAPPGVL RCALGDRGRVRGRAAPYCVAELATGPS | 138 | 27 |
| Q96AF4 | FUSE-binding protein 1/DNA helicase V | N | 465 | PGPHGPPGPPGPGTPMGPYNPAPY NPGPPGPAPHGPPAPYAPQGWGNAYP | 514 | 28 |
| Q8NEA6 | Zinc finger protein GLIS3 | N | 601 | LTAVDAGAERFAPSAPSPHHISPR RVPAPSSILQRTQPPYTQQPSGSHLK | 650 | 29 |
| Q8TEK3 | Histone H3-K79 methyltransferase | N | 775 | SPAKIVLRRHLSQDHTVPGRP AASELHSRAEHTKENGLPYQSPSVPGSMK | 824 | 30 |
| P35452 | Homeobox protein Hox-D12 (Hox-4H) | N | 175 | AGVASCLRPSLPDGKRCPCSPGRPAVG GGPGEARKKRKPYTKQQIAELEN | 224 | 31 |
| Q13422 | DNA-binding protein Ikaros (Lymphoid transcription factor LyF-1) | N | 254 | CKIGSERSLVLDRLASNVAKR KSSMPQKFLGDKGLSDTPYDSSASYEKEN | 303 | 32 |
| O43474 | Kruppel-like factor 4 (Epithelial zinc-finger protein EZF) (Gut-enriched Krueppel-like factor) | N | 218 | GKFVLKASLSAPGSEYGSPSVI SVSKGSPDGSHPVVVAPYNGGPPRTCPK | 267 | 33 |
| Q8NEZ4 | Histone-lysine N-methyltransferase, H3 lysine-4 specific MLL3 | N | 2427 | NVNQAFTRPPPPYPGNIRSPVAPP LGPRYAVFPKDQRGPYPPDVASMGMR | 2476 | 34 |
| Q96G25 | Mediator of RNA polymerase II transcription subunit 8 homolog (ARC32). | N | 227 | GAPSQQQPMLSGVQMAQAGQPGKM PSGIKTNIKSASMHPYQR | 268 | 35 |
| Q93074 | Mediator of RNA polymerase II transcription subunit 12 | N | 1854 | DLLHHPNPGSITHLNYRQGSIGLY TQNQPLPAGGPRVDPYRPVRLPMQKL | 1903 | 36 |
| O43312 | Metastasis suppressor protein 1 (Metastasis suppressor YGL-1) | not known | 379 | LPRVTSVHLPDYAHYYTIGEGMF PSSQIPSWKDWAKPGPYDQPLVNTLQR | 428 | 37 |
| Q13310 | Polyadenylate-binding protein 4 | C | 484 | GAAQQGLTDSCQSGGVPTAVQNLAPR AAVAAAAPRAVAPYKYASSVRSPH | 533 | 38 |
| Q9Y6V0 | Piccolo protein (Aczonin) | C | 2874 | VVYKLPFGRSCTAQQPATTLPEDRFGYR DDHYQYDRSGPYGYRGIGGMKP | 2923 | 39 |

TABLE 3-continued

Predicted Kapβ2 substrates with hydrophobic PY-NLSs.

| Acc. No. | Name | Local.§ | N-term. Res. | Sequences for candidate Hydrophobic PY-NLS¶ | C-term. Res. | SEQ ID NO: |
|---|---|---|---|---|---|---|
| Q8NFH8 | RalBP1-associated Eps domain-containing protein 2 (RalBP1-interacting protein 2) | C | 188 | PTMSPLASPPSSPPHYQRVPLSHGYSKL RSSAEQMHPAPYEARQPLVQPE | 237 | 40 |
| O75177 | SS18-like protein 1 (SYT homolog 1) | not known | 196 | SHYSSAQGGSQHYQGQSSIAMM GQGSQGSSMMGQRPMAPYRPSQQGSSQQ | 245 | 41 |
| Q92922 | SWI/SNF complex 155 kDa subunit (BRG1-associated factor 155) | C, N | 960 | QQQHGQNPQQAHQHSGGPGLAPL GAAGHPGMMPHQQPPPYPLMHHQMPPP | 1009 | 42 |
| P09012 | U1 small nuclear ribonucleoprotein A (U1 snRNP protein A) | N | 123 | AVQGGGATPVVGAVQGPVPGMP PMTQAPRIMHHMPGQPPYMPPPGMIPPP | 172 | 43 |
| P18583 | SON3/Negative regulatory element-binding protein/DBP-5 | N | 945 | GQDPYRLGHDPYRLTPDPYRMSPR PYRIAPRSYRIAPRPYRLAPRPLMLA | 994 | 44 |
| Q8IXZ3 | Transcription factor Sp8 (Specificity protein 8) | N | 164 | GGSSAHSQDGSHQPVFISKV HTSVDGLQGIYPRVGMAHPYESWFKPSHPG | 213 | 45 |
| Q15532 | SSXT protein (SYT protein) | not known | 214 | QYNMPQGGGQHYQGQQPPMGMM GQVNQGNHMMGQRQIPPYRPPQQGPPQQ | 263 | 46 |
| Q9UMS6 | Synaptopodin-2 (Myopodin) | C, N | 931 | PSYPLAALKSQPSAAQPSKMGKK KGKKPLNALDVMKHQPYQLNASLFTFQ | 980 | 47 |
| Q9Y5Q8 | (Genethonin 2)¥ General transcription factor 3C polypeptide 5 | N | 31 | GVVRDVAKMLPTLGGEEGVSRI YADPTKRLELYFRPKDPYCHPVCANRFS | 80 | 48 |
| Q04206 | Transcription factor p65 (Nuclear factor NF-kappa-B p65 subunit) | C, N | 310 | KSIMKKSPFSGPTDPRPPPRRIAVP SRSSASVPKPAPQPYPFTSSLSTIN | 359 | 49 |
| Q9NRE2 | Teashirt homolog 2 (Zinc finger protein 218) (Ovarian cancer-related protein 10-2) | N | 558 | LPMGSRVLQIRPNLTNKLRPIAPK WKVMPLVSMPTHLAPYTQVKKESEDK | 607 | 50 |
| Q9UJT2 | Testis-specific serine kinase substrate | not known | 275 | PAATSQGCPGPPGSPDKPSRPHGLV PAGWGMGPRAGEGPYVSEQELQKLF | 324 | 51 |
| Q8TAP9 | TTD nonphotosensitive 1 protein | N | 15 | GPGGGGWGSGSSFRGTPGGGGPRPPSPR DGYGSPHHTPPYGPRSRPYGSS | 64 | 52 |
| Q96151 | Williams-Beuren syndrome chromosome region 16 protein (WBS16) | N | 62 | FVWGFSFSGALGVPSFVVPSSGPGPR AGARPRRIQPVPYRLELDQKISS | 111 | 53 |
| P19544 | Wilms' tumor protein (WT33) | N | 94 | VHFSGQFTGTAGACRYGPFGPP PPSQASSGQARMFPNAPYLPSCLESQPA | 143 | 54 |
| P17861 | X box-binding protein 1 (XBP-1) (Tax-responsive element-binding protein 5) | N | 202 | ISCWAFWTTWTQSCSSNALPQSLPAWR SSQRSTQKDPVPYQPPFLCQWGR | 251 | 55 |
| Q8NAP3 | Zinc finger and BTB domain-containing protein 38 | N | 539 | HAIDHRLSISKKTANGGLKPSVY PYKLYRLLPMKCKRAPYKSYRNSSYEN | 588 | 56 |
| Q9C0A1 | Zinc finger homeobox protein 2 | N | 784 | VKPPATATPASLPKFNLLLGKV DDGTGREAPKREAPAFPYPTATLASGPQ | 833 | 57 |

§As annotated in the UniProtKB/Swiss-Prot entries. C represents cytoplasm and N represents nucleus.
¶Central hydrophobic motifs are colored yellow and the R/K/H-PY motifs are colored red.
¥Substrates also identified using bPY-NLS motif.

For example, protein kinase Clk3 (P49761), transcription factors HCC1 (Q14498), mRNA processing protein RB15B (Q8NDT2) and Sox14 (O95416), and the Williams-Beuren syndrome chromosome region 16 protein/WBS16 (Q96I51) and showed that both their predicted NLSs and the full length proteins (except for RB15B, which could not be expressed in bacteria) bind Kapβ2 and can be dissociated by RanGTP (FIGS. 6D and 6E). Thus, the rules not only identify NLSs in known substrates, but also are highly effective in predicting entirely new substrates.

TABLE 4

Predicted Kapβ2 substrates with bPY-NLSs

| Accession No. | Name | Localization§ | N-term Residue | Sequences for candidate Hydrophobic PY-NLS¶ | C-term Residue | SEQ ID NO |
|---|---|---|---|---|---|---|
| Q13023 | A-kinase anchor protein 6 (AKAP 100) | not available | 1851 | GSVKRVSENNGNGKNSSHTHELGTKRENKKTIFKVNKDPYVADMENGNIE | 1900 | 58 |
| Q9BXP5 | Arsenite-resistance protein 2¥ | not available | 61 | NRRERFSPPRHELSPPQKRMRRDWDEHSSDPYHSGYEMPYAGGGGGPTYG | 110 | 59 |
| Q92560 | BRCA1-associated protein 1¥ | N | 685 | EGMLANLVEQNISVRRRQGVSIGRLHKQRKPDRRKRSRPYKAKRQ | 729 | 60 |
| Q9NYF8 | Bcl-2-associated transcription factor 1 | C, N | 32 | KRYSSRSRSRTYSRSRSRDRMYSRDYRRDYRNNRGMRRPYGYRGRGYY | 81 | 61 |
| Q9ULD4 | Bromodomain and PHD finger-containing protein 3 | not available | 1 | MRKPRRKSRQNAEGRRSPSPYSLKCSPTRET | 31 | 62 |
| Q9UK58 | Cyclin-L1 Protein C5orf5 | N | 337 | ASKPSSPREVKAEEKSPISINVKTVKKEPEDRQQASKSPYNGVRKDSKRS | 386 | 63 |
|  | (GAP-like protein N61) | not available | 531 | QRFLHDPEKLDSSSKALSFTRIRRSSFSSKDEKREDRTPYQLVKKLQKKI | 580 | 64 |
| Q9NYF5 | CDC-like kinase 3¥ | N | 62 | RERRDSDTYRCEERSPSFGEDYYGPSRSRHRRRSRERGPYRTRKHAHHCH | 111 | 65 |
| P49761 | Protein C19orf23¥ | not available | 70 | TWQTRNHTRTGHAYPRFTRPSFPSCNRNGKRRKLRLGLPY | 109 | 66 |
| Q8TBR5 | Zinc-finger protein neuro-d4 | C, N | 156 | EDLEDDIPRRKNPAKGKAYGIGGLRKRQDTASLEDRDKPYVCDKFYKELA | 205 | 67 |
| Q92782 | Forkhead box protein E1/Thyroid transcription factor 2 | N | 17 | TVKEERGETAAGAGVPGEATGRGAGGRRRKRPLQRGKPPYSYIALIAMAI | 66 | 68 |
| O00358 | Forkhead box protein F3 (FKHL12) (Forkhead-related transcription factor 8) | N | 35 | AEPGREPEEAAAGRGEAAPTPAPGPGRRRRRPLQRGKPPYSYIALIAMAL | 84 | 69 |
| Q13461 | Forkhead box protein F1 | N | 1 | MDPASSGPSKAKKTNAGIRRPEKPPYSYIALTVMAI | 36 | 70 |
| O75593 | Forkhead box protein | N | 1 | MGPCSGSRLGPPEAESPSQPPKRRKKRYLRHDKPPYTYLAMIALVI | 46 | 71 |
| O75593 | H1/Forkhead activin signal transducer 1 |  |  |  |  |  |
| Q9UPW0 | Forkhead box proteinJ3 | N | 142 | SKDDPGKGSYWAIDTNPKEDALPTRPKKPARSVERASTPYSIDSDSLGME | 191 | 72 |
| P55317 | Hepatocyte nuclear factor 3-alpha (Forkhead box protein A1). | N | 135 | MNPCMSPMAYAPSNLGRSPAGGGDAKTFKRSYPHAKPPYSYISLITMAI | 184 | 73 |
| P55318 | Hepatocyte nuclear factor 3-gamma (Forkhead box protein A3) | N | 81 | LGVSGGSSSSGYGAPGPGLVHGKEMPKGYRRPLAHAKPPYSYISLITMAI | 130 | 74 |

TABLE 4-continued

Predicted Kapβ2 substrates with bPY-NLSs

| Accession No. | Name | Localization§ | N-term Residue | Sequences for candidate Hydrophobic PY-NLS¶ | C-term Residue | SEQ ID NO |
|---|---|---|---|---|---|---|
| Q9Y483 | Metal-response element-binding transcription factor 2 | N | 370 | HEFIGKGRKASKPISDSREVSNGIEKKGKKKSVGRPPGPYTRKMTQKTAE | 419 | 75 |
| O95644 | NFAT transcription complex cytosolic component | C, N | 238 | PSTSPRASVTEESWLGARSSRPASPCNKRKYSLNGRQPPYSPHHSPTPSP | 287 | 76 |
| Q9ULL1 | Pleckstrin homology domain-containing family G member 1 | not available | 1304 | SKFVDADFSDNVCSGNTLHSLNSPRTPKKPVNSKLGLSPYLTPYNDSDKL | 1353 | 77 |
| Q99575 | Ribonucleases P/MRP protein subunit POP1 | N | 372 | QTELPDEKIGKKRKRKDDGENAKPIKKIIGDGTRDPCLPYSWISPTTGII | 421 | 78 |
| Q8NEY8 | Periphilin 1/Gastric cancer antigen Ga50 | C, N | 84 | YRWTRDDHSASRQPEYRDMRDGFRRKSFYSSHYARERSPYKRDNTFFRES | 133 | 79 |
| Q8NDT2 | RNA-binding protein 15B | N | 245 | SRSGERWGADGDRGLPKPWEERRKRRSLSSDRGRTTHSPYEERSRTKGSG | 294 | 80 |
| Q14498 | Splicing factor HCC1 | N | 60 | DRERKKSKSRERKRSRSKERRRSRSRSRDRRFRGRYRSPYSGPKFNSAIR | 109 | 81 |
| P62241 | 40S ribosomal protein S8 | N | 1 | GISRDNWHKRRKTGGKRKPYHKKRKYELGR | 30 | 82 |
| O95416 | Transcription factor SOX-14 | N | 59 | DEAKRLRAQHMKEHPDYKYRPRRKPKNLLKKDRYVFPLPYLGDTDPLKAA | 108 | 83 |
| Q9Y651 | Transcription factor SOX-21 (SOX-A) | N | 59 | DEAKRLRAMHMKEHPDYKYRPRRKPKTLLKKDKFAFPVPYGLGGVADAEH | 108 | 84 |
| O00267 | Transcription elongation factor SPT5 | N | 678 | GGQRGGFGSPGGGSGGMSRGRGRRDNELIGQTVRISQGPYKGYIGVVKDA | 727 | 85 |
| Q9UMS6 | Synaptopodin-2 (Myopodin) (Genethonin 2)¥ | C, N | 931 | PSYPLAALKSQPSAAQPSKMGKKKGKKPLNALDVMKHQPYQLNASLFTFQ | 980 | 86 |
| Q8IWR0 | Zinc finger CCCH-type domain-containing protein 7A | N | 464 | ANIDHKCKKDILIGRIKNVEDKSWKKIRPRPTKTNYEGPYYICKDVAAEE | 513 | 87 |
| Q9H091 | Zinc finger MYND domain-containing protein 15 | not available | 522 | RDSLEVSVRPGSGISARPSSGTKEKGGRRDLQIKVSARPYHLFQGPKPDL | 571 | 88 |
| Q9H116 | Zinc finger protein 336 | N | 177 | LTDSLDYPGERASNGMSSDLPPKKSKDKLDKKKEVVKPPYPKIRRASGRL | 226 | 89 |
| Q8N895 | Zinc finger protein 366 | N | 49 | RGPFSQFRYEPPPGDLDGFPGVFEGAGSRKRKSMPTKMPYNHPAEEVTLA | 98 | 90 |

§As annotated in the UniProtKB/Swiss-Prot entries. C represents cytoplasm and N represents nucleus.
¶Central basic-enriched regions are colored blue and the R/K/H-PY motifs are colored red.
¥Substrates also identified using hPY-NLS motif.

Of the 81 candidate Kapβ2 substrates, 48 contain hPY-NLSs (e.g., Table 3), 28 contain bPY-NLSs (e.g., Table 4) and 5 contain PY-NLSs with both basic and hydrophobic central motifs. 49 of the new substrates (about 60%) are involved in transcription or RNA processing, 18 have unknown cellular activity and the rest are involved in signal transduction (8), cell cycle regulation (3) and the cytoskeleton (3). Interestingly, information on subcellular localization is available for about 62 of the predicted substrates, of which about 57 (about 92%) are annotated to have nuclear localization. The SwissProt database used in the search is the most highly annotated and non-redundant protein database, but it is still incomplete for human proteins (Apweiler et al., 2004). Thus, the number of new Kapβ2 substrates listed in Tables 3 and 4 is a lower limit of the complete set of Kapβ2 import substrates. The large number of Kapβ2 substrates currently predicted by our NLS rules already implies the generality and prevalence of PY-NLSs. Kapβ1 and Crm1 are also involved in mitosis and centrosome duplication ((Arnaoutov et al., 2005) and reviewed in (Budhu and Wang, 2005; Harel and Forbes, 2004; Mosammaparast and Pemberton, 2004)), suggesting that many other Kapβs may be similarly involved in multiple cellular functions in addition to nuclecytoplasmic transport. Thus, Kapβ2 substrates will likely include ligands responsible for other still unknown cellular functions of Kapβ2 as well as large numbers of cargoes for nuclear import.

Figure 7:
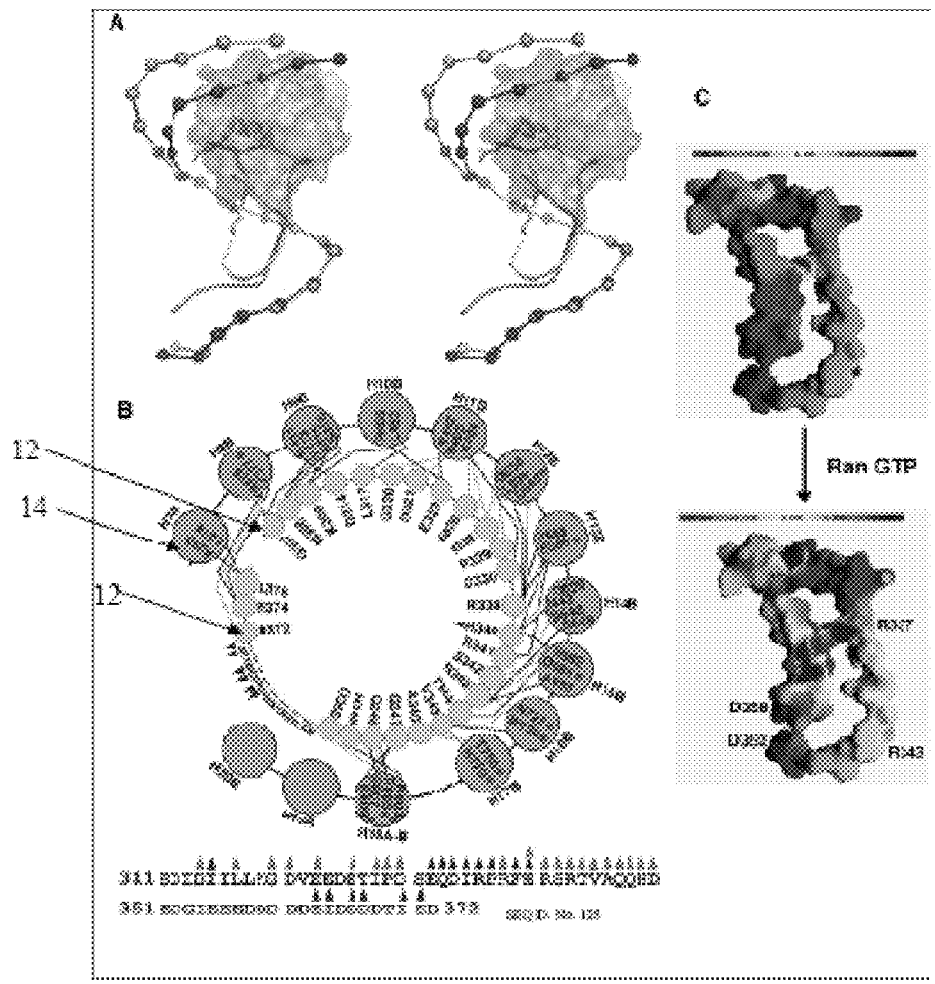
FIGS. 7A-C are comparisons of Kapβ2-M9NLS and Kapβ2-Ran complexes, SEQ ID NO.: 125.

Mechanism of Ran-mediated substrate dissociation from Kapβ2. FIGS. 7A-C are comparisons of Kapβ2-M9NLS and Kapβ2-Ran complexes. FIG. 7A is a stereo diagram of Kapβ2-M9NLS complex superimposed on the Ran complex. Kapβ2s are drawn as spheres at the geometric center of each HEAT repeat and the H8 loops are drawn as ribbons. In the M9NLS complex, Kapβ2 is red and substrate green. In the Ran complex, Kapβ2 is light brown and its H8 loop is yellow. The molecular surface of RanGTP is shown in blue. FIG. 7B is a diagram of the contacts (<4.0 Å) between the H8 loop and the C-terminal arch of Kapβ2 in the Ran state with the sequence of the H8 loop shown at bottom. Yellow circles are loop residues 12 that contact the Kapβ2 arch pink circles 14 are Kapβ2 helices. Red dashed lines indicate intervening loop residues that do not contact the Kapβ2 arch. Blue triangles label residues that contact Ran, pink triangles label residues that contact the Kapβ2 arch and red circles label Kapβ2 residues that also contact M9NLS. Polar contacts are shown with green lines and hydrophobic contacts with black lines. FIG. 7C is an image of the electrostatic surface potential of the H8 loop in the presence and absence of RanGTP, drawn with GRASP (Nicholls et al., 1991). Top: Molecular surface of the isolated H8 loop (Kapβ2 residues 310-372, Kapβ2-Ran complex 1QBK). RanGTP and the Kapβ2 superhelix are omitted from the electrostatic calculation to approximate charges of the loop in the absence of Ran. Bottom: molecular surface of the H8 loop with electrostatic surface potential calculated using both RanGTP and the H8 loop to represent the Ran-bound state.

The interaction of RanGTP with Kapβ2 to dissociate substrates in the nucleus is a crucial step in nuclear import. Structural comparison of Kapβ2s in the M9NLS and RanGTP complexes (Chook and Blobel, 1999) show large differences in their H8 loops (FIG. 7A), and finally reveal the mechanism of Ran-mediated substrate dissociation. In the Kapβ2-Ran structure, the H8 loop makes extensive contacts with both Ran and the Kapβ2 C-terminal arch as seen in FIGS. 7A and 7B (Chook and Blobel, 1999). In fact, much of the H8 loop is sequestered in the C-terminal arch such that loop residues 338-350 occupy the same binding site as M9NLS residues 268-281. In contrast, proteolysis studies have suggested that the loop is exposed when Ran is absent (Chook et al., 2002) and this is confirmed by the Kapβ2-M9NLS structure. Even though the H8 loop in the M9NLS complex is truncated, only 14 of its 32 residues are observed, indicating disorder in much of the loop. Ordered loop residues include 312-319 that emerge from helix H8A and residues 369-374 that precede helix H8B (FIGS. 2A and 2B). The former are in similar positions in both complexes, but the latter has shifted to direct the loop away from the arch in the substrate complex in FIGS. 7A and 2B. In summary, the concave surface of the C-terminal arch is free to bind substrate when Ran is absent, but the H8 loop occupies the substrate binding site when Ran is present. Interestingly, most of the substrate binding site remains unchanged in both ligand-bound states with repeats 9-17 superimposing well at rmsd of 1.2 Å as seen in FIG. 7A. The mechanism of Ran-mediated substrate dissociation described here is a thermodynamic one. Ran may increase the dissociation rate of substrate, thus accelerating its release from Kapβ2. Alternatively, the system is limited by the intrinsic dissociation rate of the substrate, and Ran-induced changes in the loop prevent substrate rebinding once dissociation has occurred.

Figure 8:
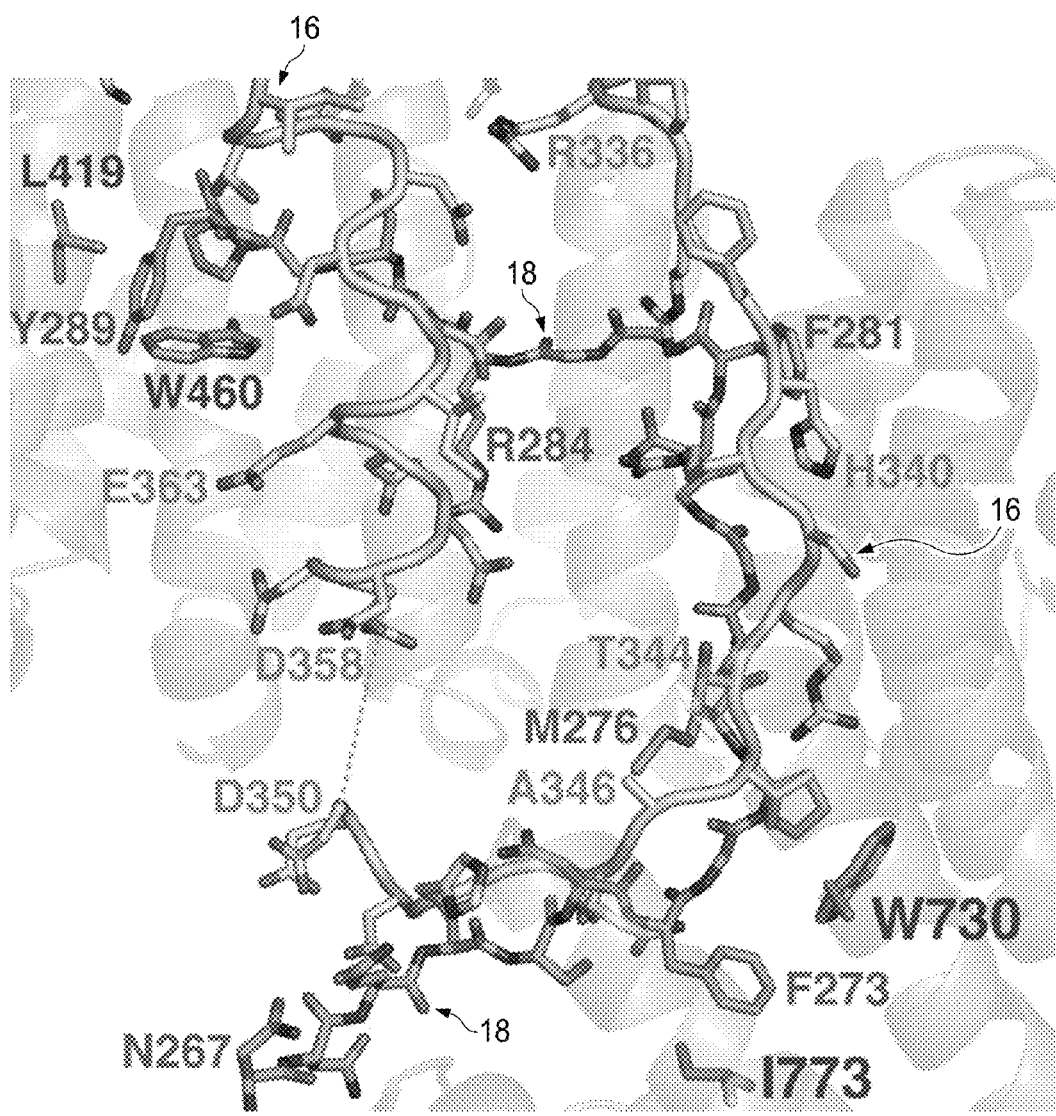
FIG. 8 is an image of a superposition of the Kapβ2-M9NLS and Kapβ2-Ran complexes.

FIG. 8 is an image of a superposition of the Kapβ2-M9NLS and Kapβ2-Ran complexes, showing the spatial overlap between the Kapβ2 H8 loop in the Ran state 16 (yellow) and M9NLS 18 (green). Despite extensive spatial overlap between the Ran-bound H8 loop and M9NLS, they share no obvious sequence similarity. This is not surprising since they bind in antiparallel direction to each other and their backbones deviate in path even where spatial overlap is greatest (loop residues 338-350 and M9NLS residues 268-281; FIG. 8). However, the H8 loop obviously contains a linear epitope that binds Kapβ2 and raises the possible existence of a different class of NLSs.

The calculated electrostatic surface potential of the H8 loop in the presence and absence of RanGTP is distinct as seen in FIG. 7C. The H8 loop contains many acidic residues, particularly through $^{351}$EDGIEEEDDDDDEIDDDD$^{368}$ (SEQ ID NO: 91) directly C-terminal to residues 338-350 which overlap with M9NLS. Negative charges here may prevent binding of the loop to the acidic C-terminal arch in FIG. 7C, top. When Ran binds Kapβ2, its basic patch (K127, R129, K132, K134, R140, K141 and K159) interacts with H8 loop residues 332-340 and 363-371. Again, long-range electrostatic effects of the basic interface of Ran may substantially decrease the negative charge of the loop, converting residues 338-350 into a more suitable ligand for the Kapβ2 substrate binding site in FIG. 7C, bottom. Ran probably also imparts conformational constraints to orient the H8 loop in the substrate site. The relative importance of electrostatic versus conformational effects of Ran binding is not known. Biophysical studies of H8 loop mutants with varying charge and H8 loop peptides in trans will be crucial to parse the different effects of Ran on the loop.

Another structural difference between the Kapβ2-M9NLS and Kapβ2-Ran complexes is found at the N-terminal arches as seen in FIG. 7A. Small changes in the orientation of α-helices within and between HEAT repeats 1-10 result in a maximum displacement of over about 23 Å at the N-terminus. The M9NLS complex in the crystal cannot accommodate RanGTP but biochemical studies had shown that Kapβ2 can adopt a Ran-competent conformation when bound to substrate in solution (Chook et al., 2002). The two Kapβ2-M9NLS complexes in the asymmetric unit also diverge structurally with high B-factors at the N-terminal four repeats, suggesting inherently flexibility in that region. Many Kapβs have been shown to exhibit structural plasticity and adopt multiple conformations (Fukuhara et al., 2004). The Kapβ2-M9NLS crystals have trapped a conformation of the N-terminal arch that is incompetent for Ran-binding.

Many other Kapβs contain large insertions like the Kapβ2 H8 loop. Kapβ1 has a short 15-residue acidic loop in repeat 8 (Cingolani et al., 1999; Lee et al., 2005), Cse1 has a 2-helix insertion in repeat 8 (Cook et al., 2005; Matsuura and Stewart, 2004) and Crm1, Kapβ3, Imp4, Imp7, Imp8, Imp9 and Imp11 are all predicted to have large insertions in their central repeats. Mutational studies of the predicted Crm1 insertion suggest that it also directly couples Ran and substrate binding (Petosa et al., 2004). However, in Kapβ1 and Cse1, the mechanisms of substrate dissociation appear distinct from those in Kapβ2 and Crm1. Kapβ1 binds three different substrates in three different binding sites, and RanGTP causes a drastic change in superhelical shape that distorts binding sites of substrates Kapα and SREBP-2 while directly displacing substrate PTHrP from the N-terminal arch (Cingolani et al., 2002; Cingolani et al., 1999; Lee et al., 2005; Lee et al., 2003). Similarly, the Cse1 insertion is a pivot point for global conformational change like that in Kapβ1 (Cook et al., 2005). Trends for coupling Ran and substrate binding in the Kapβ family are emerging. Kapβ2 and probably Crm1 employ a large insertion to directly couple the two ligands with little conformational change in the substrate binding site. In contrast, Kapβ1 and Cse1 use large-scale conformational changes to transition from closed substrate-free to open substrate-bound conformations.

Protein expression, purification and complex formation. In the crystallographic studies Kapβ2 residues 337-367 were replaced with a GGSGGSG linker (SEQ ID NO: 1). This protein was expressed in E. coli BL21 (DE3) as a GST-fusion from pGEX-Tev vector and purified as previously reported (Chook and Blobel, 1999; Chook et al., 2002). M9NLS was expressed in E. coli as a GST-fusion of hnRNP A1 residues 257-305, and purified as previously described (Chook et al., 2002). Two-fold molar excess of GST-M9NLS was added to purified Kapβ2, cleaved with Tev protease and the complex purified by gel filtration chromatography. Selenomethionine-Kapβ2 and selenomethionine-M9NLS were purified and assembled as for the native proteins. All complexes were concentrated to 25 mg/ml for crystallization.

Crystallization, data collection and structure determination. Native Kapβ2-M9NLS complex was crystallized by vapor diffusion (e.g., reservoir solution: about 40 mM MES pH about 6.5, about 3M potassium formate and about 10% glycerol) and flash frozen in liquid propane. These crystals diffracted at best to about 3.5 Å. However, soaking the crystals in crystallization solution containing about 0.7 mM of a 12-residue FXFG-peptide (sequence: TGGFTFGTAKTA (SEQ ID NO: 92)) improved diffraction to about 3.05 Å. Data from an FXFG-soaked crystal was collected on the X-ray Operations and Research beamline 19-ID at the Advanced Photon Source, Argonne National Laboratory and processed using HKL2000 (Otwinowski and Minor, 1997) (Table 1). Crystals of the selenomethionine complex were also obtained by vapor diffusion (reservoir solution: about 0.1M Tris about 8.0, about 3M potassium formate and about 15% glycerol), soaked in FXFG-peptide and diffracted to about 3.3 Å. Single-wavelength anomalous dispersion (SAD) data was collected on SBC-19-ID (Table S1) and processed with HKL2000 (Otwinowski and Minor, 1997).

Native Kapβ2-M9NLS crystals (space group C2, unit cell parameters a=152.0 Å, b=154.1 Å, c=141.7 Å and β=91.7°) contain two complexes in the asymmetric unit. Selenomethionine Kapβ2-M9NLS also crystallized space group C2, but has a significantly different unit cell length in its a axis (unit cell parameters: a=155.6 Å, b=154.6 Å, c=141.6 Å and β=91.6°; Table 1). Native Patterson maps indicate that the two complexes in the asymmetric unit are related by pseudo-translation along the crystallographic c axis. Molecular replacement trials using the Kapβ2-Ran structure were unsuccessful but SAD phasing followed by solvent flipping, both using the program CNS produced interpretable electron density maps (Brunger et al., 1998). A model comprising 90% of Kapβ2 was built using O (Jones et al., 1991) but electron density for the substrate remained uninterpretable even though M9NLS residue M276 could be clearly placed using a selenium site. The partial SAD-phased model was used as a search model for molecular replacement using the program Phaser with the higher resolution native dataset (McCoy et al., 2005). Positional refinement using REFMAC5 (CCP4, 1994) followed by solvent flipping using CNS (Brunger et al., 1998) yielded electron density maps that allowed about 97% of Kapβ2 to be built. The density was further improved by rigid body, positional and simulated annealing refinement of Kapβ2 alone, using the programs CNS (Brunger et al., 1998). The Fo-Fc map plotted at about 2.5 sigma clearly showed strong density for M9NLS residues 267-289 in the complex I, and residues 263-289 in complex II (FIG. 1c). Even though soaking the crystals in FXFG peptide improved diffraction, no density was observed for the FXFG peptide. The final refined model shows good stereochemistry with Rfactor of about 24.0% and Rfree of about 25.0%.

NLS-mapping, site directed mutagenesis and Kap β2 binding assays. cDNA for hnRNPs F, M, PQBP-1, EWS, SAM68, HMBA-inducible protein, YBP1, FUS, DDX3, Clk3, Sox14 and WBS16 were obtained from Open Biosystems. cDNA for HCC1 and RB15B were obtain by PCR from a human fetal thymus cDNA library (Clontech). The full-length proteins as well as fragments listed in FIGS. 3c and S3b were sub-cloned using PCR into pGEX-Tev vector. Expression constructs for NLSs of cyclin T1 and CPSF6 were generated using synthetic complementary oligonucleotides coding for the 28-mer peptides. Single, double and triple mutations to alanine residues were performed using the QUICKCHANGE® method (Stratagene), and all constructs were confirmed by nucleotide sequencing. Substrate proteins were expressed in E. coli BL21 (DE3) cells. GST-M9NLS was expressed at about 37° C., GST-Kapβ2 was expressed at about 30° C. and the other substrates were expressed at about 25° C., and all were purified using glutathione sepharose (GE Healthcare).

In each binding reaction involving new NLSs, mutant NLSs and new Kapβ2 substrates, about 18 μg of Kapβ2 were added to about 5-10 μg of GST-substrate immobilized on glutathione sepharose followed by extensive washing of the beads with buffer containing about 20 mM Hepes pH about 7.3, about 110 mM potassium acetate, about 2 mM DTT, about 1 mM EGTA, about 2 mM Magnesium acetate and about 20% glycerol. Immobilized proteins were visualized using SDS-PAGE and Coomassie Blue staining. 3-5 fold molar excess of RanGTP (compared to Kapβ2) is also used in some binding assays. Binding assays involving mutants of Kapβ2 were performed similarly, with each reaction using approximately 10 μg of MBP-M9NLS added to about 5-10 μg of GST-Kapβ2.

Quantitation of binding affinity with ITC Binding affinities of wild type and mutant MBP-M9NLS to Kapβ2 were quantitated using ITC. The ITC studies used a MicroCal Omega VP-ITC calorimeter (MicroCal Inc., Northampton, Mass.). Proteins were dialyzed against buffer containing 20 mM Tris pH 7.5, 100 mM NaCl and 2 mM β-mercaptoethanol. 100-500 μM Wild type and mutant MBP-M9NLS proteins were titrated into a sample cell containing 10-100 μM full length Kapβ2. Most ITC studies were done at 20° C. with 35 rounds of about 8 μl injections. ITC studies involving wild type M9NLS were similar, but with 56 rounds of about 5 μl injections. Data was plotted and analyzed using MicroCal Origin software version 7.0, with a single binding site model.

Bioinformatics search for new Kapβ2 substrates. Candidate Kapβ2 substrates were identified by the program ScanProsite (Gattiker et al., 2002) using motifs φ1-G/A/S-φ3-φ4-X7-12-R/K/H-X2-5-P-Y (SEQ ID NO: 93) (where φ1 is strictly hydrophobic, φ3 and φ4 are hydrophobic and also includes long aliphatic sidechains R and K), K/R-X0-2-K/R-K/R-X3-10-R/K/H-X1-5-P-Y (SEQ ID NO: 94) and human proteins in the UniProtKB/Swiss-Prot protein database (Bairoch et al., 2004). All resulting entries were filtered for structural disorder using the program DisEMBL (Linding et al., 2003) and for positively charged NLS segments of 50 amino acids (beginning 40 residues N-terminus of the PY to 10 residues C-terminus of that motif). Proteins with potential PY-NLSs that are found in transmembrane proteins and those that occur within identified domains were eliminated from the list even though some NLSs may occur in long loops within folded domains.

Karyopherinβs/Kapβs/Importinβs mediate trafficking of human proteins into the cell nucleus through recognition of distinct NLSs (Mosammaparast, et al. 2004). Large panels of import-substrates are known only for Kapβ1/Importinβ and Kapβ2/Transportin (Mosammaparast, et al. 2004; Lee, et al. 2006). Crm1 inhibitor Leptomycin B has been critical for identifying many Crm1 substrates (Hamamoto, et al. 1983; Yashiroda, et al. 2003).

NLSs include short basic classical-NLSs that bind heterodimer Kapα/Kapβ1 (Mosammaparast, et al. 2004; Dingwall, et al. 1991), and newly identified PY-NLSs that bind Kapβ2 (Lee, et al. 2006). PY-NLSs are 20-30 residue signals with intrinsic structural disorder, overall basic character, C-terminal R/K/HX$_{2-5}$PY and N-terminal hydrophobic/basic motifs. These weak but orthogonal characteristics have provided substantial limits in sequence space to identify over 100 PY-NLS-containing human proteins (Lee, et al. 2006). Two subclasses, hPY- and bPY-NLSs, are defined by N-terminal motifs: hPY-NLSs contain φG/A/Sφφ motifs (φ, hydrophobic residue) whereas bPY-NLSs are enriched with basic residues.

The structure of human Kapβ2 bound to the hPY-NLS of heterogeneous nuclear ribonucleoprotein A1 (hnRNP A1) (Lee, et al. 2006) and the 3.1 Å crystal structure of human Kapβ2 bound to the bPY-NLS of human hnRNP M are known (Lee, et al. 2006; Datar, et al. 1993; Hase, et al. 2006; Gattoni, et al. 1996).

Protein expression, purification and complex formation. Human Kapβ2 (accession number AAB58254) was expressed in pGEX-Tev vector (pGEX-4T3 (GE Healthcare, UK) with a Tev cleavage site) as a GST fusion protein and purified as previously described (see Lee, et al. 2006) Residues 337-367 of Kapβ2 were replaced with a GGSGGSG linker (SEQ ID NO: 1) to obtain diffracting crystals. This truncation does not interfere with NLS binding. The NLS for human hnRNP M (accession number NM_005968) was expressed in BL21(DE3) *E. coli* cells as a GST-fusion protein spanning residues 41-70, and purified as described previously described (Chook, et al. 2002). GST-hnRNP M-NLS was mixed with Kapβ2 in a 3:1 molar ratio, treated with Tev protease and the resulting complex purified by gel filtration chromatography. The complex was concentrated to 20 mg/ml for crystallization.

NLS mutants were obtained by site directed mutagenesis using QUICKCHANGE ® (Stratagene, La Jolla, Calif.). Nucleotide sequencing was performed on all mutants. For ITC measurements, NLS wild type and mutant fragments were expressed as fusion proteins in pMAL-Tev vector (pMAL (New England Biolabs, UK) with Tev site). Expression and purification were similarly previous studied (Lee, et al. 2006).

Figure 9:
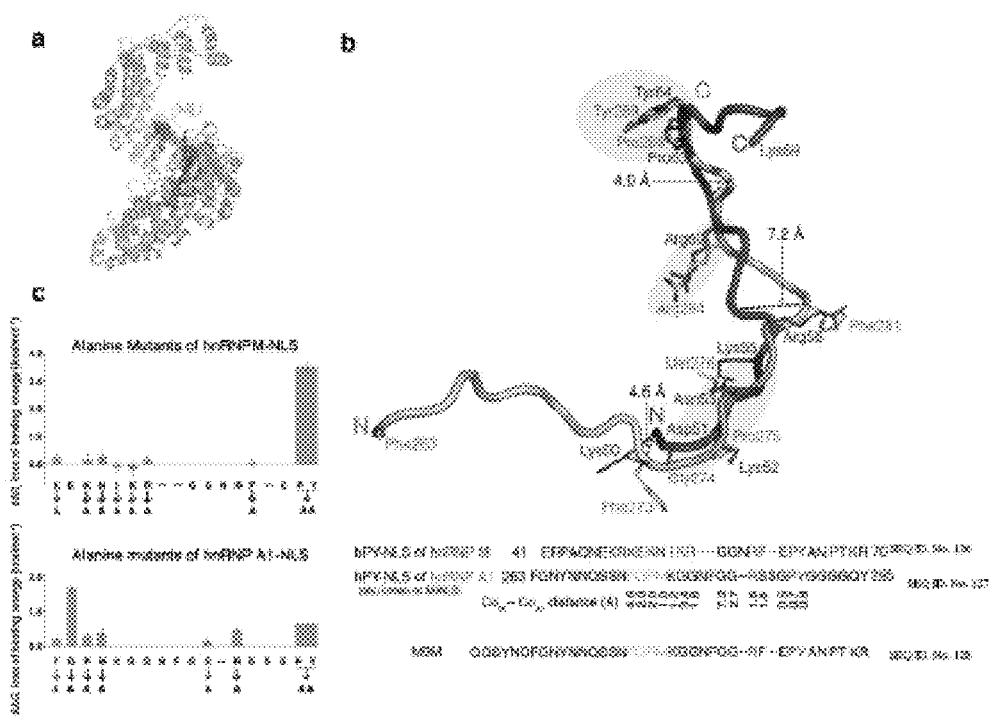
FIGS. 9A and 9B are images and 9C is a histogram that illustrate Kapβ2 bound to bPY-NLS of hnRNP M, in FIG. 9B, SEQ ID NOS: 126 to 128 and in FIG. 9C SEQ ID NOS.: 126 and amino acids 11 to 27 of SEQ ID NO.: 111.

FIGS. 9A-9C are images and histograms that illustrate Kapβ2 bound to bPY-NLS of hnRNP M. FIGS. 9A-9B are images of the 3.1 Å crystal structure of human Kapβ2 bound to the bPY-NLS of human hnRNP M to compare structures of consensus NLS motifs and to understand how diverse hydrophobic/basic N-terminal motifs are recognized by Kapβ2. FIG. 9A is a ribbon model of Kapβ2 (pink), hnRNP M-NLS (magenta) and the 2.5σ Fo-Fc map (blue).

Kapβ2-hnRNP M-NLS complex was crystallized by vapor diffusion using 100 mM HEPES pH 7.0, 2.7 M potassium formate and 10% glycerol in the reservoir solution. Crystals were flash frozen in liquid propane. 3.0 Å data from these crystals were collected at beamline 19-ID at the Advanced Photon Source, Argonne National Laboratory at X-ray wavelength 12.66 keV and temperature 100 K. Data was processed using HKL2000[3] (Otwinowski, et al. 1997). Kapβ2-hnRNP M-NLS crystals were in a very similar space group as the Kapβ2-hnRNP A1-NLS crystals (PDB ID: 2h4m[1]), with space group C2, unit cell parameters a=152.0 Å, b=154.1 Å, c=141.7 Å and β=91.7° and two complexes in the asymmetric unit.

The Kapβ2-hnRNP A1-NLS model was used as a search model for molecular replacement using the program Phaser (McCoy, et al. 2005). Positional refinement using REFMAC5 (CCP4. 1994) followed by solvent flipping using CNS (Brunger, et al. 1998) yielded electron density maps that allowed about 98% of the model to be built using Coot (Emsley, et al. 2004). The density was further improved using rigid body, positional and simulated annealing refinement of Kapβ2 alone, with programs in CNS. The same test data set was used throughout the entire refinement process.

The Fo-Fc map plotted at 2.5σ shows interpretable density for hnRNP M-NLS residues 49-53 and 55-68 in complex I, and residues 49-69 in complex II. The final refined model shows good stereochemistry with $R_{factor}$ of about 26.3% and $R_{free}$ of about 29.4%. Ramachandran plot for final model: about 90.7% in most favored and about 9.3% in allowed regions. The structure of the sample in FIGS. 9A-9B and FIG. 10B were drawn using PYMOL (DeLano (2002). Table 5 is a table of the data collection and refinement statistics:

TABLE 5

| | Kapβ2-hnRNP M-NLS |
|---|---|
| Data collection | |
| Space group | C2 |
| Cell dimensions | |
| a, b, c (Å) | 153.2, 155.0, 141.5 |
| α, β, γ, (°) | 90.0, 92.6, 90.0 |
| Resolution (Å) | 50-3.0 (3.1-3.0)* |
| $R_{sym}$ or $R_{merge}$ | 0.068 (0.65) |
| I/σI | 20 (1.5) |
| Completeness (%) | 98.8 (92.3) |
| Redundancy | 3.6 (3.1) |
| Refinement | |
| Resolution (Å) | 50-3.1 |
| No. reflections | 56,210 |
| $R_{work}/R_{free}$ | 0.255/0.290 |
| No. atoms | |
| Protein | 12,802 |
| Ligand/ion | |
| Water | |
| B-factors | Kapβ2 Chain A: 90.4 Å$^2$ |
| | Kapβ2 Chain B: 95.9 Å$^2$ |
| | hnRNP M-NLS chain C: 102.7 Å$^2$ (51-58: 127.9 Å$^2$, 59-64: 81.4 Å$^2$, 65-68: 101.8 Å$^2$) |
| | hnRNP M-NLS chain D: 117.4 Å$^2$ (49-58: 149.8 Å$^2$, 59-64: 75.9 Å$^2$, 65-69: 120.6 Å$^2$) |
| Protein | |
| Ligand/ion | |
| Water | |
| R.m.s deviations | |
| Bond lengths (Å) | 1.197 |
| Bond angles (°) | 0.008 |

FIG. 9B is an image of NLSs of hnRNPs M (magenta) and A1 (2H4M; blue) upon superposition of Kapβ2 residues 435-780. Regions of structural similarity are highlighted in yellow. Structurally aligned NLS sequences, Cα-Cα distances and inhibitor M9M sequence are shown. The two NLSs trace different paths while lining a common interface on the structurally invariant Kapβ2 C-terminal arch (see FIGS. 9A and 9B; Kapβ2(435-780) Cα r.m.s. deviation is about 0.9 Å). The NLS termini are structurally diverse, consistent with apparent lack of sequence conservation (Lee, et al. 2006). At the N-terminus, hnRNP A1 residues 263-266 bind the convex side of Kapβ2, (Lee, et al. 2006), whereas the N-terminus of hnRNP M proceeds towards the Kapβ2 arch opening. At the C-terminus, hnRNP A1 is disordered beyond Pro288-Tyr289 while hnRNP M extend five residues beyond its Pro-Tyr motif. FIG. 9B is an image that illustrates residues 51-64 of hnRNP M and residues 273-289 of hnRNP A1 contact a common Kapβ2 surface with highest overlap at their Pro-Tyr motifs. R.m.s. deviations for all Pro-Tyr atoms and for arginine guanido-group atoms in the R/H/KX$_{(2-5)}$PY (SEQ ID NO: 1) motifs are 0.9 Å and 1.2 Å, respectively, upon Kapβ2 superposition. At the N-terminal motifs, hnRNP M residues 51-54 in the basic $^{50}$KEKNIKR$^{56}$ motif (SEQ ID NO: 95) and hnRNP A1 residues 274-277 in the hydrophobic motif also overlap (e.g., main chain r.m.s. deviation 1.3 Å). In contrast, intervening segments $^{61}$FE$^{62}$ in hnRNP M and $^{285}$SSG287 in hnRNP A1, and those between the N-terminal and R/H/KX$_{(2-5)}$PY motifs (SEQ ID NO: 1), diverge up to 4.0 Å and 7.2 Å, respectively as seen in FIG. 9B. Thus, the NLSs converge structurally at three sites: the N-terminal motif, the arginine and proline-tyrosine residues of the R/H/KX$_{(2-5)}$PY motif (SEQ ID NO: 1). These sites are key binding epitopes, confirming their designation as consensus sequences and structurally variable linkers are diverse in both sequence and length across the PY-NLS family. The multivalent nature of the PY-NLS-Kapβ2 interaction allows modulation of binding energy at each site to tune overall affinity to a narrow range suitable for regulation by nuclear RanGTP.

FIG. 9C is a plot of Kapβ2 binding energy in alanine mutants of hnRNPs A1[2] and M (ΔΔG=−RTln(K$_{D,wt}$/K$_{D,mutant}$); K$_D$s by ITC). FIG. 9C illustrates the affect of alanine mutants on binding.

Figure 10A:
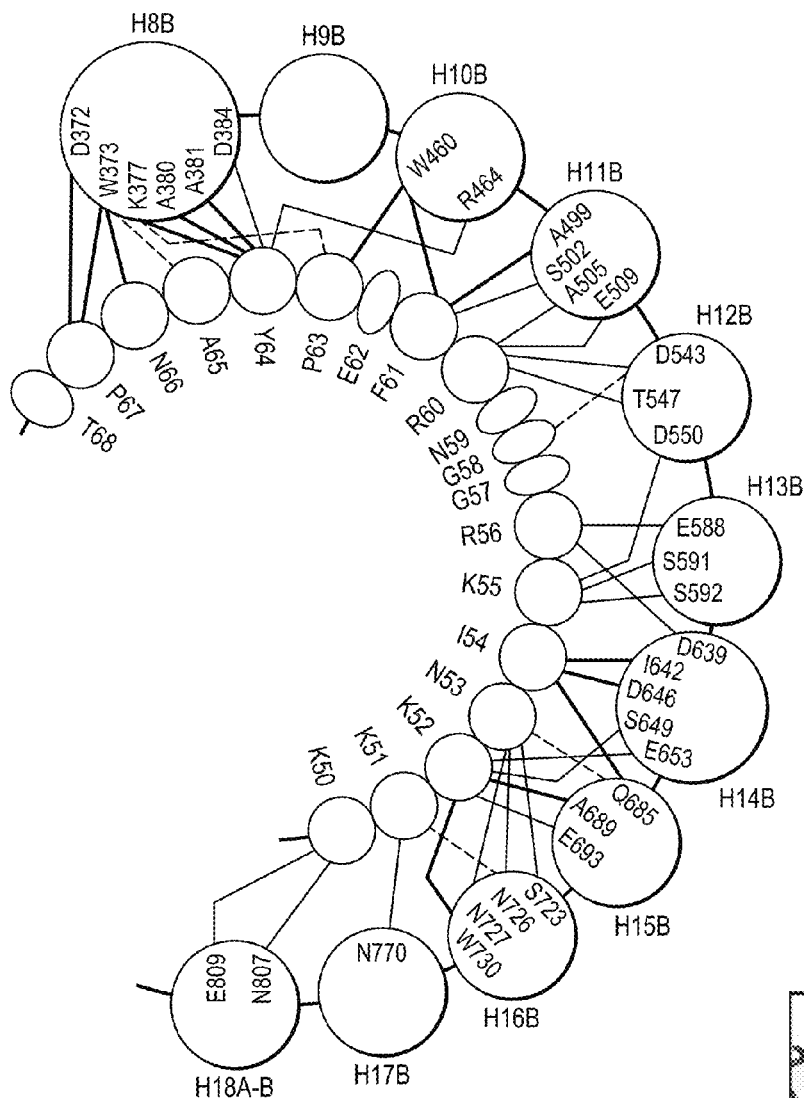
FIGS. 10A and 10B are images that illustrate the interactions between hnRNP M-NLS and Kapβ2.
Figure 10B:
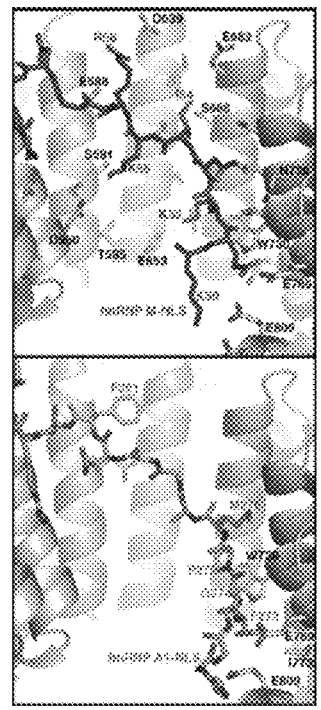
Figures 11A, 11B, 11C:
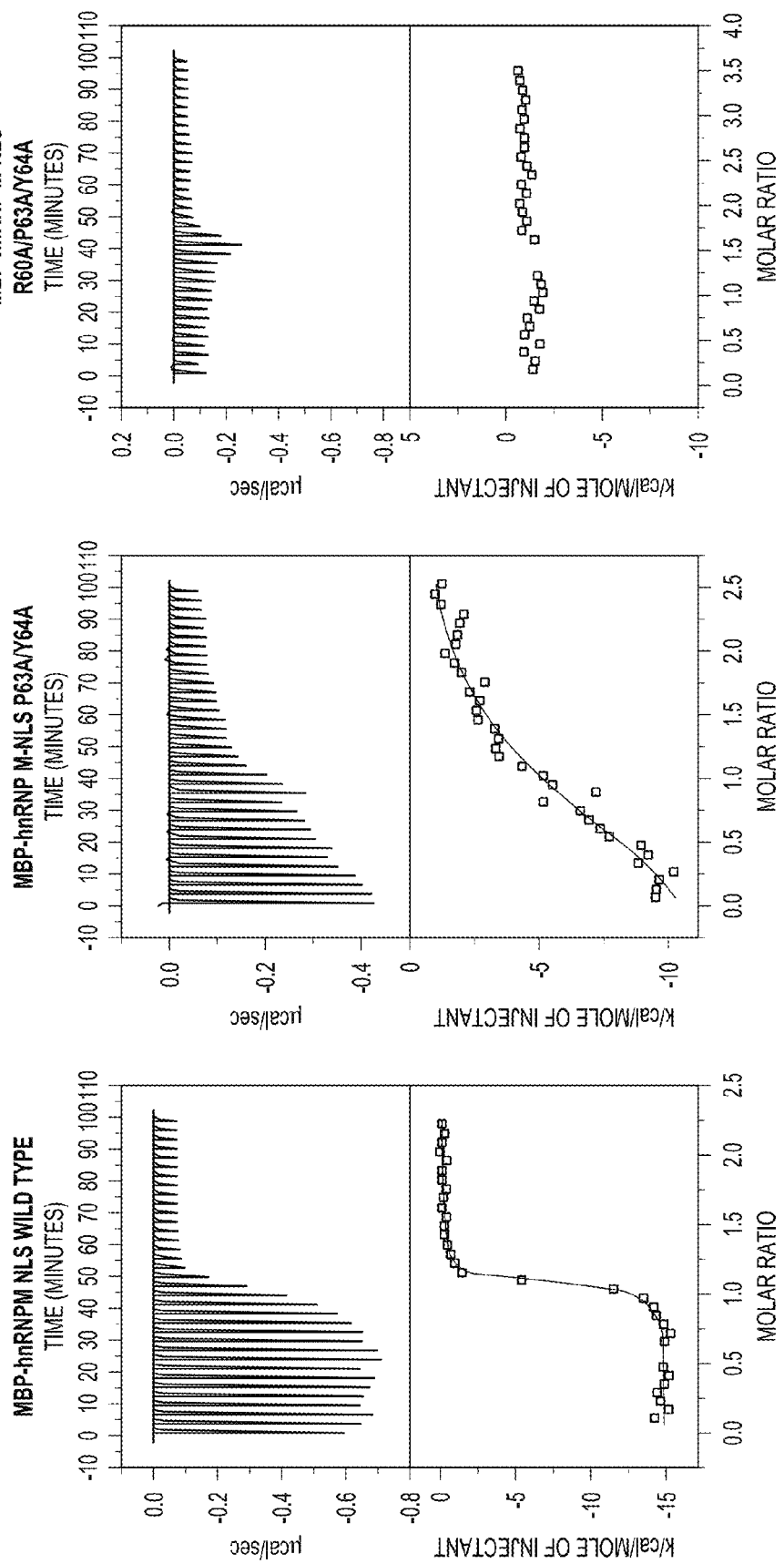
FIGS. 11A-11E are plots of isothermal titration calorimetry (ITC) measurements of select hnRNP M-NLSs binding to Kapβ2.
Figures 11D, 11E:
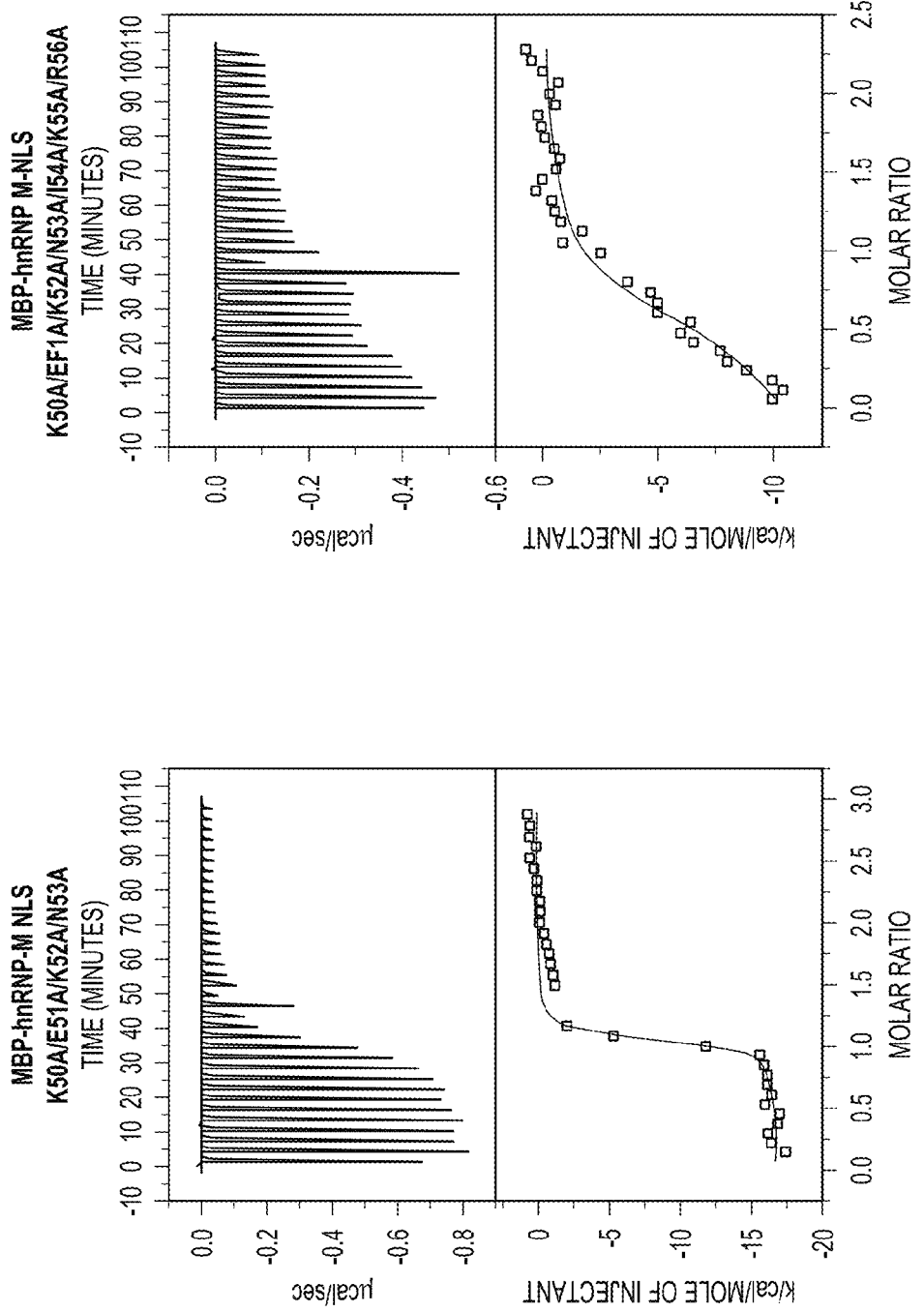

FIGS. 10A and 10B are images that illustrate the interactions between hnRNP M-NLS and Kapβ2. FIG. 10A Kapβ2-hnRNP M-NLS contacts (<4.0 Å). hnRNP M-NLS residues are shown as green circles and Kapβ2 helices as pink circles. Contacts involving the main chain and sidechains of hnRNP M-NLS are shown with dashed and solid lines, respectively. Hydrophobic contacts are in black and polar contacts in red. FIG. 10B is an image that illustrates the interactions between Kapβ2 (light brown) and the N-terminal NLS motifs of hnRNP M (magenta) and A1 (green). Despite a common Kapβ2 interface, functional groups in the hnRNP M basic $^{50}$KEKNIKR$^{56}$ motif (SEQ ID NO: 95) are very different from the hnRNP A1 hydrophobic $^{273}$FGPM$^{276}$ motif. Most sidechain interactions in the former are polar, while those in the latter are entirely hydrophobic. The corresponding Kapβ2 interface is highly acidic with scattered hydrophobic patches. hnRNP A1 Phe273 and Pro275 in the hydrophobic motif make hydrophobic contacts with Kapβ2 Ile773 and Trp730, respectively.

Similar hydrophobic contacts occur between the aliphatic portion of hnRNP M Lys52 sidechain and Kapβ2 Trp730, and between NLS Ile54, Kapβ2 Ile642 and aliphatic portions of Kapβ2 Asp646 and Gln685. Other sidechains within hnRNP M $^{50}$KEKNIKR$^{56}$ (SEQ ID NO: 95) make myriad polar and charged interactions with the acidic surface of Kapβ2. The relatively flat and open NLS binding site on Kapβ2 coupled with its mixed acidic/hydrophobic surface can accommodate diverse sequences, ranging from the hydrophobic segment in hPY-NLSs to basic groups in bPY-NLSs.

Despite structural conservation of key motifs, the distribution of binding energy along PY-NLSs is very different. In hnRNP A1, Gly274 is the only binding hotspot (Lee, et al. 2006; Fridell, et al. 1997; Nakielny, et al. 1996; Bogerd, et al. 1999) and energetic contribution from its C-terminal Pro-Tyr is modest (Lee, et al. 2006; Iijima, et al. 2006). In contrast, the only hnRNP M-NLS hotspot is at its Pro-Tyr motif as seen in the graph of FIG. 9C which illustrates the affect of Alanine mutants on binding.

FIGS. 11A-11E are plots of isothermal titration calorimetry (ITC) measurements of select hnRNP M-NLSs binding to Kapβ2. Table 6 illustrates the Kap β2 binding to hnRNP M NLS and mutants and the dissociation constants measured by isothermal titration calorimetry.

TABLE 6

| MBP-hnRNP M(41-70) | K$_D$ |
|---|---|
| Wild type | 10 ± 1.7 nM |
| K50A | 16.4 ± 0.4 nM |
| K52A | 14.6 ± 0.3 nM |
| N53A | 17.1 ± 0.5 nM |
| I54A | 8.8 ± 1.8 nM |
| K55A | 7.6 ± 2.3 nM |
| R56A | 13.9 ± 2 nM |
| K50A/E51A/K52A/N53A | 22.3 ± 4.1 nM |
| K50A/E51A/K52A/N53A/I54A/K55A/R56A | 1.2 ± 0.2 μM |
| F61A | 11.2 ± 1.6 nM |
| P63A/Y64A | 4.5 ± 0.7 μM |
| F61A/P63A/Y64A | 8.6 ± 1.4 μM |
| R59A/P63A/Y64A | ND |
| P67A | 8.7 ± 1.5 n |

Neither single alanine mutants within $^{50}$KEKNIKR$^{56}$ (SEQ ID NO: 95) nor a quadruple $^{50}$KEKN$^{53/}$AAAA hnRNP M mutant (SEQ ID NO: 96) had decreased affinity for Kapβ2 when measured by isothermal titration calorimetry (ITC). Affinity decreased substantially only when all seven residues were mutated to alanines in Table 6. Conformational flexibility suggested by high B-factors in this motif as seen in Table 5, may allow remaining basic sidechains in the mutants to reposition and compensate for truncated sidechains. Furthermore, the large number of acidic and electronegative sidechains on Kapβ2 may accommodate alternate conformations of the basic motif, as seen in FIG. 10b. Thus, the positive charge density rather than precise stereochemistry defines the basic motifs of bPY-NLSs.

Asymmetric locations of NLS hotspots in hnRNPs A1 and M, and the presence of variable linkers between the sites, allowed design of chimeric peptides with enhanced Kapβ2 binding affinities. A peptide that binds Kapβ2 with sufficiently high affinity may compete with natural substrates and be resistant to Ran-mediated release in the nucleus13 (Chook, et al. 2002), thus may function as a nuclear import inhibitor. We designed a peptide named M9M, which fuses the N-terminal half of hnRNP A1-NLS to the C-terminal half of hnRNP M-NLS and thus contains both binding hotspots as seen in FIG. 9B.

Figure 12A:
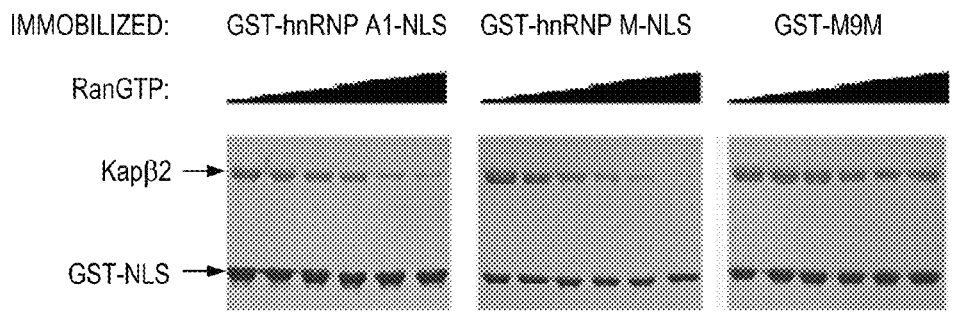
FIGS. 12A-12F are images of the results from in vitro and in vivo M9M inhibition studies.
Figure 12B:
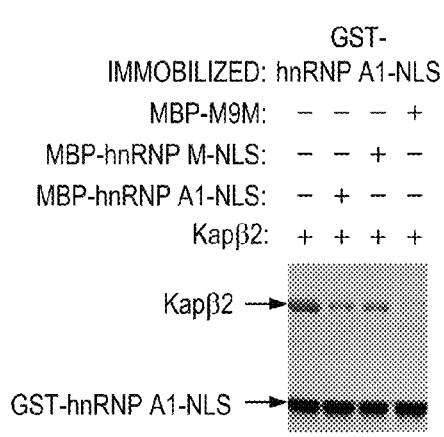
Figure 12C:
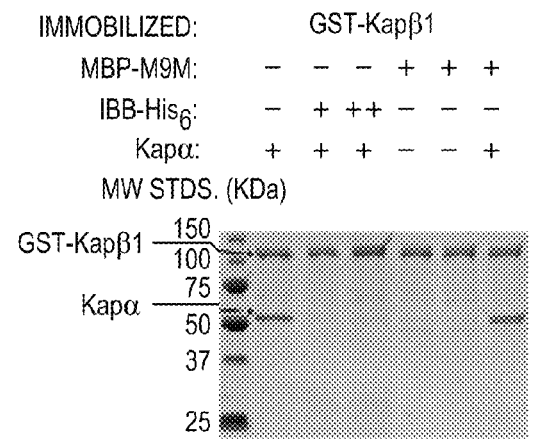
Figure 12D:
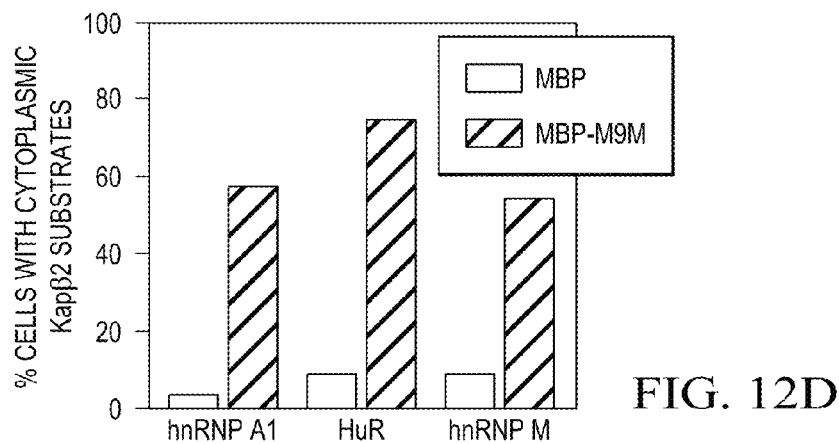
Figure 12E:
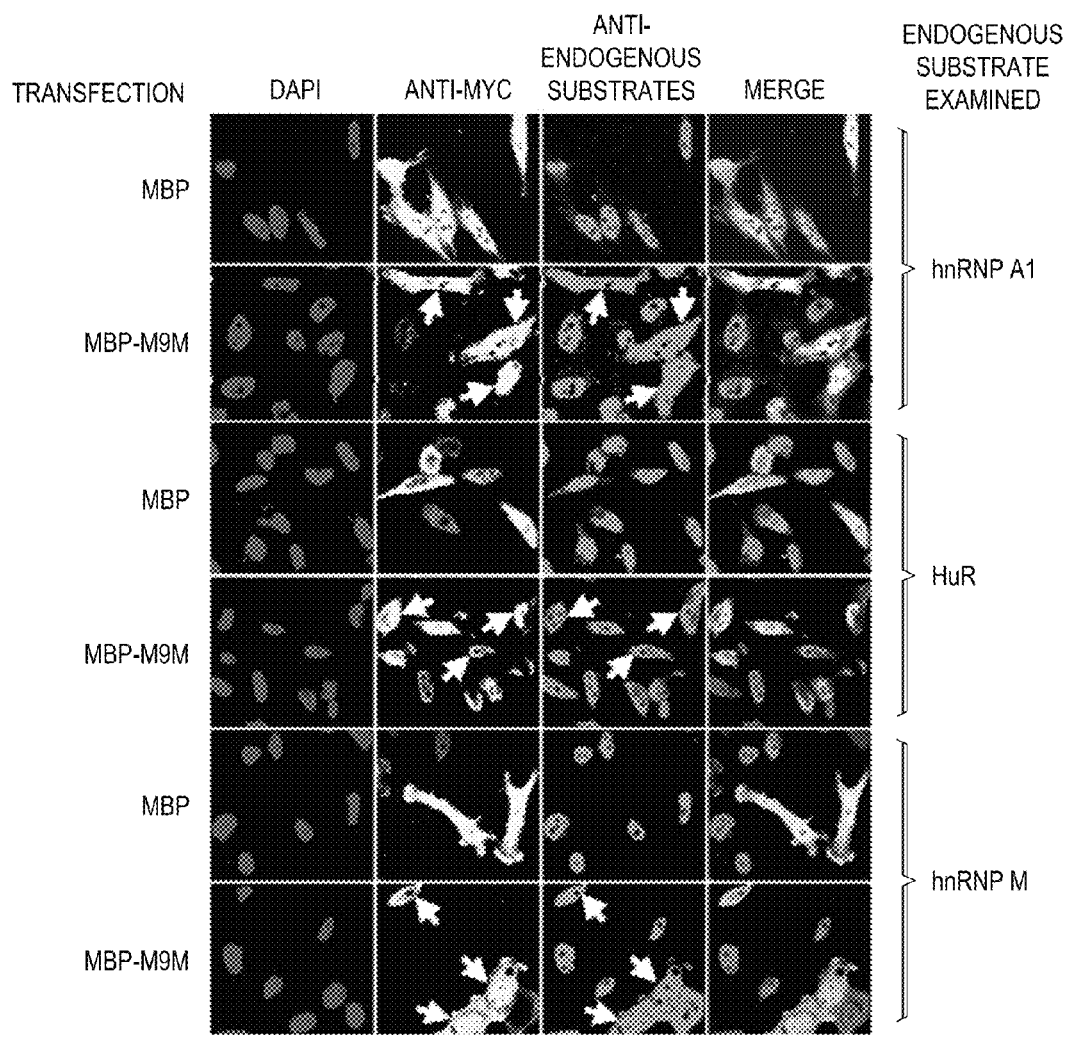
Figure 12F:
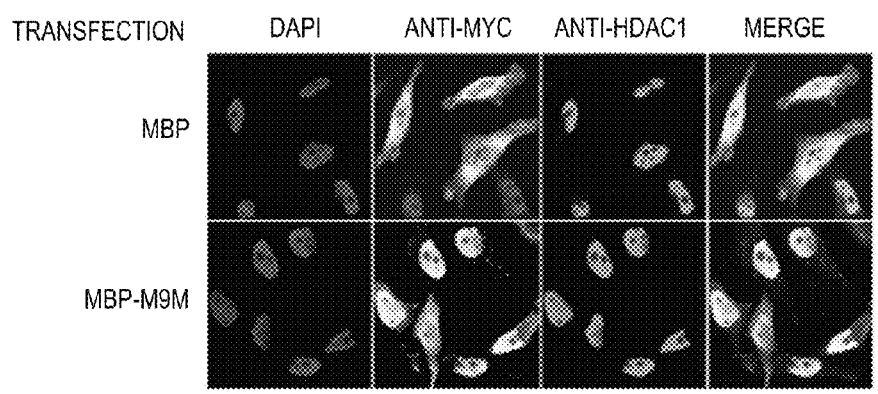

FIG. 12A to 12F are images of results from in vitro and in vivo M9M inhibition studies. FIG. 12A is an image of a coomasie-stained gel of GST-fusions of hnRNP A1-NLS, hnRNP M-NLS and M9M bound to Kapβ2 then dissociated by 0.3-1.6 μM RanGTP. FIG. 12B is an image of a coomasie-stained gel of a GST-hnRNP A1-NLS bound to Kapβ2 in the presence of buffer, MBP-hnRNP A1-NLS, MBP-hnRNP M-NLS or MBP-M9M. FIG. 12C is an image of a coomasie-stained gel that illustrating the interactions of GST-Kapβ1 with Kapα, Kapα in the presence of IBB domain, M9M, or Kapα in the presence of M9M. FIG. 12D is a histogram that shows the percentages of transfected cells with cytoplasmic Kapβ2 substrates. FIGS. 12E and 12F are immunofluorescence and De-Convolution microscopy images of Hela cells transfected with plasmids encoding myc-tagged MBP or MBP-M9M, using anti-myc and hnRNP A1, hnRNP M and HuR antibodies. FIG. 12F is an image of a localization of endogenous HDAC1 (Kapα/Kapβ1 substrate) is determined as control.

Quantitation of binding affinity with Isothermal Titration Calorimetry. Binding affinities for wild type and mutant MBP-hnRNP M-NLS were determined using Isothermal titration calorimetry (ITC). The experiments were performed using a MicroCal Omega VP-ITC calorimeter (MicroCal Inc., Northampton, Mass.). MBP-NLS proteins were dialyzed against buffer containing 20 mM Tris pH 7.5, 100 mM NaCl and 2 mM β-mercaptoethanol. 100-300 μM Wild type and mutant MBP-hnRNP A1-NLS proteins were titrated into the sample cell containing 10-100 μM full-length Kapβ2. All ITC experiments were done at 20° C. with 35 rounds of 8 μl injections. Data were plotted and analyzed using the single binding site model of MicroCal Origin software version 7.0.

Direct titration of ligand to protein in ITC reliably measures $K_D$ values in the $10^{-8}$ to $10^{-3}$ M range. hnRNP A1-NLS and hnRNP M-NLS bind Kapβ2 at the lower limit of this $K_D$ range ($K_D$ of 42 nM and 10 nM respectively, by standard ITC). Since the inhibitory M9M peptide appears to bind Kapβ2 with higher affinity than the natural NLSs of FIGS. 12A-12C, competition ITC were used to extend the range of measurable tight ($K_D < 10^{-9}$ M) affinities. hnRNP A1-NLS R284A/P288A/Y289A mutant ($K_D$ of 461 nM, measured by standard ITC[1]) was used as the competition displacement ligand. The calorimetry cell containing 12 μM Kapβ2 and 18 μM R284A/P288A/Y289A mutant of MBP-hnRNP A1-NLS was titrated with syringe solution of 108 μM MBP-M9M inhibitor (or 154 μM wildtype hnRNP A1-NLS as control). The experiment was repeated using 20 μM of the competition displacement ligand. Data were analyzed with the competition model in MicroCal Origin software version 7.0 to give $K_D$ values of 107 pM and 111 pM for M9M and $K_D$ of 20 nM for wildtype hnRNP A1-NLS of FIG. 13.

Subcellular localization of proteins in HeLa cells. MBP, MBP-hnRNP A1-NLS and MBP-M9M were subcloned into the modified pCS2-MT mammalian vector at Sal I and Not I sites. HeLa cells were maintained in DMEM (GIBCO BRL, Gaithersburg, Md.) with 10% fetal bovine serum (Gemini Bio-Products, West Sacramento, Calif.). Cells were grown on 12 mm coverslips placed in 24-well cell culture and transfected using EFFECTENE® (Qiagen, Valencia, Calif.) according to the manufacturer's instructions. After 16 hours, cells were fixed with 4% formaldehyde in PBS for 10 minutes at room temperature, permeabilized with 0.2% Triton X-100 in PBS for 5 minutes at room temperature, and blocked in 1% BSA/PBS. Cells were incubated with primary antibodies in 1% BSA/PBS for one hour at room temperature followed by secondary antibodies, and stained with 4,6-diamidino-2-phenylindole (DAPI). Goat-anti-myc-FITC polyclonal antibody (Bethyl Laboratories, Montgomery, Tex.) diluted to 5 ug/ml was used to detect the myc-MBP-peptides.

The monoclonal antibody 4C2 (a gift from Dr. M. Matunis) at 1:1000 dilution detected endogenous hnRNP A1 when incubated with goat-anti-mouse-Cy3 (Jackson ImmunoResearch Laboratories, West Grove, Pa.) antibody at 1:400 dilution. 4C2 has been previously shown to recognize human hnRNP A1, A2, B1 and B2[9] (Matunis, et al. 1992).

Figures 13A, 13B:
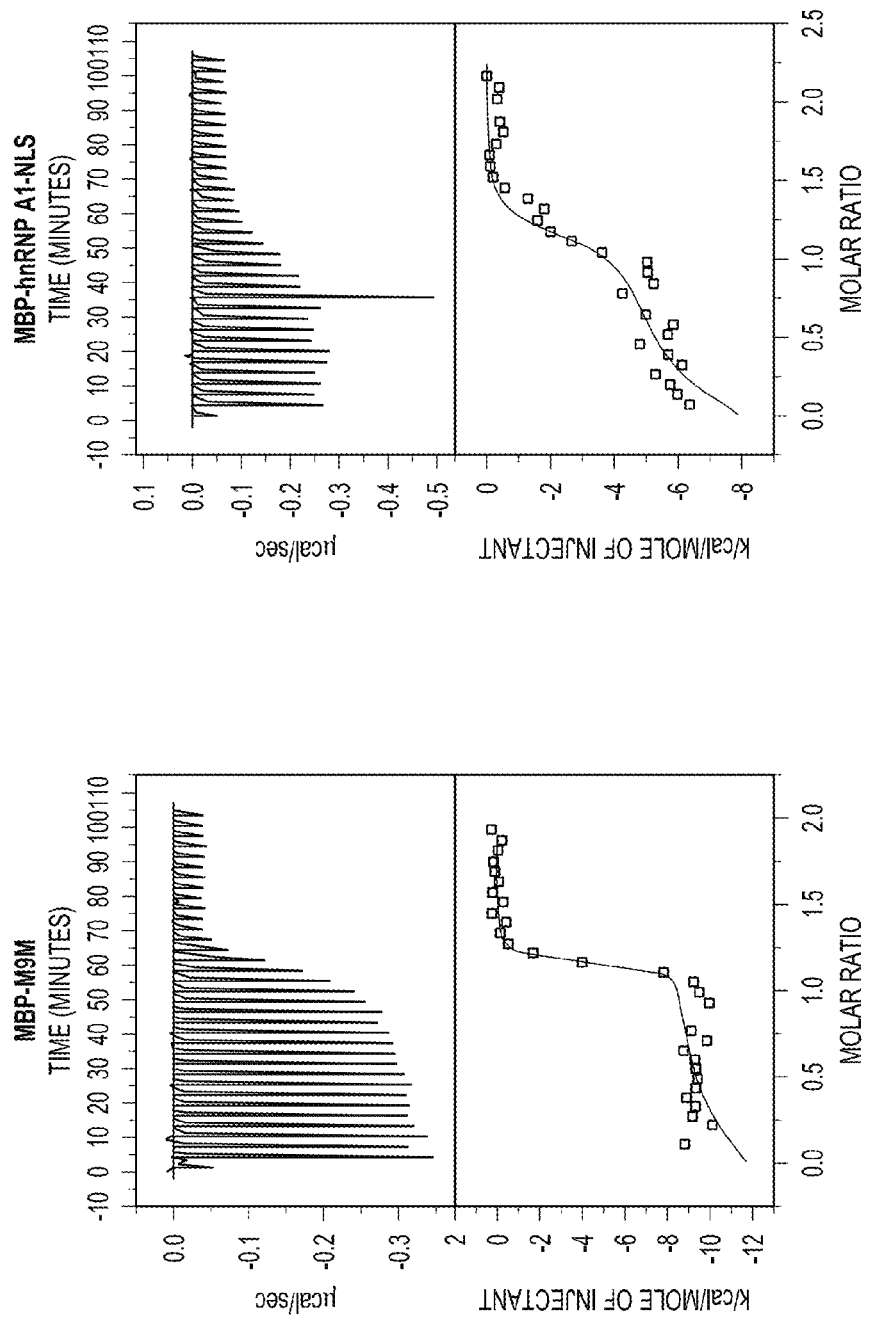
FIGS. 13A-13B are graphs of competition ITC data for inhibitor MBP-M9M binding to Kapβ2.

FIGS. 13A-13B are graphs of competition ITC data for inhibitor MBP-M9M binding to Kapβ2. FIG. 13A is a graph of the data for a calorimetry cell containing 12 μM Kapβ2 and 18 μM R284A/P288A/Y289A mutant of MBP-hnRNP A1-NLS was titrated with syringe solution containing 108 μM MBP-M9M inhibitor. The $K_D$ obtained for Kapβ2-M9M interaction is 107 pM. FIG. 13A is a graph of the data for a control experiment performed with 12 μM Kapβ2 and 20 μM R284A/P288A/Y289A mutant of MBP-hnRNP A1-NLS in the calorimetry cell, and titration with syringe solution of 154 μM of MBP-hnRNP A1-NLS. The $K_D$ obtained for Kapβ2-hnRNP A1-NLS interaction by ITC competition is 20 nM, comparable to $K_D$ of 42 nM by direct/standard ITC.

Western blot in FIGS. 13A-13B show that 4C2 recognizes the hnRNP A1 fragment 257-305 but not the chimeric inhibitory peptide M9M. Monoclonal antibody 2A6 (a gift from Dr. M. Swanson) was used at 1:1000 dilution to detect endogenous hnRNP M. Mouse anti-HuR antibody was purchased from Zymed and was used at 1:100 dilution. HDAC1 has previously been reported to be imported into the nucleus by Kapα/Kapβ1 (Smillie, et al. 2004).

In vitro binding assays have confirmed that recombinant HDAC1 binds Kapα but not Kapβ2 (data not shown). To detect endogenous HDAC1, mouse anti-HDAC1 monoclonal antibody 2E10 (Upstate Biotechnology; diluted 1:500) was used. Cells were then examined in a Zeiss Axiovert 200M microscope with De-convolution and Apotome systems. Images were acquired with the AxioVision software (Carl Zeiss Image Solutions) and processed with Image J software (National Institutes of Health, Bethesda, Md.). HuR and hnRNP M images were acquired using a Leica TCS SP5 confocal microscope and the Leica LAS AF software (Leica Microsystems Inc). 52-157 transfected cells were analyzed for each of the experiments, and percentages with cytoplasmic substrates are shown in a histogram of FIG. 12D.

For western blot analysis, MBP-hnRNP A1-NLS, MBP-hnRNP M-NLS, MBP-M9M proteins or HeLa lysates were resolved on SDS-PAGE, transferred to PVDF membrane and probed with monoclonal antibody 4C2 diluted at 1:2000 and antibody 2A6 diluted at 1:1000. Secondary horseradish peroxidase-conjugated anti-mouse antibody (diluted 1:10000, Amersham) and the ECL system (Amersham) were used to visualize the blots.

M9M shows decreased dissociation by RanGTP when bound to Kapβ2, competes effectively with wildtype NLS and binds specifically to Kapβ2 but not Kapβ1, as seen in FIG. 12A-12C, thus behaving like a Kapβ2-specific inhibitor. The mechanism of inhibition is explained by the 200-fold tighter binding of M9M to the PY-NLS binding site of Kapβ2.

Figure 14:
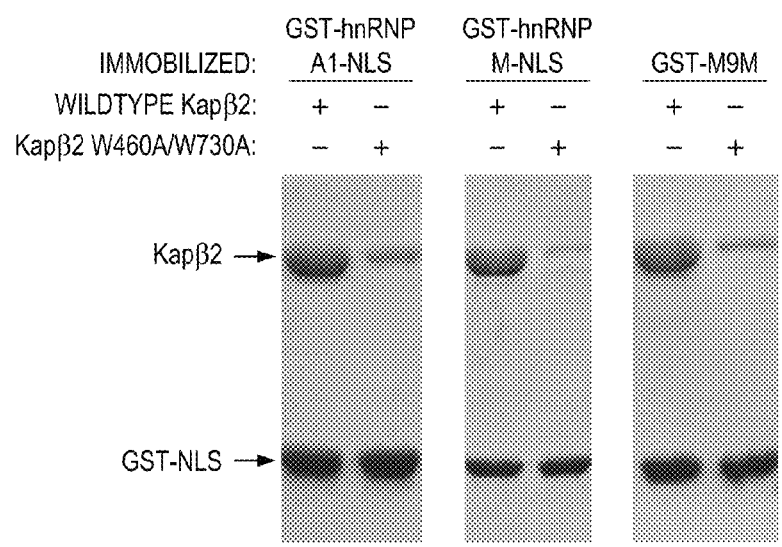
FIG. 14 is an image of a gel illustrating the M9M, hnRNP M-NLS and nRNP A1-NLS bind to the same site on Kapβ2.

FIG. 14 is an image of a gel illustrating the M9M, hnRNP M-NLS and hnRNP A1-NLS bind to the same site on Kapβ2. Immobilized GST-fusions of hnRNP A1-NLS, hnRNP M-NLS and inhibitor M9M all show significantly decreased binding to Kapβ2 W460A/W730A mutant. Residue W460A of Kapβ2 contacts the C-terminal PY motif of the PY-NLSs whereas W730A contacts both the N-terminal hydrophobic motif of hnRNP A1 hPY-NLS and the N-terminal basic motif of the hnRNP M bPY-NLS. The competition ITC of FIGS. 13 and the images off FIG. 14 show $K_D$ of 107 pM versus 20 nM for hnRNP A1-NLS.

Figure 15A:
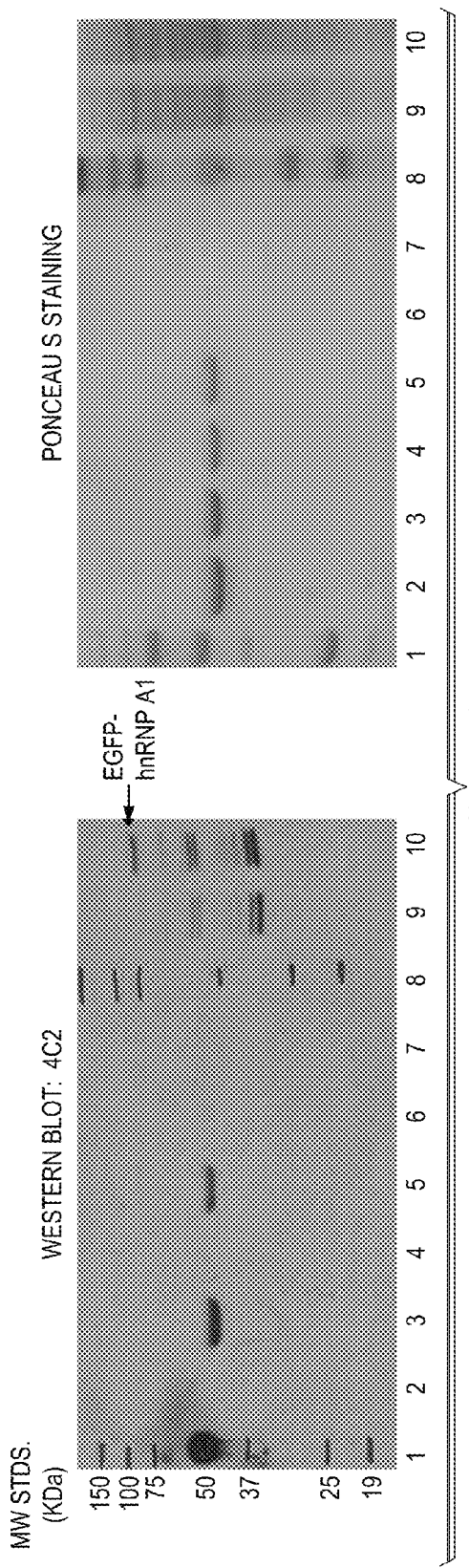
FIGS. 15A and 15B are images of western blots using antibodies against hnRNPs A1 and M.
Figure 15B:
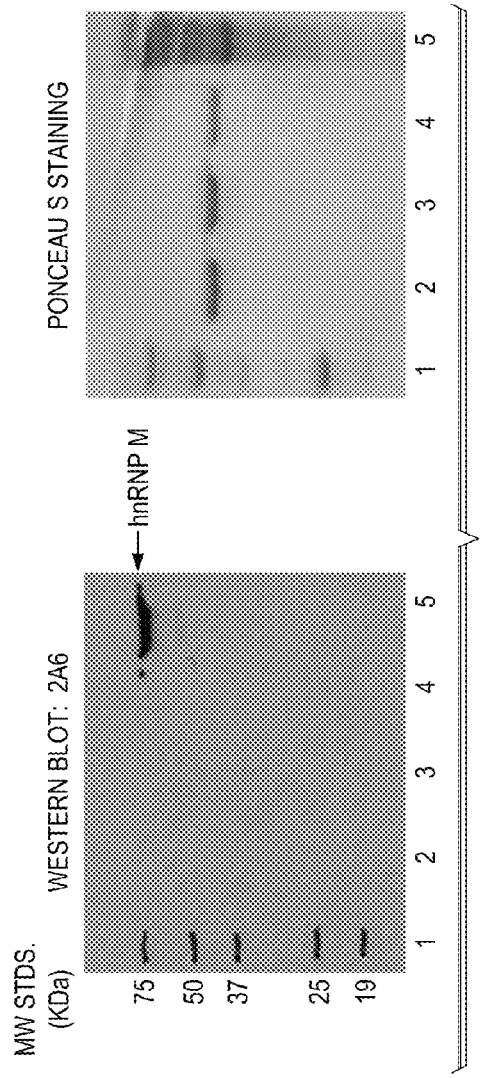

FIGS. 15A and 15B are images of western blots using antibodies against hnRNPs A1 and M. FIG. 15A is a image of a western blot with antibody 4C2 (left), which recognizes human hnRNPs A1, A2 and B1, and visualization of proteins by Ponceau staining (right). Lanes 2, 4 and 6 contain 2 ug, 1 ug, and 0.1 ug of MBP-M9M; lanes 3, 5 and 7 contain 2 ug, 1 ug and 0.1 ug of MBP-hnRNP A1-NLS; Lane 9 contains control HeLa cell lysate and lane 10 has lysate from myc-EGFP-A1-transfected HeLa cells. Lanes 1 and 8 are molecular weight standards.

FIG. 15B is an image of a western blot with antibody 2A6 (left), which recognizes human hnRNP M, and visualization of proteins by Ponceau staining (right). Lane 1 contains molecular weight standards; Lane 2 contains 1 ug of MBP-M9M; Lane 3 contains 1 ug of MBP-hnRNP A1-NLS; Lane 4 contains 1 ug of MBP-hnRNP M-NLS; Lane 5 contains Hela cell lysate. Transfection of M9M in HeLa cells mislocalizes endogenous Kapβ2 substrates hnRNPs A1, M and HuR from the nucleus to the cytoplasm but not endogenous Kapα/Kapβ1 substrate HDAC1 (Smillie, et al. 2004). Thus, M9M can specifically inhibit Kapβ2-mediated nuclear import in cells.

Both bPY- and hPY-NLSs bind Kapβ2 in extended conformation with structural conservation at their Arg and Pro-Tyr residues of the C-terminal $R/K/HX_{2-5}PY$ motifs (SEQ ID NO: 1) and at their N-terminal basic/hydrophobic motifs, confirming both the requirement for intrinsic structural disorder in PY-NLSs and the identification of N-terminal hydrophobic/basic and C-terminal $R/K/HX_{2-5}PY$ consensus motifs (SEQ ID NO: 1). The asymmetric NLS binding hotspots in hnRNPs M and A1 provides the design of the M9M peptide of the present invention, which binds Kapβ2 200-fold tighter than natural NLSs and specifically inhibits Kapβ2-mediated nuclear import in cells. Coordinates and structure factors deposited with accession code 2OT8.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

References

Allemand, E., Guil, S., Myers, M., Moscat, J., Caceres, J. F., and Krainer, A. R. (2005). Regulation of heterogenous nuclear ribonucleoprotein A1 transport by phosphorylation in cells stressed by osmotic shock. Proc Natl Acad Sci USA 102, 3605-3610.

Apweiler, R., Bairoch, A., and Wu, C. H. (2004). Protein sequence databases. Current opinion in chemical biology 8, 76-80.

Arnaoutov, A., Azuma, Y., Ribbeck, K., Joseph, J., Boyarchuk, Y., Karpova, T., McNally, J., and Dasso, M. (2005). Crm1 is a mitotic effector of Ran-GTP in somatic cells. Nat Cell Biol 7, 626-632.

Bairoch, A., Boeckmann, B., Ferro, S., and E., G. (2004). Swiss-Prot: Juggling between evolution and stability Brief Bioinform 5, 39-55.

Bogerd, H. P., Benson, R. E., Truant, R., Herold, A., Phingbodhipakkiya, M., and Cullen, B. R. (1999). Definition of a consensus transportin-specific nucleocytoplasmic transport signal. J Biol Chem 274, 9771-9777.

Bonifaci, N., Moroianu, J., Radu, A., and Blobel, G. (1997). Karyopherin beta2 mediates nuclear import of a mRNA binding protein. Proc Natl Acad Sci USA 94, 5055-5060.

Brunger, A. T., D., A. P., Clore, G. M., DeLano, W. L., Gros, P., Grosse-Kunstleve, R. W., Jiang, J. S., Kuszewski, J., Nilges, M., Pannu, N. S., et al. (1998). Crystallography & NMR System: A new software suite for macromolecular structure determination. Acta Cryst A D54, 905-921.

Budhu, A. S., and Wang, X. W. (2005). Loading and unloading: orchestrating centrosome duplication and spindle assembly by Ran/Crm1. Cell Cycle 4, 1510-1514.

CCP4 (1994). The CCP4 suite: programs for X-ray crystallography. Acta Crystallogr D 50.

Chook, Y., and Blobel, G. (1999). Structure of the nuclear transport complex karyopherin-beta2-Ran.GppNHp. Nature 399, 230-237.

Chook, Y. M., and Blobel, G. (2001). Karyopherins and nuclear import. Current Opinions in Structural Biology 11.

Chook, Y. M., Jung, A., Rosen, M. K., and Blobel, G. (2002). Uncoupling Kapb2 substrate dissociation and Ran binding. Biochemistry 41, 6955-6966.

Cingolani, G., Bednenko, J., Gillespie, M. T., and Gerace, L. (2002). Molecular basis for the recognition of a nonclassical nuclear localization signal by importin beta. Mol Cell 10, 1345-1353.

Cingolani, G., Petosa, C., Weis, K., and Muller, C. W. (1999). Structure of importin-beta bound to the IBB domain of importin-alpha. Nature 399, 221-229.

Conti, E., and Izaurralde, E. (2001). Nucleocytoplasmic transport enters the atomic age. Curr Opin Cell Biol 13, 310-319.

Cook, A., Fernandez, E., Lindner, D., Ebert, J., Schlenstedt, G., and Conti, E. (2005). The structure of the nuclear export receptor Cse1 in its cytosolic state reveals a closed conformation incompatible with cargo binding. Mol Cell 18, 355-367.

Datar, K. V., Dreyfuss, G. & Swanson, M. S. Nucleic Acids Res 21, 439-46 (1993).

DeLano, W. L. (2002). The PyMOL User's Manual, DeLano Scientific, San Carlos, Calif. Fan, X. C., and Steitz, J. A. (1998). HNS, a nuclear-cytoplasmic shuttling sequence in HuR. Proc Natl Acad Sci USA 95, 15293-15298.

Dingwall, C. & Laskey, R. A. Trends Biol. Sci. 16, 178-181 (1991).

Emsley, P. & Cowtan, K. Acta Crystallogr D Biol Crystallogr 60, 2126-32 (2004).

Floer, M., and Blobel, G. (1996). The nuclear transport factor karyopherin beta binds stoichiometrically to Ran-GTP and inhibits the Ran GTPase activating protein. J Biol Chem 271, 5313-5316.

Fridell, R. A., Truant, R., Thorne, L., Benson, R. E., and Cullen, B. R. (1997). Nuclear import of hnRNP A1 is mediated by a novel cellular cofactor related to karyopherin-beta. J Cell Sci 110, 1325-1331.

Fukuhara, N., Fernandez, E., Ebert, J., Conti, E., and Svergun, D. (2004). Conformational variability of nucleo-cytoplasmic transport factors. J Biol Chem 279, 176-181.

Gattiker, A., Gasteiger, E., and Bairoch, A. (2002). ScanProsite: a reference implementation of a PROSITE scanning tool. Applied Bioinformatics 1, 107-108.

Gattoni, R. et al. Nucleic Acids Res 24, 2535-42 (1996).

Gorlich, D., and Kutay, U. (1999). Transport between the cell nucleus and the cytoplasm. Annu Rev Cell Dev Biol 15, 607-660.

Gorlich, D., Pante, N., Kutay, U., Aebi, U., and Bischoff, F. R. (1996). Identification of different roles for RanGDP and RanGTP in nuclear protein import. Embo J 15, 5584-5594.

Guttinger, S., Muhlhausser, P., Koller-Eichhorn, R., Brennecke, J., and Kutay, U. (2004). Transportin2 functions as importin and mediates nuclear import of HuR. Proc Natl Acad Sci USA 101, 2918-2923.

Hamamoto, T., Gunji, S., Tsuji, H. & Beppu, T. J Antibiot (Tokyo) 36, 639-45 (1983).

Harel, A., and Forbes, D. J. (2004). Importin beta: conducting a much larger cellular symphony. Mol Cell 16, 319-330.

Hase, M. E., Yalamanchili, P. & Visa, N. J Biol Chem (2006).

Iijima, M., Suzuki, M., Tanabe, A., Nishimura, A., and Yamada, M. (2006). Two motifs essential for nuclear import of the hnRNP A1 nucleocytoplasmic shuttling sequence M9 core. FEBS Lett 580, 1365-1370.

Jones, T. A., Cowan, S. W., and Kjelgaard, M. (1991). Improved methods for building protein models in electron density maps and the location of errors in these models. Acta Crystallogr A 47, 110-119.

Kawamura, H., Tomozoe, Y., Akagi, T., Kamei, D., Ochiai, M., and Yamada, M. (2002). Identification of the nucleocytoplasmic shuttling sequence of heterogeneous nuclear ribonucleoprotein D-like protein JKTBP and its interaction with mRNA. J Biol Chem 277, 2732-2739.

Lee, B. J. et al. Cell 126, 543-58 (2006).

Lee, S. J., Matsuura, Y., Liu, S. M., Stewart, M., and (2005). Structural basis for nuclear import complex dissociation by RanGTP. Nature 435, 693-696.

Lee, S. J., Sekimoto, T., Yamashita, E., Nagoshi, E., Nakagawa, A., Imamoto, N., Yoshimura, M., Sakai, H., Chong, K. T., Tsukihara, T., and Yoneda, Y. (2003). The structure of importin-beta bound to SREBP-2: nuclear import of a transcription factor. Science 302, 1571-1575.

Linding, R., Jensen, L. J., Diella, F., Bork, P., Gibson, T. J., and Russell, R. B. (2003). Protein disorder prediction: implications for structural proteomics. Structure (Camb) 11, 1453-1459.

Matunis, M. J., Matunis, E. L. & Dreyfuss, G. J Cell Biol 116, 245-55 (1992).

Matsuura, Y., and Stewart, M. (2004). Structural basis for the assembly of a nuclear export complex. Nature 432, 872-877.

McCoy, A. J., Grosse-Kunstleve, R. W., Storoni, L. C., and Read, R. J. (2005). Likelihood-enhanced fast translation functions. Acta Cryst D61, 458-464.

Mosammaparast, N., and Pemberton, L. F. (2004). Karyopherins: from nuclear-transport mediators to nuclear-function regulators. Trends Cell Biol 14, 547-556.

Nakielny, S., Siomi, M. C., Siomi, H., Michael, W. M., Pollard, V., and Dreyfuss, G. (1996). Transportin: nuclear transport receptor of a novel nuclear protein import pathway. Exp Cell Res 229, 261-266.

Nicholls, A., Sharp, K. A., and Honig, B. (1991). Protein folding and association: insights from the interfacial and thermodynamic properties of hydrocarbons. Proteins: Struct Funct Genet 11, 281-296.

Otwinowski, Z., and Minor, W. (1997). Processing of X-ray Diffraction Data Collected in Oscillation Mode. Methods in Enzymology 276, 307-326.

Petosa, C., Schoehn, G., Askjaer, P., Bauer, U., Moulin, M., Steuerwald, U., Soler-Lopez, M., Baudin, F., Mattaj, I. W., and Muller, C. W. (2004). Architecture of CRM1/Exportin1 suggests how cooperativity is achieved during formation of a nuclear export complex. Mol Cell 16, 761-775.

Pollard, V. W., Michael, W. M., Nakielny, S., Siomi, M. C., Wang, F., and Dreyfuss, G. (1996). A novel receptor-mediated nuclear protein import pathway. Cell 86, 985-994.

Rebane, A., Aab, A., and Steitz, J. A. (2004). Transportins 1 and 2 are redundant nuclear import factors for hnRNP A1 and HuR. Rna 10, 590-599.

Siomi, H., and Dreyfuss, G. (1995). A nuclear localization domain in the hnRNP A1 protein. J Cell Biol 129, 551-560.

Siomi, M. C., Eder, P. S., Kataoka, N., Wan, L., Liu, Q., and Dreyfuss, G. (1997). Transportin-mediated nuclear import of heterogeneous nuclear RNP proteins. J Cell Biol 138, 1181-1192.

Smillie, D. A., Llinas, A. J., Ryan, J. T., Kemp, G. D. & Sommerville, J. J Cell Sci 117, 1857-66 (2004).

Suzuki, M., Iijima, M., Nishimura, A., Tomozoe, Y., Kamei, D., and Yamada, M. (2005). Two separate regions essential for nuclear import of the hnRNP D nucleocytoplasmic shuttling sequence. Febs J 272, 3975-3987.

Truant, R., Kang, Y., and Cullen, B. R. (1999). The human tap nuclear RNA export factor contains a novel transportin-dependent nuclear localization signal that lacks nuclear export signal function. J Biol Chem 274, 32167-32171.

Vetter, I. R., Arndt, A., Kutay, U., Gorlich, D., and Wittinghofer, A. (1999). Structural view of the Ran-Importin beta interaction at 2.3 A resolution. Cell 97, 635-646.

Weighardt, F., Biamonti, G., and Riva, S. (1995). Nucleocytoplasmic distribution of human hnRNP proteins: a search for the targeting domains in hnRNP A1. J Cell Sci 108 (Pt 2), 545-555.

Weis, K. (2003). Regulating access to the genome: nucleocytoplasmic transport throughout the cell cycle. Cell 112, 441-451.

Yashiroda, Y. & Yoshida, M. Curr Med Chem 10, 741-8 (2003).

What is claimed is:

1. A chimeric membrane localization polypeptide that localizes an agent to a nuclear membrane comprising: N-terminus of a Heterogeneous Nuclear Ribonucleoprotein A1 (hnRNP A 1)-Nuclear Localization Signal (NLS), and the N-terminus of the hnRNP A1-NLS fused to C-terminus of a Heterogeneous Nuclear Ribonucleoprotein M (hnRNP M)-Nuclear Localization Signal (NLS); wherein the chimeric polypeptide comprises SEQ ID NO: 128; wherein the chimeric membrane localization polypeptide is capable of localization to the nuclear membrane of a cell.

2. The polypeptide of claim 1, further comprising one or more agents associated with the peptide, wherein the one or more agents are selected from nucleic acids, peptide nucleic acids (PNAs), drugs, pharmaceutical agents, isotopes, heavy metals, nano-particles, lipids, carbohydrates, proteins, amino acids, vitamins, polymers, detectable labels, a PY-Nuclear Localization Signals (PY-NLS) and combinations thereof.

3. A method of localizing an agent about a cellular membrane comprising the step of: contacting one or more cells with at least a portion of a membrane localization fusion protein, wherein the membrane localization fusion protein comprises one or more agents associated with, N-terminus of a Heterogeneous Nuclear Ribonucleoprotein A1 (hnRNP A1)-Nuclear Localization Signal (NLS) fused to C-terminal of a Heterogeneous Nuclear Ribonucleoprotein M (hnRNP M)-Nuclear Localization Signal (NLS) selected from at least one of SEQ ID NO: 1:128; wherein the membrane localization fusion protein is capable of localization to the nuclear membrane of a cell.

4. The method of claim 3, wherein the one or more agents are selected from nucleic acids, peptide nucleic acids (PNAs), drugs, pharmaceutical agents, isotopes, heavy metals, nano-particles, lipids, carbohydrates, proteins, amino acids, vitamins, polymers, detectable labels, a PY-NLS and combinations thereof.

5. The method of claim 3, wherein the one or more agents comprise one or more nucleic acids, peptide nucleic acids (PNAs), drugs, pharmaceutical agents, isotopes, heavy metals, nano-particles, lipids, carbohydrates, proteins, amino acids, vitamins, polymers, detectable labels, polypeptides that translocates an agent nuclear membranes and combinations thereof.

6. A kit having a fusion protein to localize an agent about a nuclear membrane comprising:

N-terminal of a Heterogeneous Nuclear Ribonucleoprotein A1 (hnRNP A1)-Nuclear Localization Signal (NLS)

fused to C-terminal of a Heterogeneous Nuclear Ribonucleoprotein M (hnRNP) M-Nuclear Localization Signal (NLS), wherein the membrane localization polypeptide comprises SEQ ID NO: 128; and an agent binding motif, wherein the agent is localized to the nuclear membrane of a cell.

7. The kit of claim 6, wherein the agent comprises one or more nucleic acids, peptide nucleic acids (PNAs), drugs, pharmaceutical agents, isotopes, heavy metals, nano-particles, lipids, carbohydrates, proteins, amino acids, vitamins, polymers, detectable labels, polypeptides that translocates an agent nuclear membranes and combinations thereof.

* * * * *